US009441028B2

(12) United States Patent
Frederiksen

(10) Patent No.: US 9,441,028 B2
(45) Date of Patent: Sep. 13, 2016

(54) COUNTER CURRENT PURIFICATION OF POLYPEPTIDES

(75) Inventor: Søren Søndergaard Frederiksen, Copenhagen V (DE)

(73) Assignee: Novo Nordisk A/S, Bagsvaerd (DK)

( * ) Notice: Subject to any disclaimer, the term of this patent is extended or adjusted under 35 U.S.C. 154(b) by 647 days.

(21) Appl. No.: 13/133,207

(22) PCT Filed: Dec. 8, 2009

(86) PCT No.: PCT/EP2009/066630
§ 371 (c)(1),
(2), (4) Date: Aug. 17, 2011

(87) PCT Pub. No.: WO2010/066734
PCT Pub. Date: Jun. 17, 2010

(65) Prior Publication Data
US 2012/0041174 A1 Feb. 16, 2012

Related U.S. Application Data

(60) Provisional application No. 61/121,741, filed on Dec. 11, 2008.

(30) Foreign Application Priority Data

Dec. 8, 2008 (EP) ..................... 08170945
Dec. 23, 2008 (EP) ..................... 08172730

(51) Int. Cl.
*C07K 1/14* (2006.01)
*C07K 1/16* (2006.01)
*C07K 1/20* (2006.01)
*C07K 1/18* (2006.01)
*C07K 14/605* (2006.01)
*C07K 14/435* (2006.01)
*B01D 15/18* (2006.01)
*B01D 15/32* (2006.01)
*B01D 15/36* (2006.01)

(52) U.S. Cl.
CPC ........... *C07K 14/605* (2013.01); *B01D 15/185* (2013.01); *B01D 15/1807* (2013.01); *C07K 14/435* (2013.01); *B01D 15/325* (2013.01); *B01D 15/327* (2013.01); *B01D 15/361* (2013.01)

(58) Field of Classification Search
CPC ........... G01N 1/00; G01N 2030/8831; G01N 2030/8809; G01N 2030/42; G01N 2030/28; G01N 2030/26; G01N 2030/02; G01N 2030/00; B01D 15/1821; B01D 15/1805; B01D 15/08; B01D 15/02; B01D 15/00
See application file for complete search history.

(56) References Cited

U.S. PATENT DOCUMENTS

| 2,985,589 A | 5/1961 | Broughton |
| 3,040,777 A | 6/1962 | Carson |
| 4,437,051 A | 3/1984 | Muto et al. |
| 4,574,840 A | 3/1986 | Schumann et al. |
| 4,614,205 A | 9/1986 | Oroskar |
| 5,424,286 A | 6/1995 | Eng |
| 5,635,072 A | 6/1997 | Moran |
| 6,455,736 B1 | 9/2002 | Zinnen et al. |
| 6,458,995 B1 | 10/2002 | Cheung et al. |
| 6,461,858 B1 | 10/2002 | Gabriel et al. |
| 6,462,221 B1 | 10/2002 | Gabriel et al. |
| 6,544,413 B1 | 4/2003 | Nagamatsu et al. |
| 6,719,001 B2 | 4/2004 | Ahlgren et al. |
| 6,979,402 B1 | 12/2005 | Sprague et al. |

FOREIGN PATENT DOCUMENTS

| CN | 1100427 C | 1/2003 | |
| CN | 1403582 A | 3/2003 | |
| CN | 101139382 | 3/2008 | |
| EP | 699686 A2 | 3/1996 | |
| EP | 0708179 A2 | 4/1996 | |
| EP | 1 349 866 A2 | 10/2003 | |
| JP | 2002539219 A | 11/2002 | |
| JP | 2007-526234 A | 9/2007 | |
| WO | 87/06941 A1 | 11/1987 | |
| WO | 90/11296 A1 | 10/1990 | |
| WO | 91/11457 A1 | 8/1991 | |
| WO | 97/46584 A1 | 12/1997 | |
| WO | WO 01/87924 | 11/2001 | |
| WO | WO 02/32537 | 4/2002 | |
| WO | WO 03/068764 | * 8/2003 | ........... C07D 307/62 |
| WO | WO 2004/024284 | 3/2004 | |
| WO | WO 2005/019262 | 3/2005 | |
| WO | WO 2008/048395 | 4/2008 | |
| WO | WO 2008/153472 | 12/2008 | |

OTHER PUBLICATIONS

Ke_ler et al., Journal of Chromatography A (2007) 1176, 69-78.*
Storti et al., AIChE Journal (1993) 39(3), 471-492.*
Said et al., Eur. J. Biochem. (1972) 28, 199-204.*
Jensen, Journal of Chromatography, 2000, vol. 873, No. 2, pp. 149-162.
Houwing, Journal of Chromatography, 2002, vol. 944, No. 1-2, pp. 189-201.
Kessler, Journal of Chromatograph, 2007, vol. 1176, No. 1-2, pp. 69-78.
Park, Process Biochemistry, 2006, vol. 41,pp. 1072-1082.
Pedersen, Journal of Chromatography B, 2003, vol. 790, No. 1-2, pp. 161-173.

(Continued)

Primary Examiner — Marcela M Cordero Garcia
Assistant Examiner — Catherine Mader
(74) Attorney, Agent, or Firm — Leon Y. Lum

(57) ABSTRACT

The present invention relates to methods for the purification of polypeptides using counter current chromatography. In particular the present invention relates to the use of counter current chromatography for the purification of recombinant GLP-1.

14 Claims, 26 Drawing Sheets

(56) References Cited

OTHER PUBLICATIONS

Figure 1:
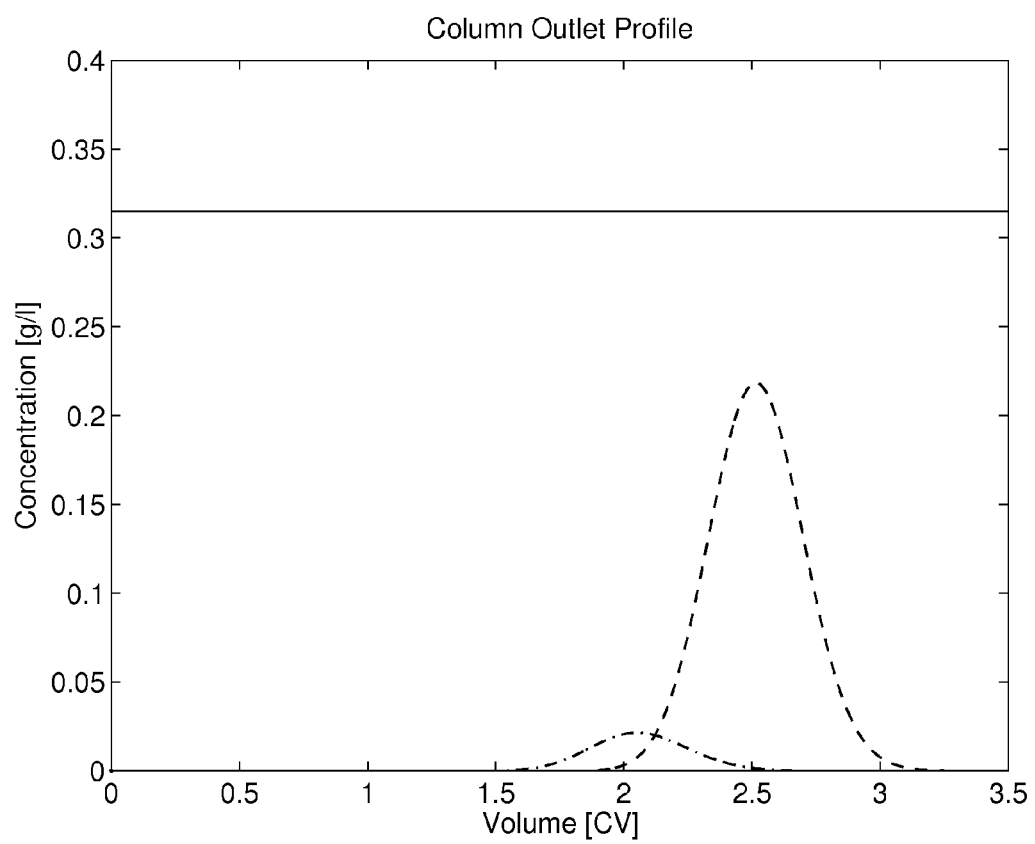

Mollerup, Fluid Phase Equilibria, 2006, vol. 241, No. 1-2, pp. 205-215.
Mollerup et al., Journal of Chromatography, 2008, vol. 1177, No. 2, pp. 200-206.
Guiochon G. et. al., "Fundementals of Preparative and Nonlinear Chromatography, Second Edition", Elsevier (2006).
Wekenborg K. et. al., "Nicht-isokratische TMS-Trennung von Proteinen mittels Ionenaustauschchromatographie", Chemie Ingenieur Technik 76 (2006) pp. 815-819.
Abel S. ,Marco Mazzotti, M. Morbidelli, "Solvent gradient operation of simulated moving beds, I Linear isotherms", J Chrom. A, 944 (2002) 23-39.
Abel S., M. U. Babler, C. Arpagaus, M Mazzotti, J. Stadler, "Two-fraction and three fraction continuous simulated moving bed separation of nucleosides", J. Chrom. A, 1043 (2004) 201-210.
Antos C., A. Seidel-Morgenstern, "Application of gradient in the simulated moving bed process", Chemical Engineering Science 56 (2001) 6667-6682.
Brooks C. A., S. M. Cramer, "Steric Mass-Action Ion Exchange: Displacement Profiles and Induced Salt Gradients", AIChE J. 38 (1992) 1969-1978.
Jeansonne Mark S., Joe P. Foley, "Review of the Exponentially Modified Gaussian (EMG) Function since 1983", Journal of Chromatographic Science, 29 (1991), pp. 258-266.
Ma Z., N.-H.-L. Wang, "Standing Wave Analysis of SMB Chromatography: Linear Systems", AlChE Journal 43 (1997) pp. 2488-2508.
Ruthven D.M., C.B. Ching, "Counter-current and Simulated Counter-Current Adsorption", Chem. Eng. Sci. 44 (1989), pp. 1011-1038.
Schulte M., L. Britsch, J. Strube, "Continuous Preparative Liquid Chromatography in the Downstream Processing of Biotechnological", Acta Biotechnology 20 (2000) pp. 3-15.
Storti G., M. Masi, S. Carra, M. Morbidelli, "Optimal Design of Multicomponent Countercurrent Adsorption Separation Processes Involving Nonlinear Equilibria", Chem. Eng. Sci, 44, (1989) pp. 1329-1345.
Wekenborg K. et. al., "Nicht-isokratische TMS-Trennung von Proteinen mittels Ionenaustauschchromatographie", Chemie Ingenieur Technik 76 (2006) pp. 815-819.
Gottschlich, et al. J Chromo. A, vol. 765: 201 (1997).
Mun, et al. Biotechnol Prog vol. 18: 1332 (2002).

* cited by examiner

COUNTER CURRENT PURIFICATION OF POLYPEPTIDES

CROSS-REFERENCE TO RELATED APPLICATIONS

This application is a 35 U.S.C. §371 national stage application of International Patent Application PCT/EP2009/066630 (published as WO 2010/066734 A1), filed Dec. 8, 2009, which claimed priority of European Patent Application 08170945.3, filed Dec. 8, 2008, and European Patent Application 08172730.7, filed Dec. 23, 2008; this application further claims priority under 35 U.S.C. §119 of U.S. Provisional Application 61/121,741, filed Dec. 11, 2008.

FIELD OF THE INVENTION

The present invention relates to methods for the purification of proteins or peptides using counter current chromatography. In particular the present invention relates to the use of counter current chromatography for the purification of proteins or peptides including synthetic, semi-recombinant or recombinant polypeptides, such as recombinant GLP-1.

BACKGROUND OF THE INVENTION

In accordance with 37 C.F.R. §1.52(e)(5), Applicants enclose herewith the Sequence Listing for the above-captioned application entitled "SEQUENCE LISTING", created on May 18, 2011. The Sequence Listing is made up of 5,153 bytes, and the information contained in the attached "SEQUENCE LISTING" is identical to the information in the specification as originally filed. No new matter is added.

Counter Current purification systems are purification systems where the solid phase moves against the current of the fluid stream either physically or is simulated to make this movement counter current relative to the fluid stream by the change in positioning of different separation beds of the system. Counter Current purification systems include e.g. Simulated Moving Bed chromatography (SMB) and Multi-column Counter Current Solvent Gradient Purification (MC-SGP).

Simulated moving bed chromatography (SMB) was first described in U.S. Pat. No. 2,985,589. The specification discloses a separation tower divided into a number of individual interconnected separation beds containing solid phase chromatography sorbent. An inline pump at the bottom of the tower connects flow from the bottom to the top, thereby providing a continuous loop. Inlet ports for Feedstock (F) and Desorbent (D) and exit ports for Raffinate (R) and Extract (E) are placed at specific points in the series of separation beds. At defined intervals, the position of the beds is switched in the opposite direction from the flow, producing a counter current movement of the solid phase beds relative to the fluid streams. Feedstock (F) introduced into the first bed begins to separate into the various components contained therein, with the less retained species migrating in the direction of fluid flow and being collected at the Raffinate port. The more retained species remain preferentially associated with the solid phase and are collected at the Extract port. By regulating the switch times and flow rates of F, D, R, and E, a cyclic steady state is established, allowing for continuous flow of purified products from the system.

More recently SMB has been applied to separate sugar isomers, hydrocarbons, solvents, and other industrial applications. Many of these industrial devices, like the original '589 device, employ variations of mechanical rotary valves in effecting column switching. The valve components are arranged so that at any given valve position, multiple inlet and outlet flows are directed to predetermined columns, and advanced one position correspondingly with each rotational step. Such rotary valves are disclosed in U.S. Pat. Nos. 6,719,001, 4,574,840, and 4,614,205. To emphasize the intended scale of some of these devices, refer to U.S. Pat. No. 3,040,777 which describes a valve occupying an area of 64 sq. feet and weighing 10 tons.

Other SMB systems are disclosed in U.S. Pat. No. 4,434,051 and U.S. Pat. No. 5,635,072. Another patent, U.S. Pat. No. 6,544,413, discloses a plural valve device having clustered valve assemblies of four valves for control of inputs/outputs proximately to each chromatographic bed. It has the advantage of reducing the volume of liquid for small scale SMB systems. U.S. Pat. No. 6,979,402 discloses a device in which cross-over conduits are replaced entirely by connecting channels machined into the top and bottom plates of the rotary valve body and aligned with column ports to create an SMB fluid loop, thus reducing the void volume.

Several recent applications of SMB to the purification of pharmaceutically active diastereomers and enantiomers have been disclosed in U.S. Pat. Nos. 6,462,221, 6,461,858, 6,458,995, and 6,455,736. The use of new chiral resins in SMB for binary separations of such molecules is becoming commonplace. SMB is also considered for purification of biomolecules from complex mixtures. For example, the purification of monoclonal antibodies using SMB has been reported by Gottschlich et al. (J. Chromatogr. A, 765 (1997) 201) and disclosed in WO 2004/024284. SMB purification has previously been published for insulin purification, as disclosed in WO 2001/087924.

WO 2008/048395 discloses small-scale simulated moving bed chromatography.

Glucagon Like Peptides-1 (GLP-1) is a hormone that is released when the blood sugar level is low. GLP-1 increases the insulin production and thereby reduces the blood sugar level. GLP-1 and GLP-1 analogues are used in the treatment of type II diabetes.

There is still a need for a purification system for purifying a fluid mixtures comprising one or more impurities and a protein or peptide of interest such as a GLP-1 peptide, where the concentration of the impurities is much smaller than the concentration of the protein or peptide of interest.

OBJECT OF THE INVENTION

It is an object of the invention to provide improved methods for the purification of polypeptides including synthetically, semi-recombinantly or recombinantly produced polypeptides, such as recombinant GLP-1. Counter current purification systems, such as SMB have been shown by the inventors of the present invention to be particularly suitable for the purification of recombinant proteins and in particular GLP-1.

SUMMARY OF THE INVENTION

It has been found by the inventors that counter current chromatography is particularly suitable for the purification of proteins or peptides including synthetically, semi-recombinantly or recombinantly produced proteins or peptides, such as GLP-1 peptides. There is an increasingly demand from the public and from drug approval authorities for even more pure and homogenous preparations of therapeutic proteins. Also the cost has to be low. Accordingly production costs are an issue that have to be optimized in an industrial process in order to meet these expectations.

So, in a first broad aspect the present invention relates to methods for the purification of peptides, polypeptides or proteins by counter current chromatography.

In another aspect the present invention relates to a method for the chromatographic separation of a polypeptide of interest from at least one further component in a fluid mixture, the method comprising
  a) Providing a counter current purification system that comprises a plurality of sections in fluid connection, said sections comprising at least one solid phase and a first desorbent stream;
  b) introducing said fluid mixture as the feed stream into said counter current purification system wherein the fluid mixture contacts the solid phase in a counter current mode;
  c) controlling the isotherm by adjusting the concentration of at least one modifier in the feed stream so that the initial slope of the isotherm, A, is about parallel with the slope of the operating line when a plot is made of $m^{III}$ & A as a function of $Q^F$ or $\alpha$;
  d) effecting separation of the polypeptide of interest from at least one further component; and
  e) collecting the polypeptide of interest to provide a purified composition thereof.

LEGENDS TO THE FIGURE

FIG. 1: Chromatogram with product (- - -) and impurity (-•-•). As seen in the figure there is a large overlap between the two peaks. A compromise must be made. Product collection from 2 CV will give a large yield, but low purity, whereas product collection from 2.5 CV will give a high purity but a low yield.

Figure 2:
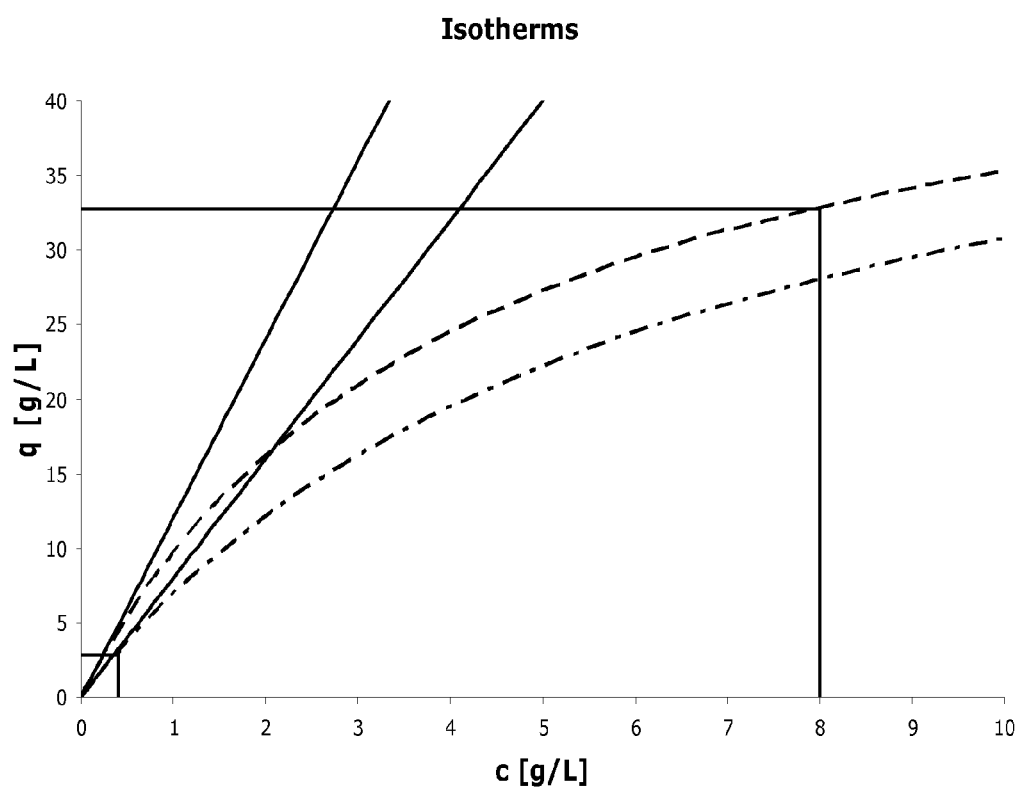

FIG. 2: Isotherms of the pure weakly bound component (-•-•-), the pure strongly bound component (- - -) and the initial slopes of the two isotherms. If a stream contains 8 g/L of the strong component (the product) and the weakly bound impurity is 5% of this, it corresponds to 0.4 g/L. The figure shows that the initial slope is a reasonable approximation for the isotherm of the impurity at low concentrations, whereas this is not the case for the stronger bound component.

Figure 3:
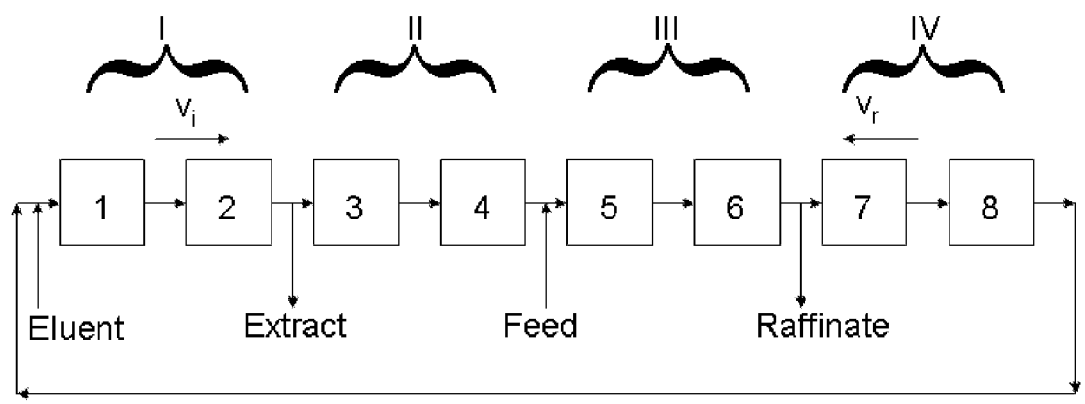

FIG. 3: SMB-plant with recycle. The SMB consists of four sections I-IV each with two columns. The section after the desorbent pump is named section I. The outlet from section IV is recycled to section I. The liquid flow is to the right and the column movement is to the left.

Figure 4:
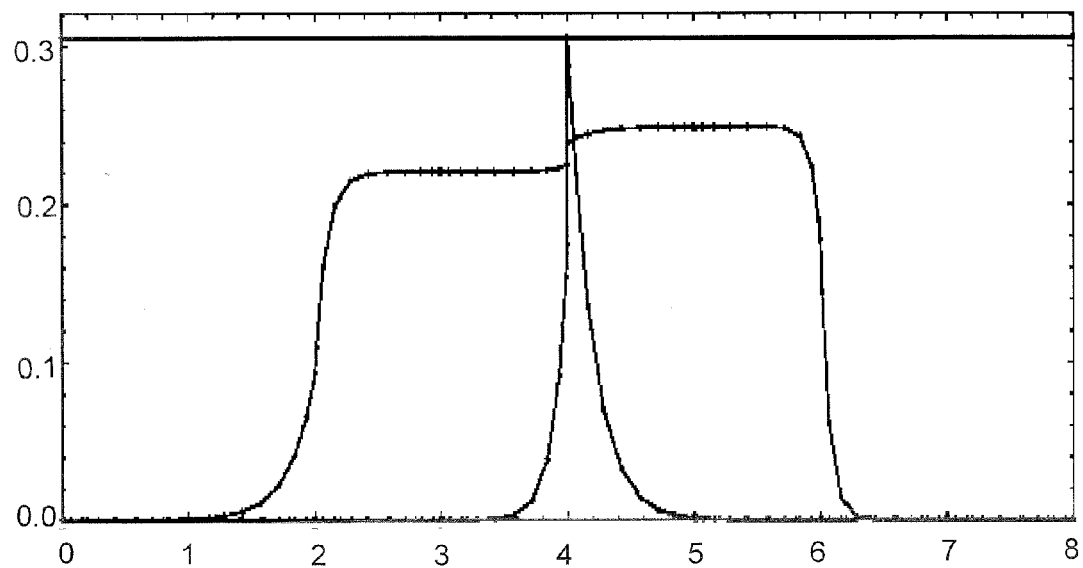

FIG. 4: Steady state concentration profiles in a True Moving Bed (TMB). The stronger bound component moves in the direction of the resin to the extract port, and the weaker bound component moves with the eluent to the raffinate port. All streams enter and exit the TMB as shown in FIG. 3.

Figure 5:
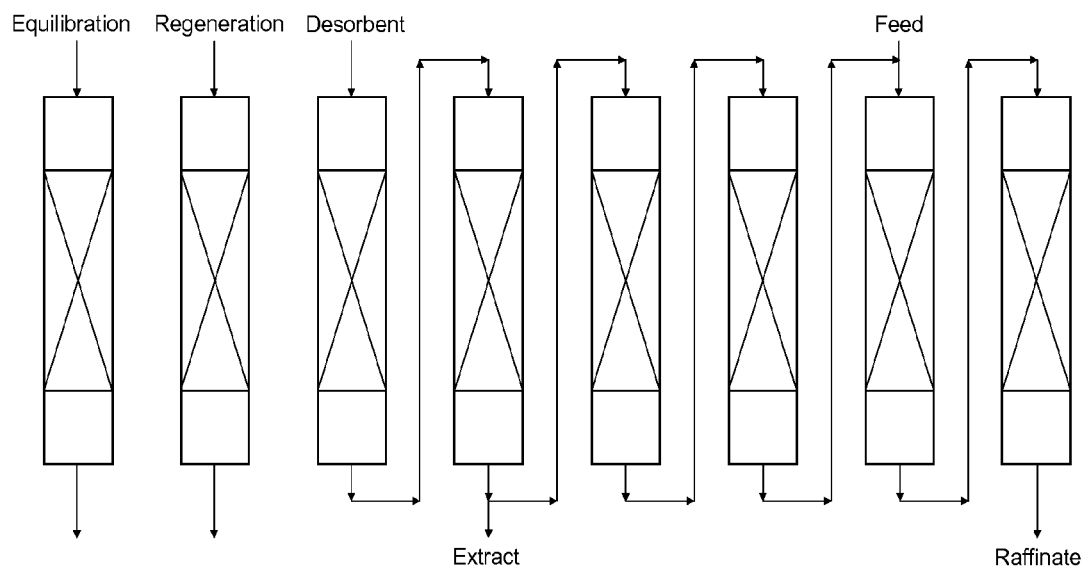

FIG. 5: Layout of an open loop SMB-plant with eight columns, regeneration and equilibration. The columns can be regenerated and equilibrated in the SMB-plant (Abel 2004). Since the raffinate stream only contains weakly bound components, the outlet from section III can as an alternative be used as inlet to the equilibration column.

Figure 6:
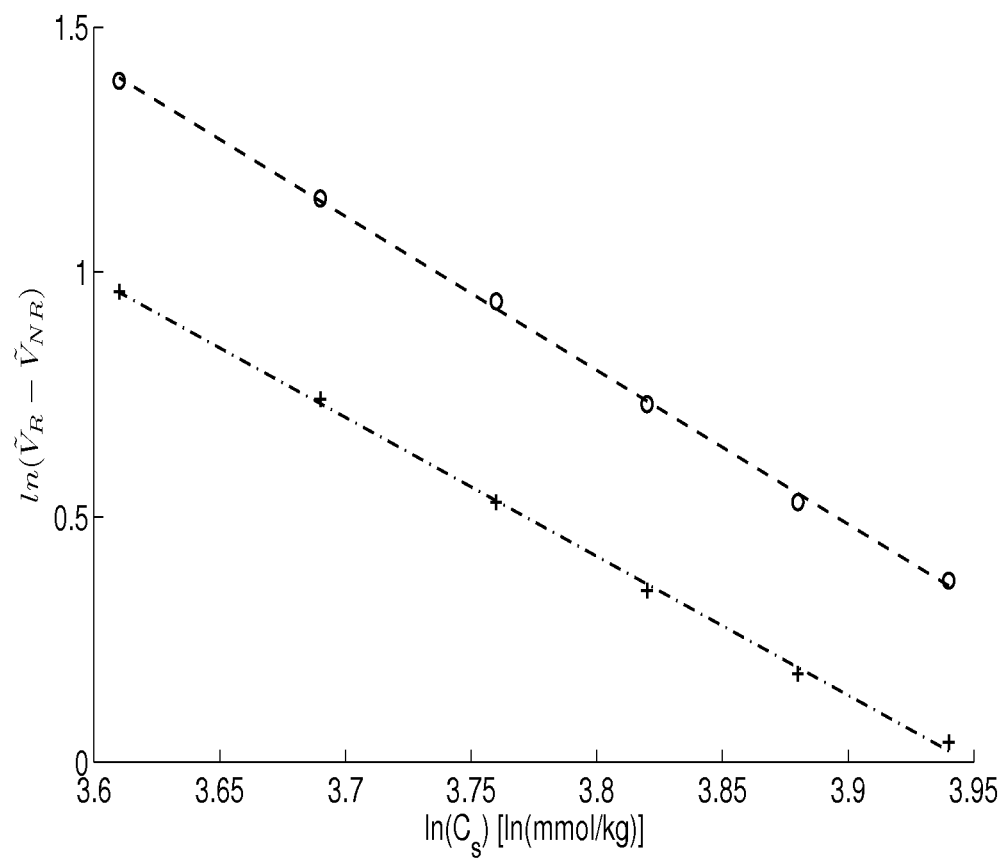

FIG. 6: Salt dependency of a linear isotherm in Ion Exchange Chromatography (IEX). The theoretical retention will be a straight line in a double logarithmic plot of $V_R$–$V_{NR}$ as a function of $\ln(C_s)$. Experimental data for the weaker bound component is shown by (+) and the stronger bound component (o). The fitted lines to the experimental data are (-•-•-) for the weaker bound and (- - -) for the stronger bound components.

Figure 7:
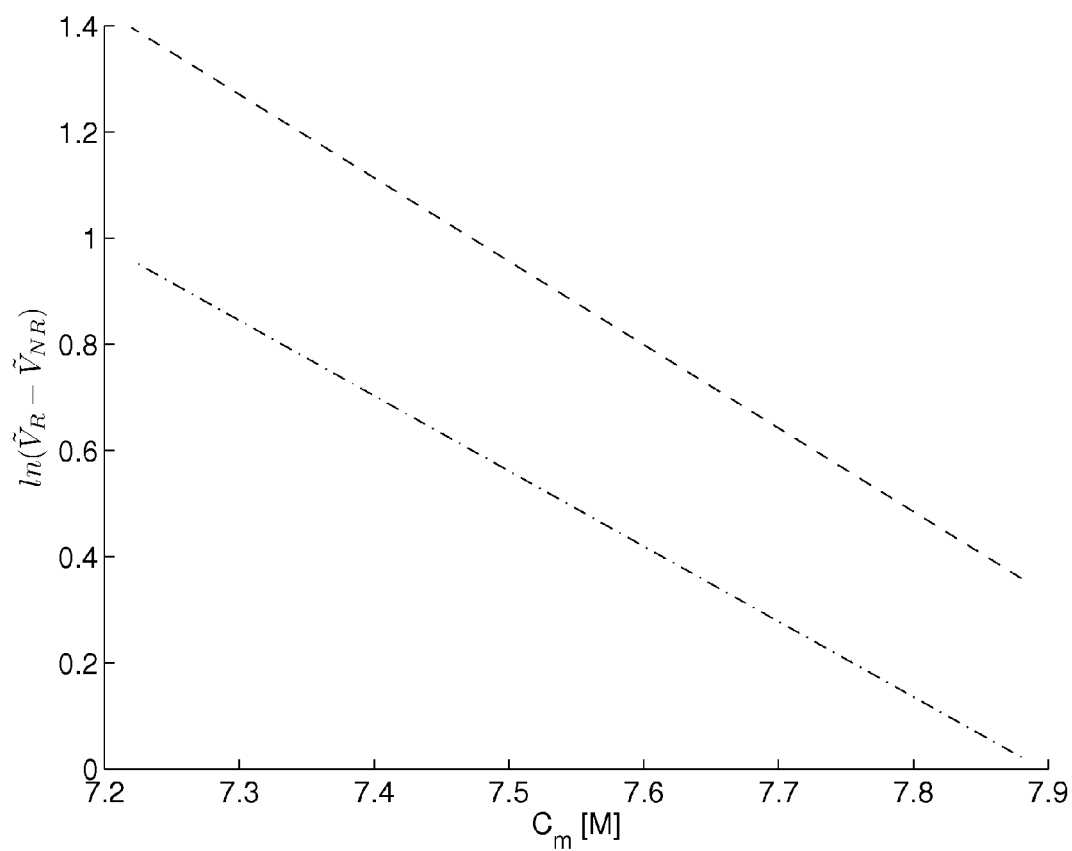

FIG. 7: EtOH dependency of a linear isotherm in Reverse Phase Chromatography (RP). The theoretical retention will be a straight line in a semilogarithmic plot of $V_R$–$V_{NR}$ as a function of concentration of the organic phase, $c_m$. The weaker bound component is (-•-•-) and the stronger bound component is (- - -).

Figure 8:
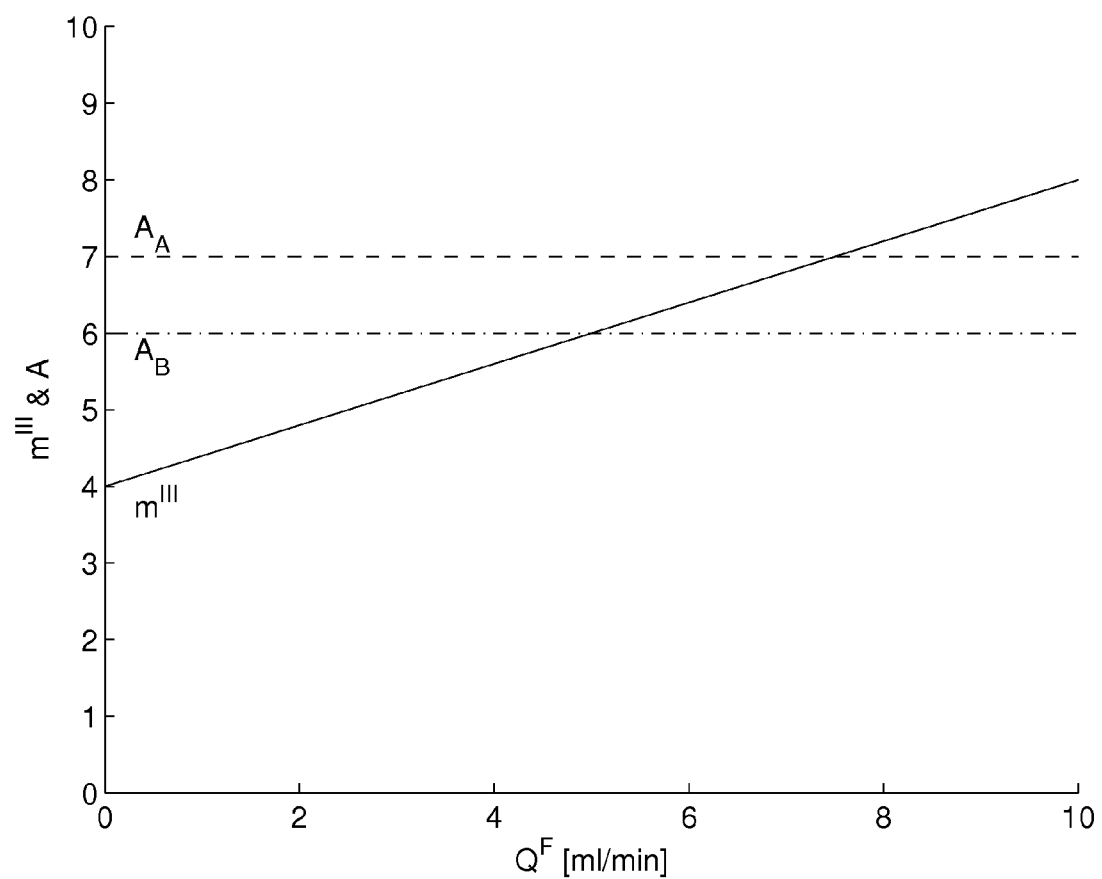

FIG. 8: Isocratic solution. The adsorption of the stronger bound component, $A_A$, and the weaker bound component, $A_B$, together with the dimensionless flow rate in section III, $m^{III}$. In the isocratic solution the concentration of the modifier in the feed stream will be identical to the concentration in section II. Consequently the concentration in section III will be identical to these and will not depend on the feed flow (horizontal lines). The initial slope of the isotherms of the weaker and stronger bound component will therefore be constant. Therefore only feed flows between 5 and 7.5 will fulfil the requirement of retaining the stronger bound component and elution of the weaker bound component.

Figure 9:
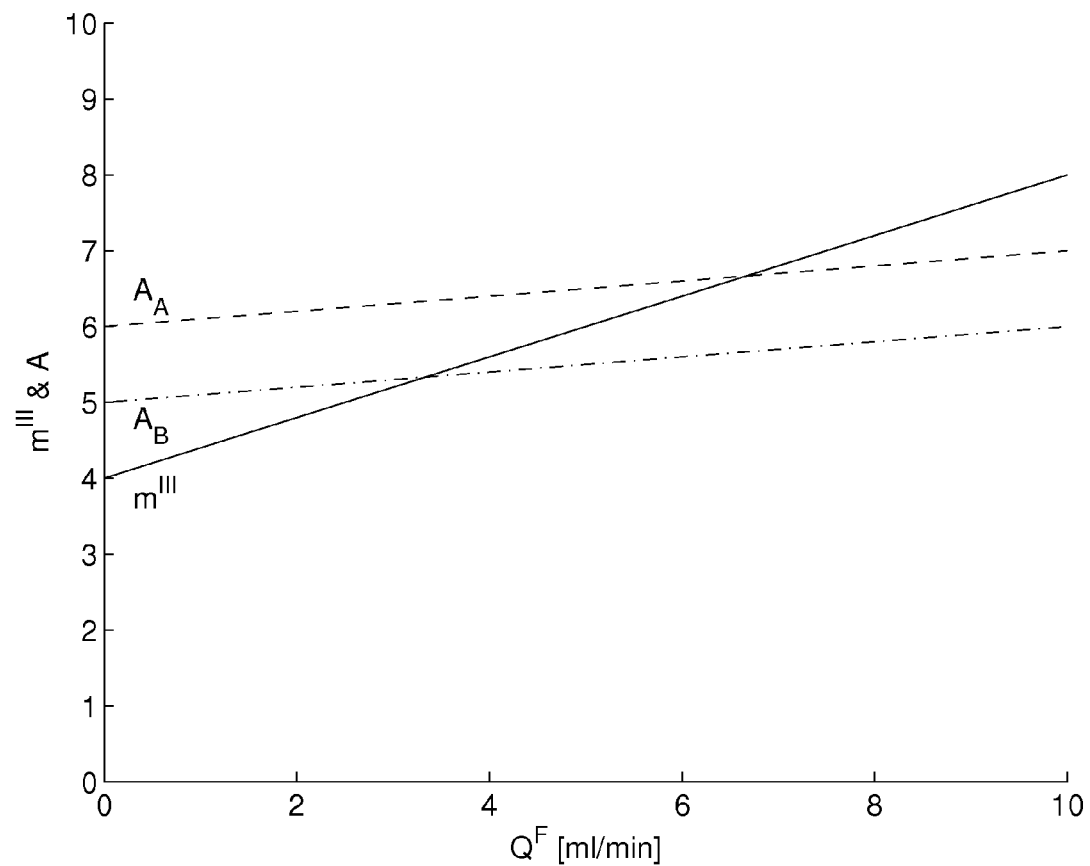

FIG. 9: Gradient solution. Using a gradient in the SMB-plant will lead to a change in the initial slope of the isotherm, depending on the concentration of the modifier concentration (no longer horizontal lines, see FIG. 8). However using a gradient will not always ensure that the dimensionless flow rate of the modifier, $m^{III}$, will lie between the initial slope of the weaker and stronger bound component.

Figure 10:
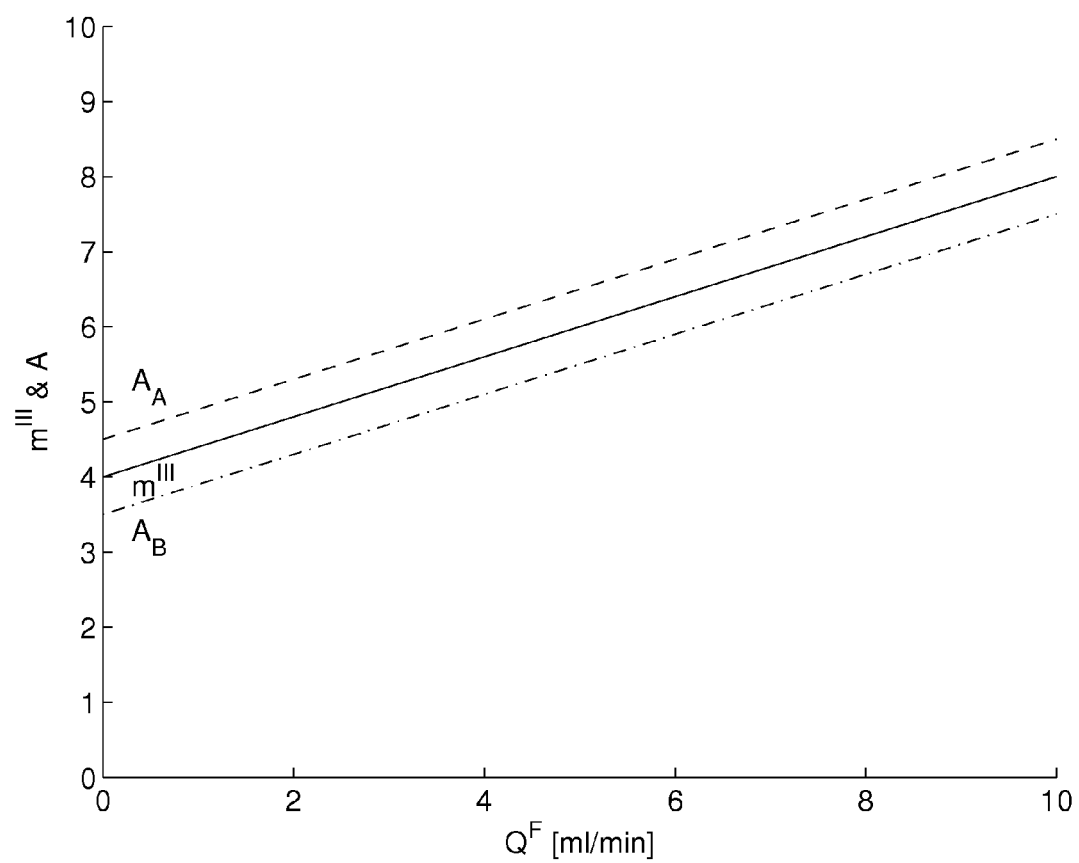

FIG. 10: Attractive combination of modifier concentration in feed and eluent. It is seen that for all feed flows the operating line $m^{III}$ lies between the initial slope of the weaker and the stronger bound components.

Figure 11:
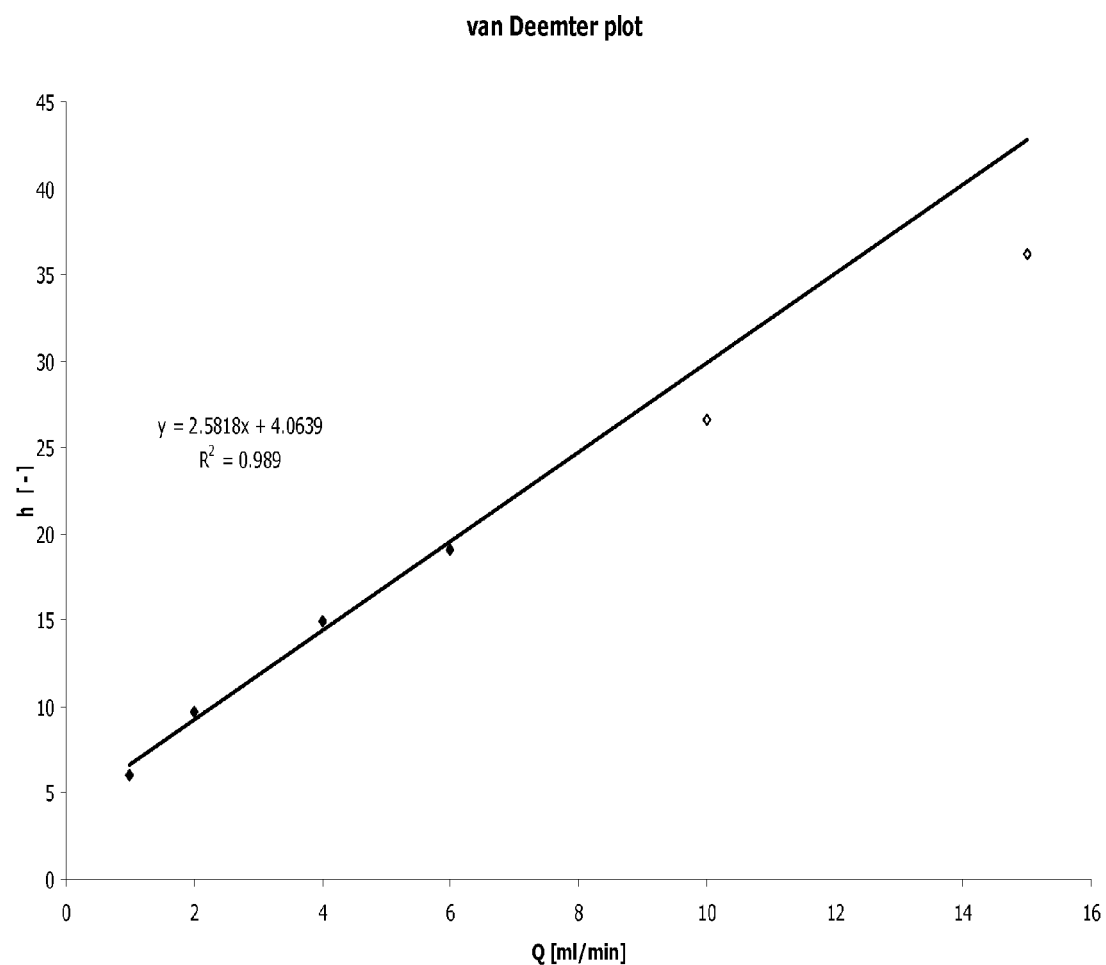

FIG. 11: van Deemter plot of pulse experiments. The van Deemter plot shows the reduced plate height as a function of the flow rate.

Figure 12:
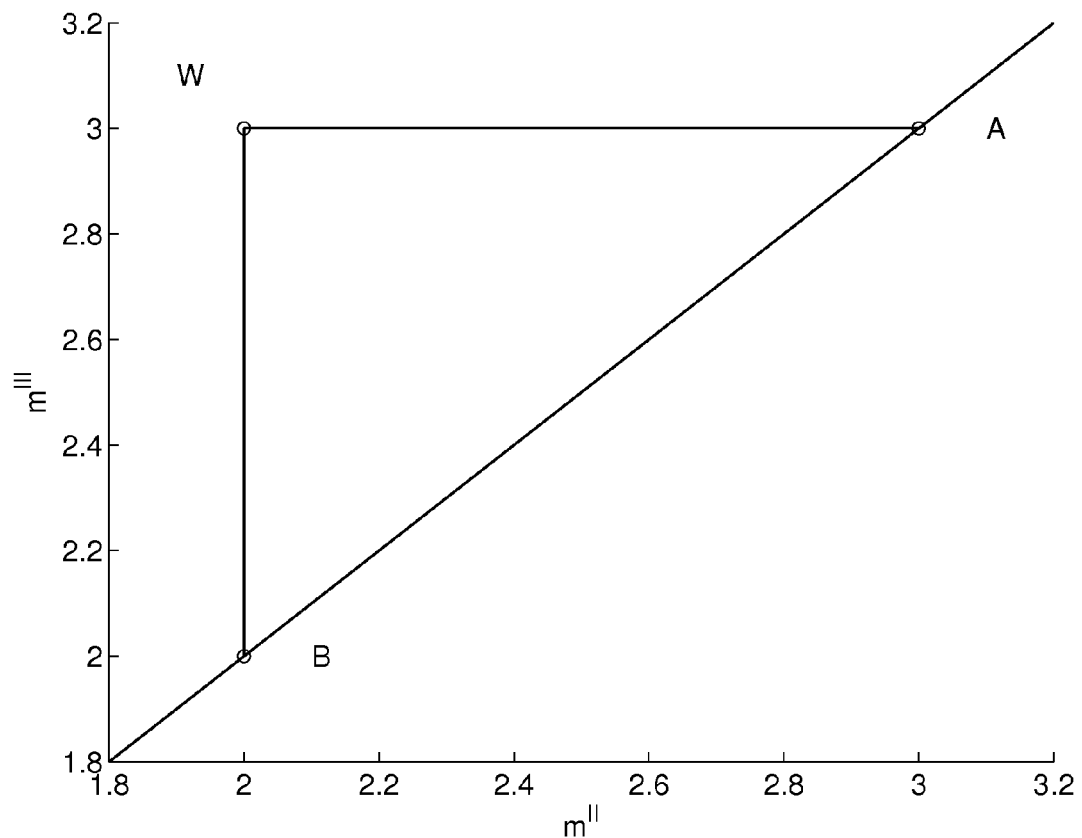

FIG. 12: Complete separation region for a linear isotherm. The optimal operating point is at the minimum value of $m^{II}$ and the maximum value of $m^{III}$, corresponding to the point W.

Figure 13:
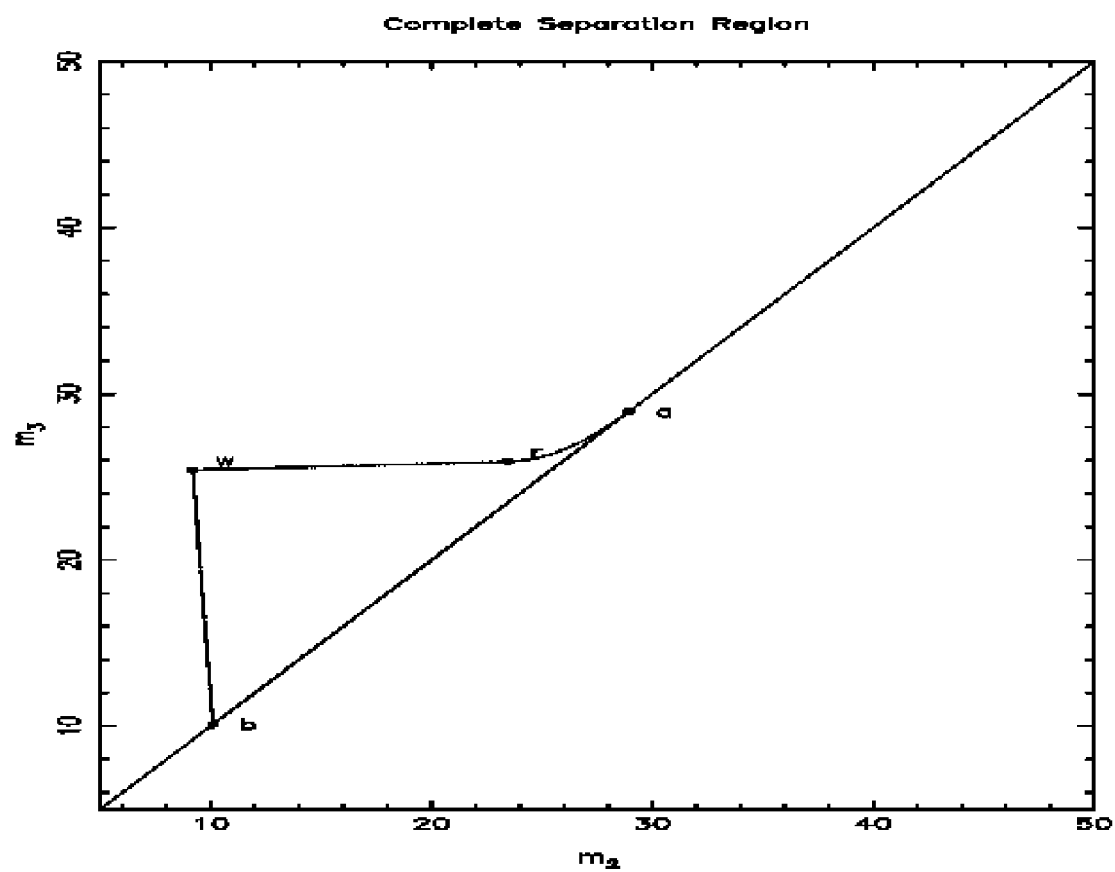

FIG. 13: Complete separation region for a non-linear isotherm under isocratic conditions. The point W moves downward and the productivity is reduced in the plant.

Figure 14:
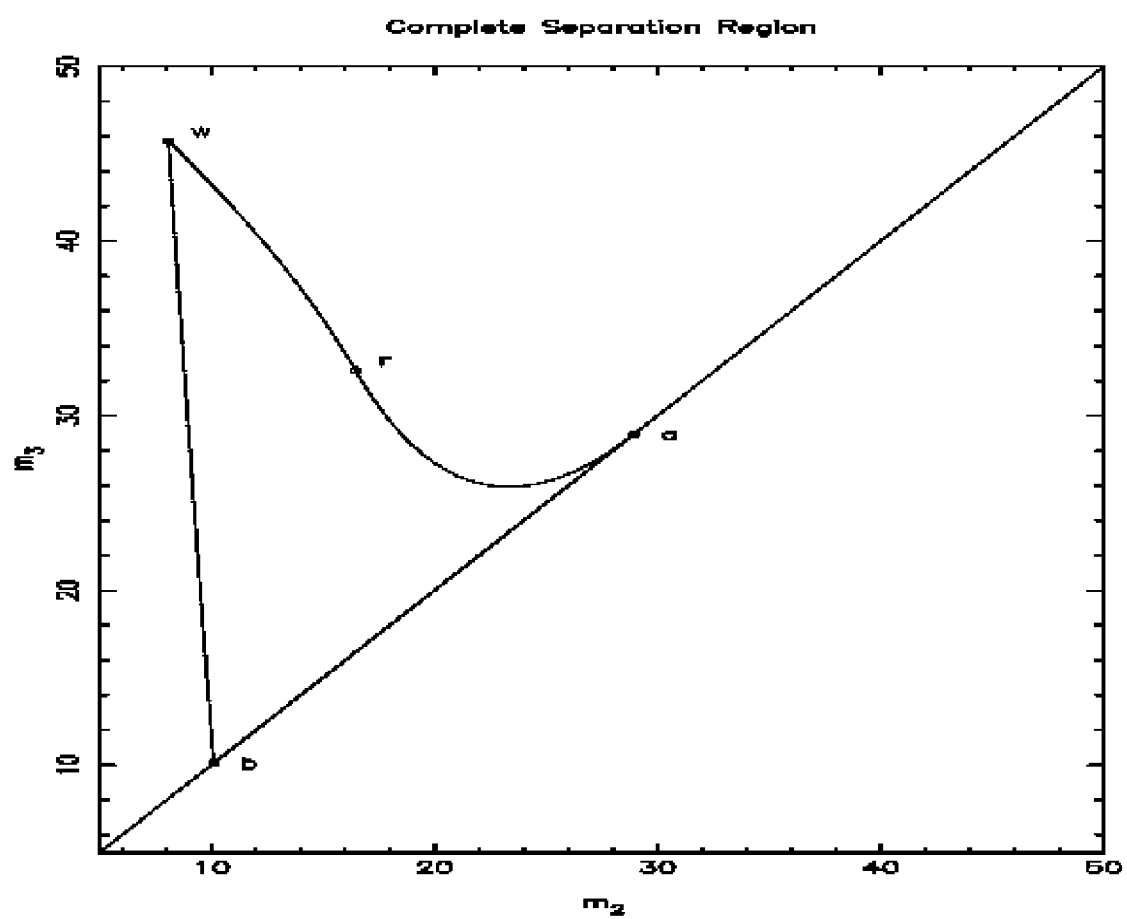

FIG. 14: Complete separation region with a gradient in salt/organic solvent and pH. It is seen that the optimal operating point, W, moves upward due to the gradient. This allows a higher feed flow, and hence a higher productivity.

Figure 15:
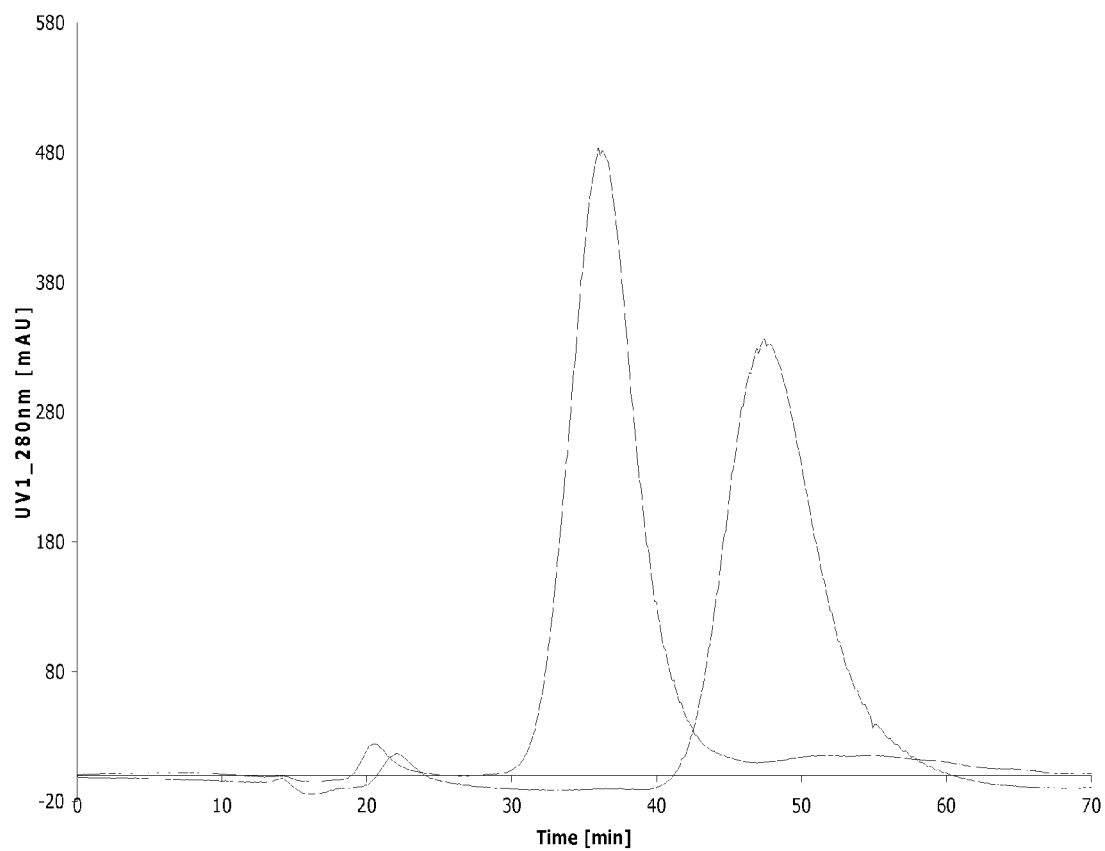

FIG. 15: Test of desorbent I and desorbent II, see also FIG. 18, for SMB-experiment II. The retention volumes can be calculated from a fit to the EMG-function. A description of the Exponentially Modified Gaussian (EMG) Function can be found in Jeansonne (1991).

Figure 16:
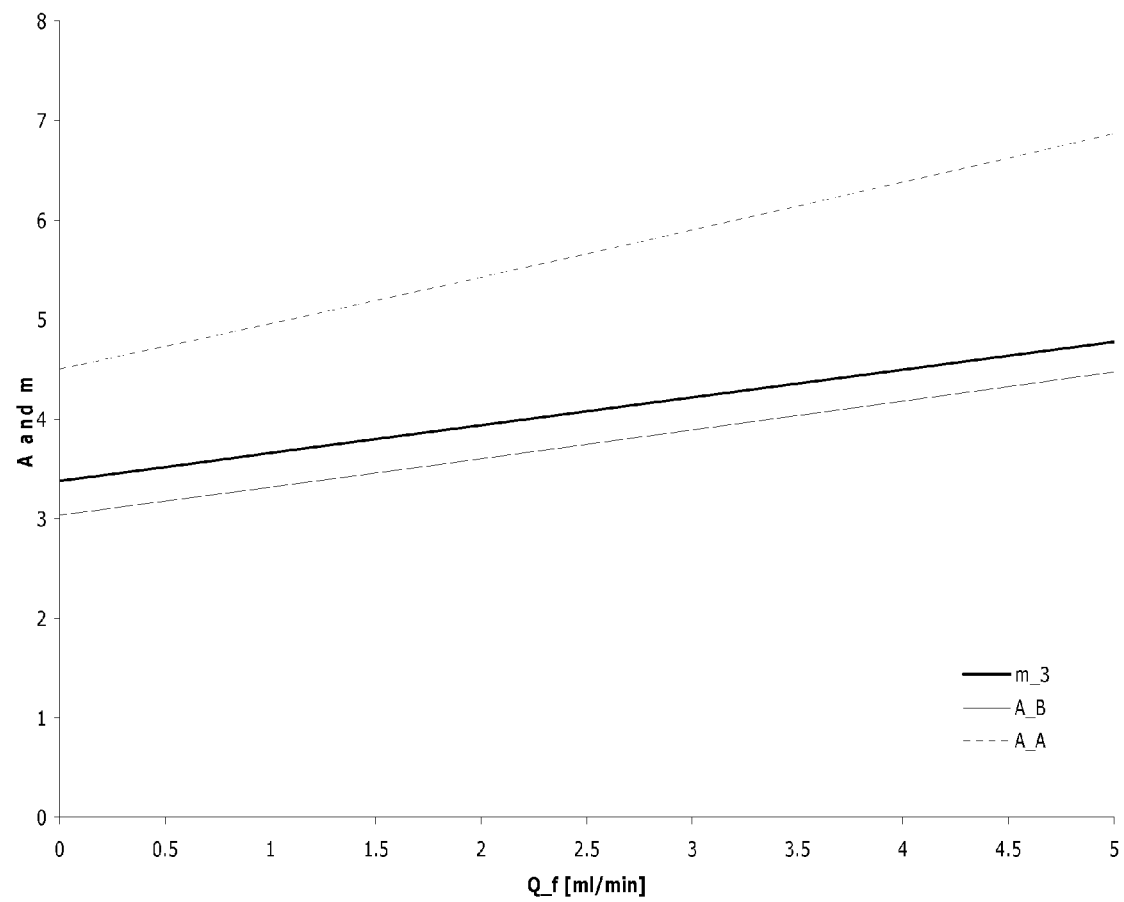

FIG. 16: Calculated initial slope of the isotherm, A, and dimensionless flow in section III, m, with optimal salt concentration in the feed flow. The dimensionless flow has the same slope as the slope of the weaker bound component, $A_B$.

Figure 17:
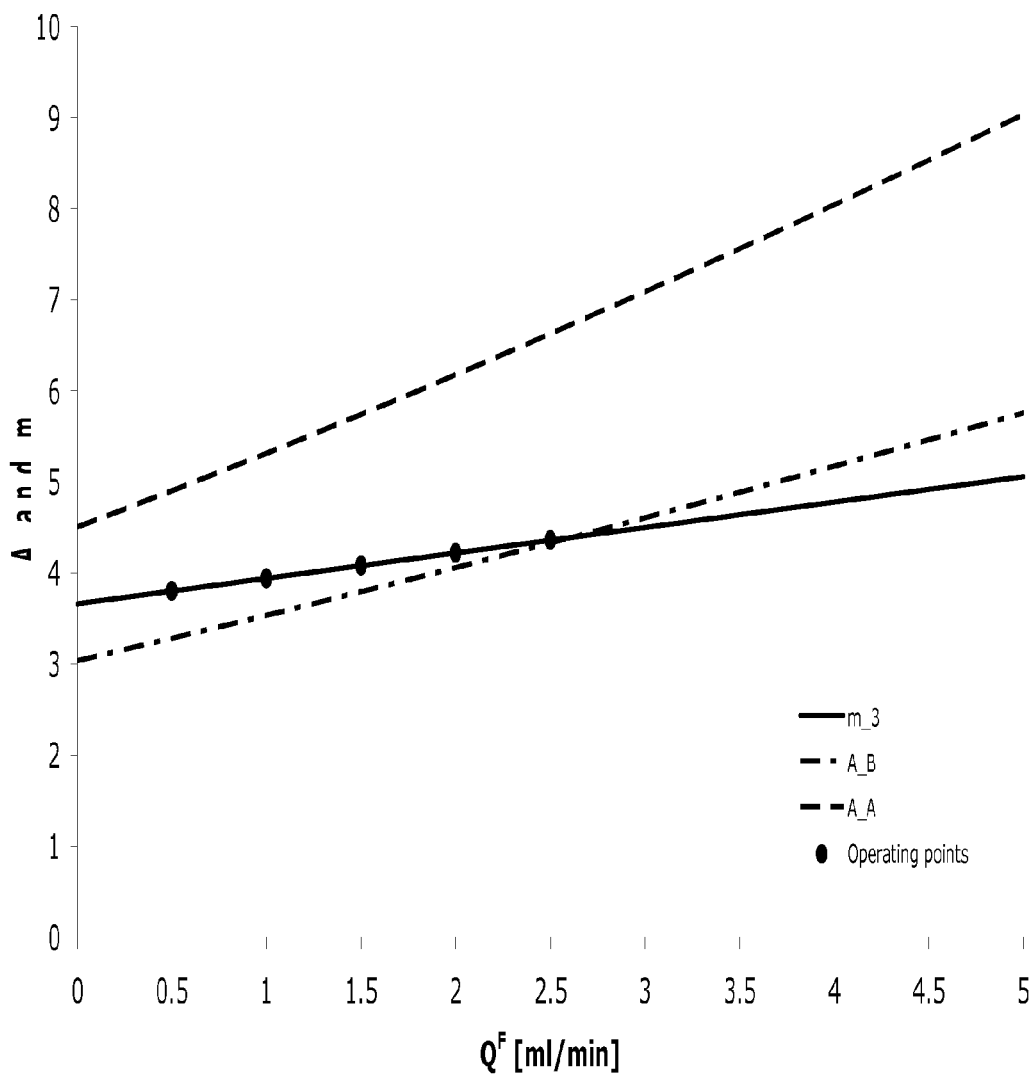

FIG. 17: Calculated initial slope of the isotherm, A, and dimensionless flow in section III, m, with the actual salt concentration in the feed flow. The dimensionless flow has a slope lower than the slope of the weaker bound component, $A_B$.

Figure 18:
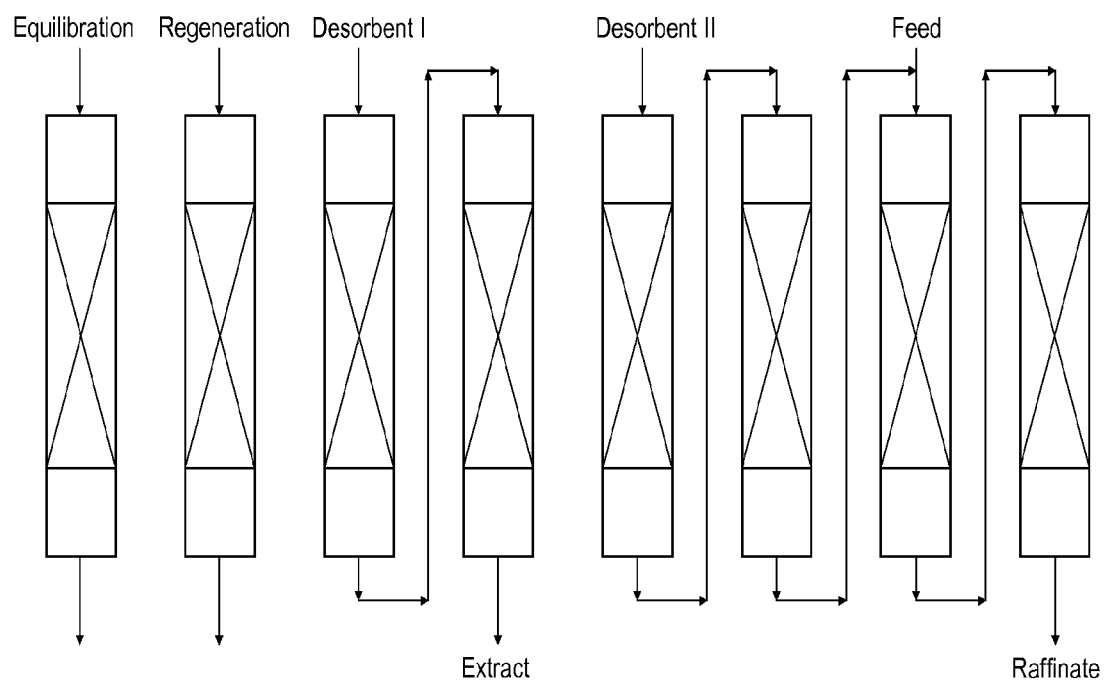

FIG. 18: Setup of plant for SMB-experiment no II. The connection between section I and section II was cut to be able to use two different salt concentrations in the two sections (see also FIG. 5 for comparison).

Figure 19:
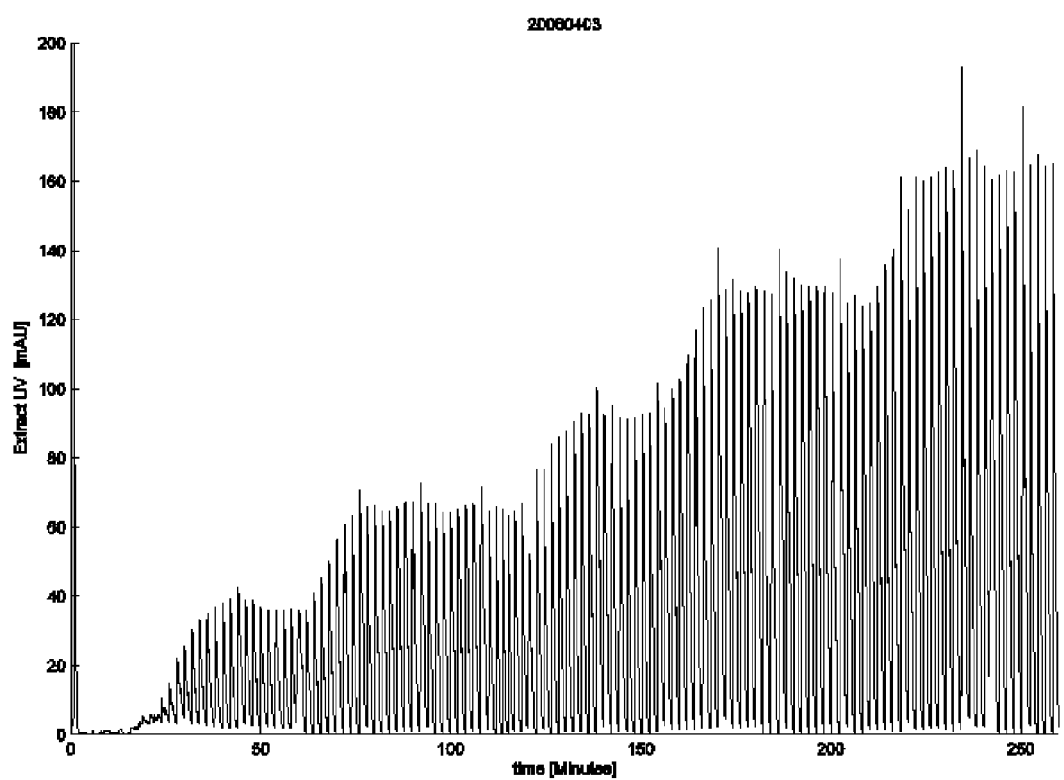

FIG. 19: Extract stream UV-signal from experiment II. The feed flow was initially set to ½ ml/min until a cyclic steady state was reached. A sample was taken for analysis and the flow increased by ½ ml/min and a new cyclic steady state was reached.

Figure 20:
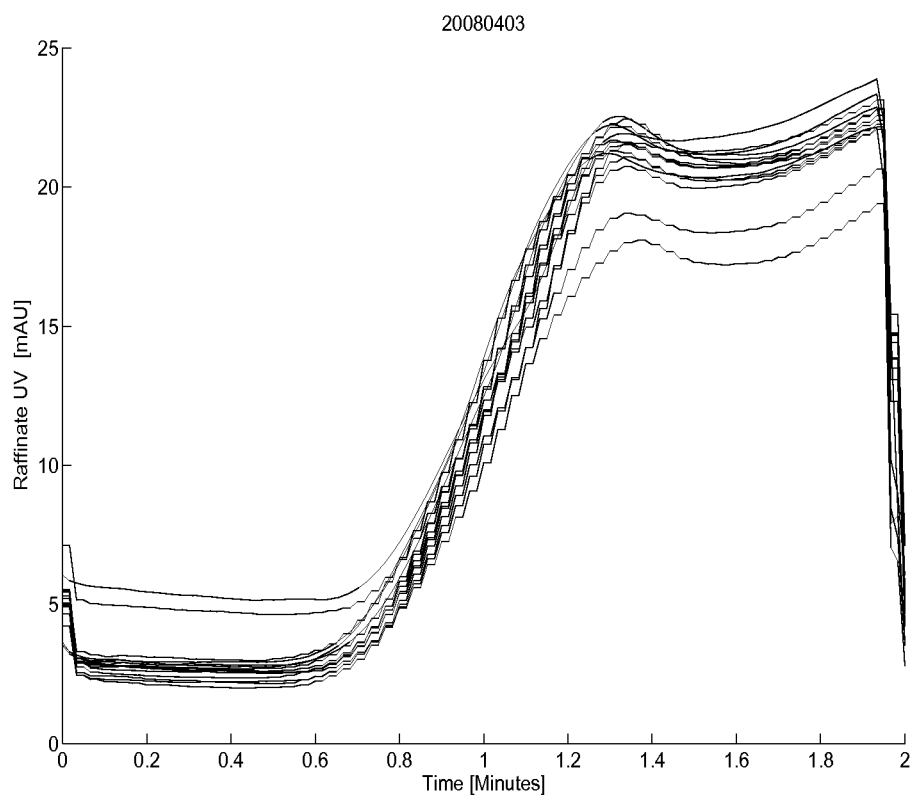

FIG. 20: The raffinate port UV-signal from experiment II at a feed flow of 2 ml/min and after a cyclic steady state is obtained. The columns are moved into zone II after having passed the regeneration and equilibration zone, therefore the UV-signal is initially zero. The UV-signal increases when the components are eluted. A plateau is seen before the UV-signal starts to increase again.

Figure 21:
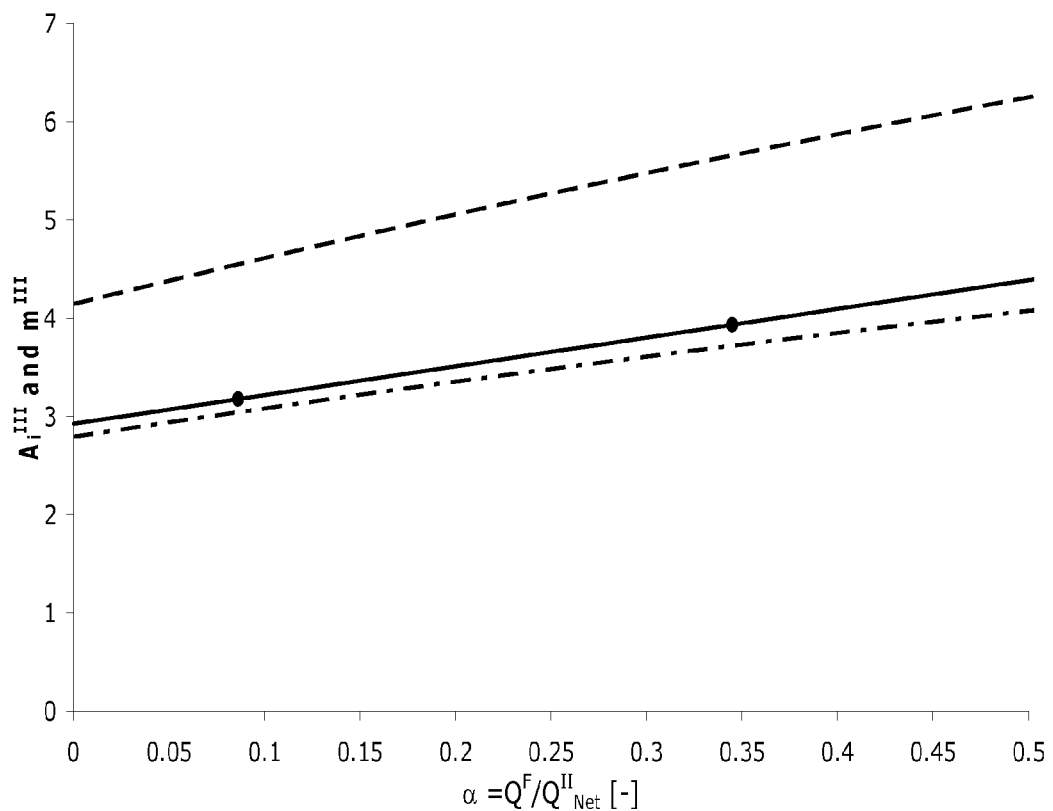

FIG. 21: Calculated initial slope, A, for the weak (-•-•-) and strong bound (- - -) components in zone III together with the operating line (—) and the operating points (black dots), from experiment III. It is seen that the operating line has approximately the same slope as the initial slope of the isotherm at infinite dilution for the weaker bound component.

Figure 22:
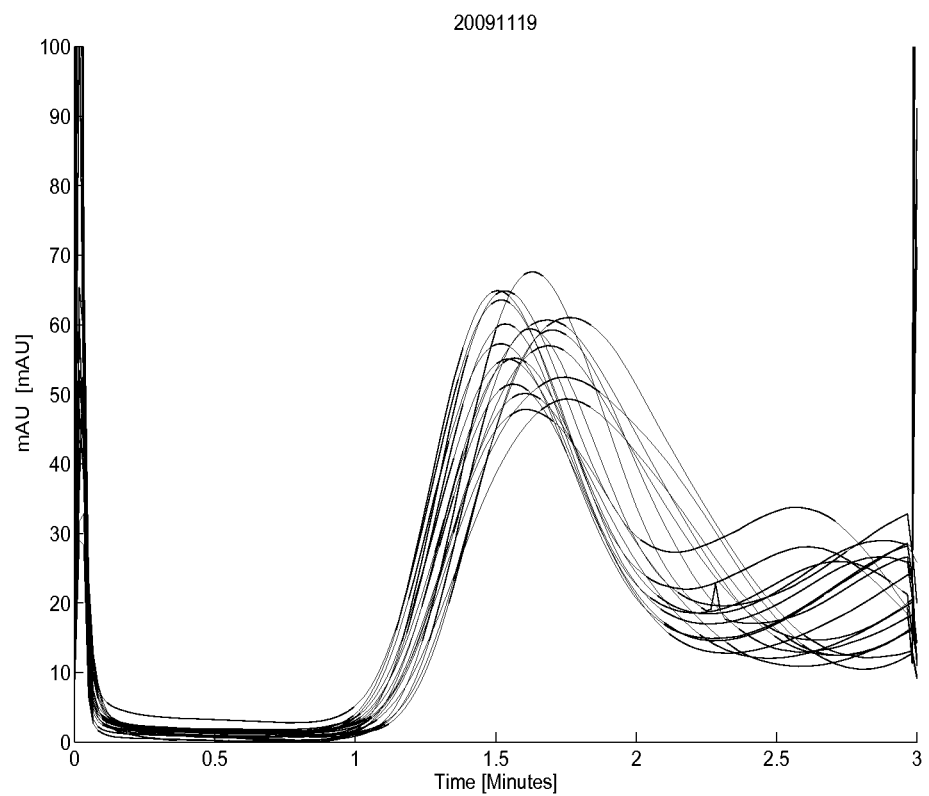

FIG. 22: The raffinate port UV-signal from experiment III at a feed flow of 2 ml/min and after a cyclic steady state is obtained. The columns are moved into zone II after having passed the regeneration and equilibration zone, therefore the UV-signal is initially zero. The UV-signal increases when the components are eluted. A very distinct peak is seen compared to FIG. 20.

Figure 23:
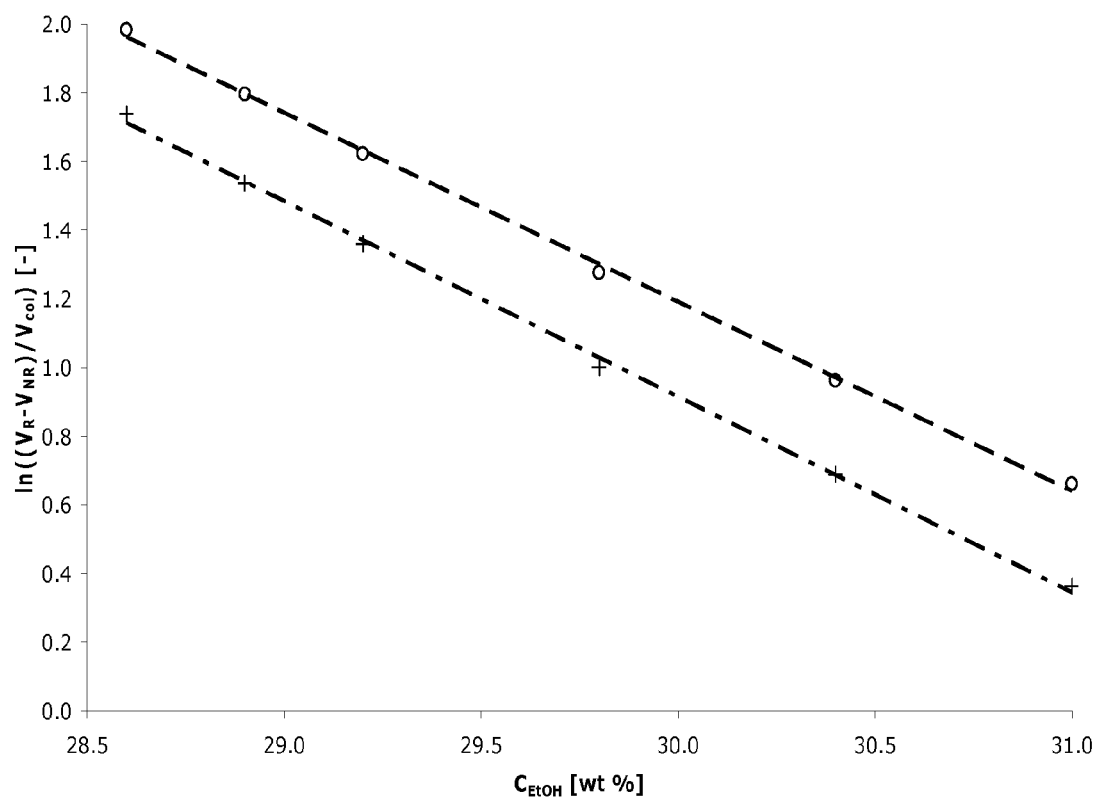

FIG. 23: Measured ethanol dependency for the weaker bound component (+) and stronger bound component (o) of the linear isotherm in Reversed Phase Chromatography (RP), together with a fit to experiments. The theoretical retention will be a straight line in a semi logarithmic plot of $V_R - V_{NR}$ as a function of $C_{EtOH}$.

Figure 24:
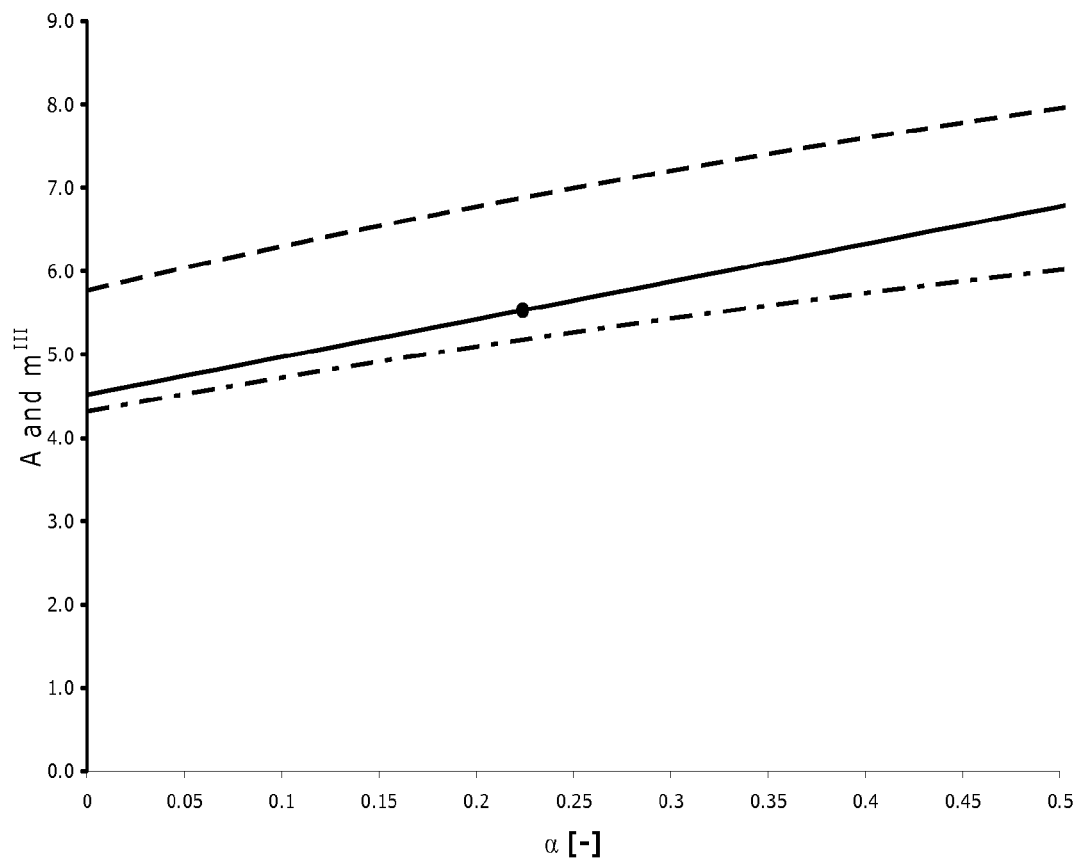

FIG. 24: Calculated initial slope, A, for the weaker (-•-•-) and stronger bound (- - -) components in zone III together with the operating line (—) and the operating point (black dot). It is seen that the operating line has approximately the same slope as the change in the isotherms initial slope at infinite dilution.

Figure 25:
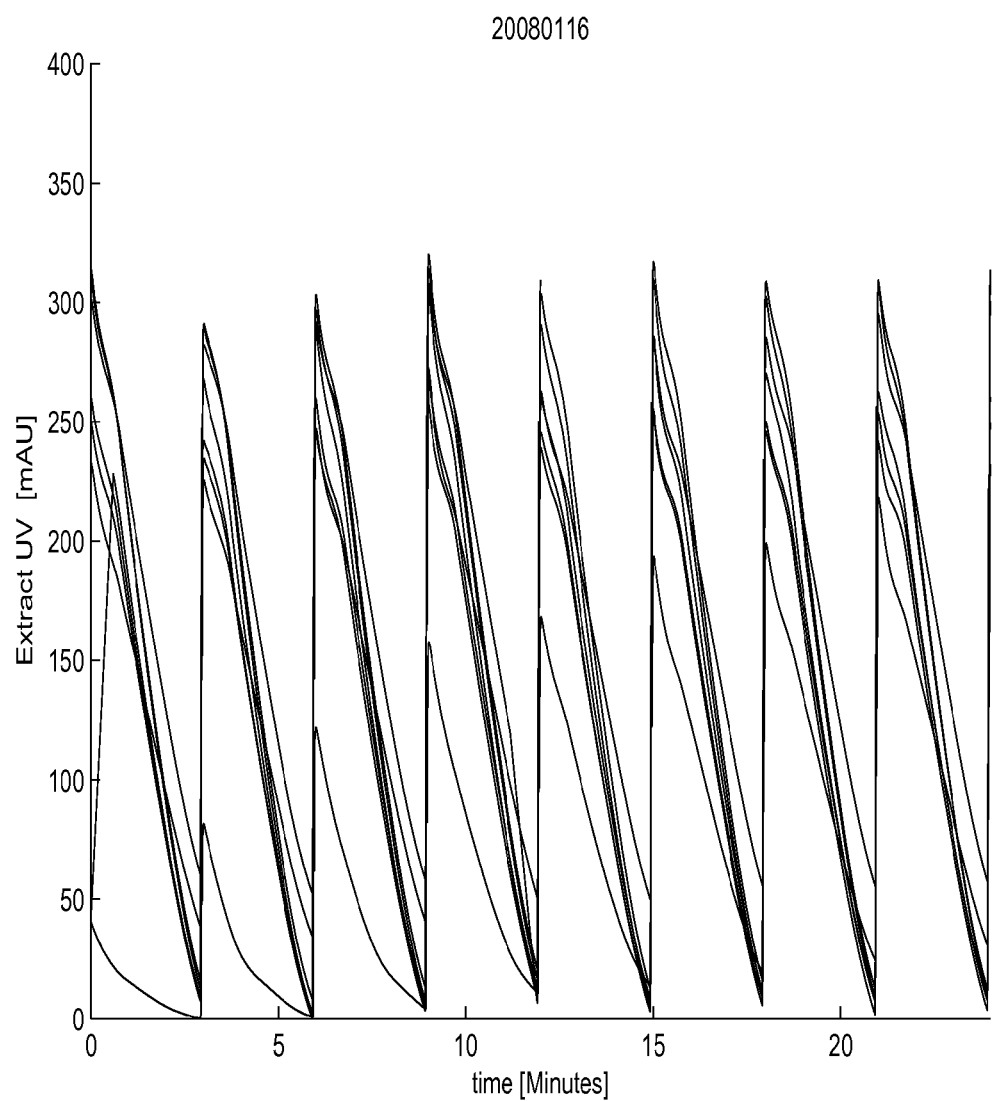

FIG. 25: The measured UV-signal from the extract stream in experiment IV. The data are plotted for each cycle, 8 columns with 3 min shifting time. Initially the UV-signal is increasing due to the start up of the SMB-plant.

Figure 26:
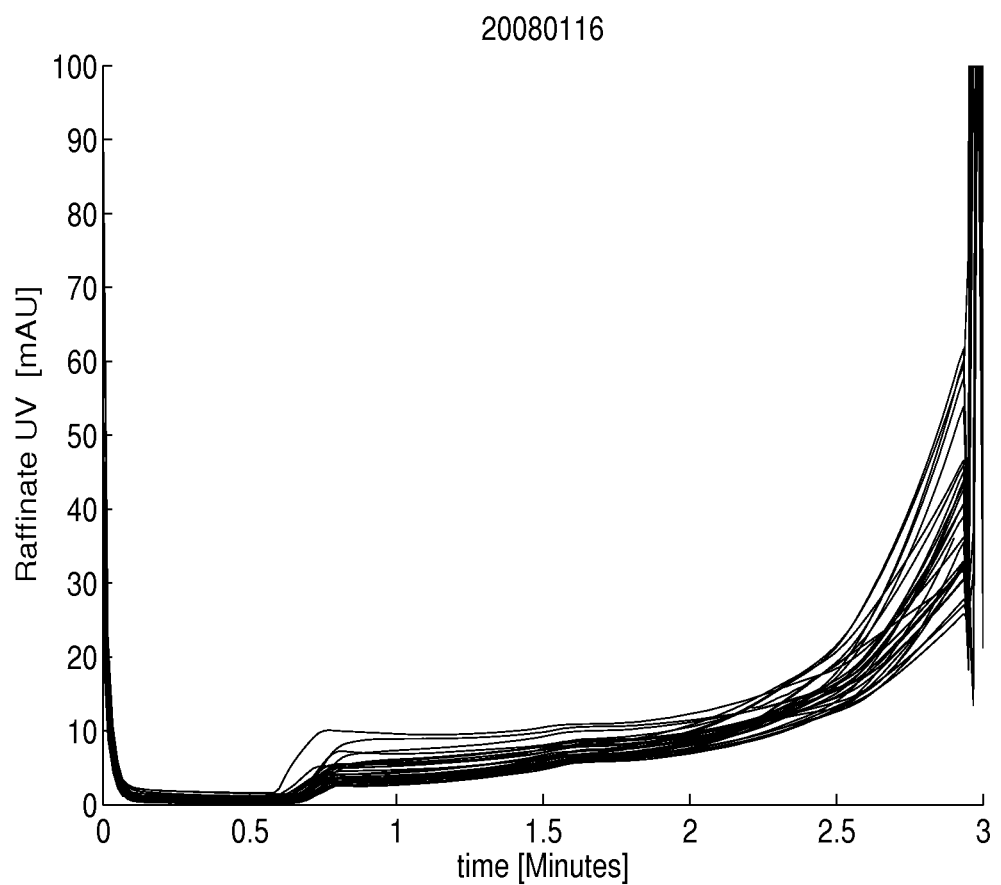

FIG. 26: The raffinate port UV-signal for experiment IV after a cyclic steady state is obtained. The columns are moved into zone II after having passed the regeneration and equilibration zone, therefore the UV-signal is initially zero. The UV-signal increases when the components are eluted. The feed stream contains a number of weakly bound impurities, and no clear peak is seen as in FIG. 22.

DETAILED DISCLOSURE OF THE INVENTION

Peptides such as GLP-1 peptides may e.g. be produced recombinantly in a fermentation process or synthetically on a solid phase. Regardless of the production form, a number of impurities are produced in addition to the polypeptide of interest. For example when produced recombinantly, besides producing the polypeptide of interest, the cells also produce a number of other substances such as e.g. high molecular weight proteins (HMWP) and small molecules (e.g. oxalate). These are normally quite simple to separate from the polypeptide of interest due to the lack of similarity with the polypeptide of interest. Additionally, components very similar to the polypeptide of interest are produced by the cell, e.g. glycosylated, deamidated, truncated, aggregated, dimers, oxidized impurities etc., thus proteins or peptides almost identical to the polypeptide of interest. These impurities are much more difficult to separate from the polypeptide of interest due to the high degree of similarity between the impurities and the polypeptide of interest. In chromatography the retention volumes of the polypeptide of interest and these impurities are thus very close to each other. In an isocratic mode this will put a narrow constraint on the requirements of the feed stream and the desorbent stream.

Purification systems have been described which are suitable for separating enantiomers. When enantiomers are separated by said purification systems, the components to be separated are normally present in equal or close to equal concentrations. In contrast to this, the concentration of the polypeptide of interest in e.g. a fermentation broth may be significantly higher than the concentration of the similar impurities, which often makes it difficult to separate said impurities from the polypeptide of interest while also achieving a high yield of the polypeptide of interest.

FIG. 2 illustrates such situation where a fluid mixture to be purified comprises a polypeptide of interest as well as a similar impurity. Here two isotherms are shown in a graph where the adsorbed concentration is plotted as a concentration of the liquid phase concentration. The concentration of the product is 8 g/L and the concentration of the impurity, which is present in much lower concentration, is 0.4 g/L. From the figure it is seen that the initial slope of the isotherm is a good approximation of the isotherm of the weaker bound component, whereas the approximation of the stronger bound component is not as good. In one aspect of the invention the initial slope of the isotherm of the weaker bound component is used to choose the modifier concentrations in a counter current process.

As an illustrative example, the instance where a counter current process as illustrated in FIG. 5 has isotherms similar to the isotherms given in FIG. 2 may be considered. This results in a stronger adsorption to the resin of the product, which is present in high concentration than of the impurity present in low concentration.

In this case the elution of the impurity in e.g. the raffinate stream can either occur due to
1. displacement effects from the product in zone III
2. the downward curvature of the isotherm from the impurity itself, or
3. the initial slope of the isotherm is adequately low to allow elution In case 1 where e.g. a weakly bound impurity will be displaced by the product, the product may be lost in the raffinate stream. The impurity is eluting just before the product due to displacement effects.

In case 2 a weakly bound impurity is not able to elute at a low concentration under the conditions in zone III. In this case the weakly bound component will neither be washed out in the extract stream nor in the raffinate stream but simply build up in the plant. The concentration of the weakly bound impurity will accumulate until the concentration is adequately high for the impurity to elute due to the curvature of the isotherm. The disadvantage in this case is the accumulation of the impurity in the plant. This increased amount of impurity will decrease the amount of vacant ligands and thereby the binding capacity of the product and an increased amount of impurity needs to be eluted in zone II to avoid it from ending in the raffinate steam.

Case 3 is the situation as covered herein where the concentration of the modifier in the feed stream and the desorbent stream are selected so that the weakly bound impurity will always be able to elute to the raffinate stream. In this case a build-up of the impurity is avoided. This can be done by a proper selection of modifier concentrations in the desorbent and feed stream as suggested herein.

The inventor has with the present invention provided a particularly efficient purification method for separating related impurities from a polypeptide of interest. The initial slope of the isotherm in said purification method is thus optimal for purifying a polypeptide of interest wherein the peptide product and related impurities are present in the fluid mixture to be purified such as a fluid mixture obtained from a fermentation process. In one aspect of the invention the optimal initial slope of the isotherm is obtained by selecting the modifier gradient in a counter current purification system such as a SMB-plant wherein the weaker bound components, i.e. the weakly bound impurities, which are present at low concentrations, are eluted in the raffinate stream. In one aspect the elution of the weaker bound impurities according to a method of the invention prevents build up of said impurities in the plant. In one aspect of the invention the modifier gradient is a salt gradient. In one aspect a counter current purification system according to the invention is used for purifying a fermentation broth wherein separation of GLP-1 from its impurities is obtained.

In one aspect a counter current purification system is used according to the invention for purifying a fluid mixture comprising a synthetically produced protein or peptide product, wherein separation of a GLP-1 peptide from its impurities is obtained.

In one aspect a counter current purification system is used according to the invention for purifying a fluid mixture comprising an insulin peptide such as e.g. human insulin, desB30 human insulin or AspB28 human insulin, wherein separation of the insulin from its impurities is obtained.

In one aspect a counter current purification system is used according to the invention for purifying a fluid mixture comprising a protein or peptide from its impurities, wherein the columns used are RP HPLC columns.

Understanding the influence of the equilibrium on the retention of the various components such as the polypeptide of interest and the related impurities thereof will also allow for the use of gradients not normally applied in counter current separations systems, e.g. pH-gradients in IEX. Thus in one aspect a counter current purification system is used according to the invention for purifying a fluid mixture comprising a protein or peptide from it its impurities, wherein the modifier used is pH and the columns used are IEX columns.

The concentration of an organic component will also influence the equilibrium in IEX and hence an organic component in e.g. IEX can also be applied. Thus in one aspect a counter current purification system is used according to the invention for purifying a fluid mixture comprising a protein or peptide from it its impurities, wherein a second modifier used is an organic component and the columns used are IEX columns.

Often the isotherm is convex and the ratio between the concentration of the adsorbed component, q, and the concentration in the liquid phase, c, i.e. q/c, is decreasing when the concentration is increased (Guiochon 2006). This can also be seen in FIG. 2. In one aspect of the invention the isotherm is close to the operating line of the weaker bound component. This has the advantage that breakthrough in section III is avoided. Additionally the reduction in available ligands when loading section II reduces the risk of having the weaker bound component in the extract.

The inventor of the present invention has found that a solution to the difficult purification problem presented above is using gradients in the SMB-process. Gradients have previously been shown to be efficient in difficult separation problems, however not used as suggested in the present invention, where the difference in concentration between product and impurity in the feed stream is large.

In one aspect of the invention a different modifier concentration in the feed stream and in section II is provided, wherein the equilibrium in section III of the plant is a function of the feed flow.

Certain robustness towards fluctuations and process changes is desired. In FIG. 9 is plotted the initial slope together with the dimensionless flow, $m^{III}$, in a gradient case. In one aspect $m^{III}$ is between the initial slope of each isotherm, A, of the two components. This has the effect that the components are separated. As seen in FIG. 9 the feed flow can in this case e only be varied between app. 3.3 and 6.6.

The inventor has with the present invention provided an attractive method of purifying a polypeptide of interest by combining thermodynamic knowledge with the knowledge of the counter current purification technology, such as SMB in a novel and inventive way.

Fixed Bed Chromatography

Fixed Bed (FB) chromatography is currently widely used for purifying components in the pharmaceutical industry. In fixed bed chromatography the desired product mixed with the impurities are applied to the column whereafter it is eluted from the column. At the outlet of the column the product can be collected from the impurities.

In a FB chromatogram of such a fluid mixture of a polypeptide of interest and a related impurity, an overlap of the two peaks is often observed (FIG. 1). In this case the product is not completely separated from the impurity at the outlet of the column, and it is not possible to obtain both a high purity and a high yield.

SMB

To overcome the limitations of the FB chromatography, counter current chromatography can be used. A widely used process is the Simulated Moving Bed (SMB), this has previously shown to be efficient in purifying proteins, both with respect to purity, productivity and solvent consumption (Schulte (2000)).

In an SMB-plant the columns are moved counter-current to the flow direction at a certain shifting time. Therefore the process varies both with respect to time and position.

SMB has also been considered for the purification of insulin (Jensen (2000)), where a theoretical study was made separating a feed stream consisting of 1 g/l bovine and ½ g/l porcine insulin. It was shown that by applying a gradient of acetonitrile in a reversed phase chromatographic process the consumption figures could be reduced.

Insulin purification has been experimentally demonstrated by Wang in EP1349866B1. In this experiment the insulin was separated from $ZnCl_2$ and HMWP.

The SMB-process is a discontinuous process, since the columns are shifted at certain times, $t_{sft}$. This makes a set of equations with both derivatives in time and position.

To simplify the analysis of the equations the True Moving Bed (TMB) is often studied in stead (Guiochon, 2006, p. 780). The TMB is also known as True Counter Current (TCC) (Ruthven & Ching 1989) or Continuous Moving Bed (CMB), (Ma & Wang 1997). In the TMB the resin flow is considered to be continuously moving in the opposite direction of the liquid flow, in this case the process becomes steady state, and only derivatives in position remain. The concentration profiles obtained from these equations are often known as the steady-state concentration profile (Ruthven & Ching 1989), or standing wave concentration profile (Ma & Wang 1997).

It has previously been shown that in the ideal case these two approaches are identical (Guiochon 2006).

Complete Separation Region

A widely applied approach for determining the operating point in an SMB-plant is the triangular theory (Storti 1989). This approach can be derived from ideal chromatography for a TMB. In the ideal case the resistance against mass transfer and axial dispersion is neglected.

The controlling parameter in a counter current process is the ratio between the flow rates of the two phases compared to the concentration in the two phases (Ruthven 1989).

In the triangular theory the ratio of the flow is given as $$m^j = \frac{\text{net fluid flow rate in section } j}{\text{adsorbed phase flow rate}} \quad j = I, II, III, \ldots$$

This is compared to the concentration of the component i in the two phases, $$\frac{q_i}{c_i}.$$

For a linear isotherm the complete separation region will be a triangle (Storti 1993). The optimal operating point will be the point W as illustrated in FIG. 12. In this case the flow in section II is the minimum to obtain a complete separation and the flow in section III is at maximum. Since the difference between the flow in section II and III is the feed flow, a high $m^{III}$ and low $m^{II}$ corresponds to a high feed flow.

For a convex isotherm this optimal operating point will move downward (lower values of $m^{II}$ and $m^{III}$), FIG. 13.

Jensen (2000) has previously shown how this optimal operating point will move upward (higher value of $m^{III}$), leading to lower consumption of desorbent, when a gradient is applied in a SMB-plant, FIG. 14.

However this was not very well understood. An additional insight can be obtained from thermodynamics.

Other approaches for calculating the complete separation region have been suggested e.g. the Standing Wave design (Ma and Wang, 1997) or the steady state solution suggested by Ruthven (1989). In the ideal case these methods give identical results.

Normally axial dispersion and/or mass transfer may be present. Analytical solutions for calculating the concentration profiles have been published for the linear isotherm e.g. the standing wave method (Ma & Wang 1997) or the steady state concentration profile (Ruthven 1989). However, the problem can always be solved using numerical methods. A concentration profile calculated by solving the equations numerically is given in FIG. 4. This can be solved both for linear and non-linear isotherms and requires fewer assumptions, compared to the analytical solutions. The number of plates can normally be found from a van Deemter plot (FIG. 11, Guiochon 2006).

Gradients

Gradients have been applied both, with varying the concentration of the organic phase in reversed phase chromatography (Jensen 2000) and with salt concentration in ion-exchange chromatography (Wekenborg 2004).

The advantage of using gradients in a SMB is that the components are stronger retained downstream from the feed point than upstream from the feed point which allows a higher feed flow. This leads to reduced solvent consumption, increased productivity and more concentrated product streams (Kessler 2007). In the triangular diagram this can be seen from the point "W", which moves upwards when using gradients (FIG. 14).

The isotherms are often described by using a simple Langmuir isotherm or multicomponent Langmuir isotherm and making the parameters dependent on the solvent composition (Antos et al. 2001) or simply interpolating functions (Abel et al. 2002).

However by using thermodynamics to describe the isotherms, more optimal gradients have been developed by the inventor, whereby a good purification of a polypeptide of interest is obtained when a fluid mixture of a polypeptide of interest and related impurities are purified according to the method of the invention.

Thermodynamics

Thermodynamic principles have recently been applied for describing the adsorption equilibrium for the adsorption of macromolecules to the surface of a resin (Mollerup, 2006 and 2008).

This gives an extra insight into how the parameters influence the adsorption equilibria.

The ratio between the concentration of bound component, $q_i$, and non-bound component, $c_i$, is given by $$\frac{q_i}{c_i} = A_i \cdot \left(1 - \sum_{j=1}^{m} \frac{q_j}{q_j^{max}}\right)^{v_i}$$

where the initial slope $A_i$ depends on the type of chromatography.

Ion Exchange Chromatography (IEX)

For ion exchange chromatography the initial slope $A_i$ is given by $$A_i = K_{eq,i} \cdot \left(\frac{\Lambda}{c_s \cdot z_s}\right)^{v_i} \cdot \gamma_i$$

Where $\Lambda$ is the concentration of the ligands, $c_s$ the salt concentration, $z_s$ the charge of the salt and $\gamma_i$ the activity coefficient. The ratio between the charge of component i and the salt is $v_i$, $v_i = z_i/z_s$ (Mollerup 2008).

Normally the salt concentration is the variable controlling the adsorption.

This is identical to what has previously been published by Brooks and Cramer (1992)

Reverse Phase Chromatography (RPC) & Hydrophobic Interaction Chromatography (HIC)

In hydrophobic interaction chromatography (HIC) and reversed phase chromatography (RP) the dependency of the initial slope $A_i$ is given by $$A_i = K_{eq,i} \cdot \left(\frac{\Lambda}{c}\right)^{v_i} \cdot \gamma_i$$

where c is the total concentration in the mobile phase (Mollerup 2008)

In HIC and RP the adsorption is usually controlled by changing the mobile phase and thereby the activity coefficient, $\gamma_i$. The activity coefficient for the protein, polypeptide or peptide of interest can be calculated as $$\ln(\gamma_i) = K_i \cdot c_i + K_m \cdot c_m$$

which at low protein/peptide concentrations gives $$\ln(\gamma_i) = K_m \cdot c_m$$

Optimal Feed Concentration

Using an open loop as shown in FIG. 5, is attractive because not only one impurity but a number of impurities are eluting before the product. Therefore the gradient introduced from the feed will not influence the concentration in section I and II.

The dimensionless fluid flow in section III is given as $$m^{III} = m^{II} + \frac{Q^F}{Q^{pore}}$$

Defining $\alpha$ as the feed flow divided by the net flow in section II gives $$\alpha = \frac{Q^F}{Q^{II}_{Net}}$$

and insertion gives $$m^{III} = m^{II} + \frac{Q^{II}_{Net}}{Q^{pore}} \cdot \alpha = m^{II}(1+\alpha)$$

where $Q_{Net}$ is the net fluid flow in the section identical to the net liquid flow divided by the pore phase flow in a TMB plant. In a SMB-plant the net flow is given as $$Q_{Net}^{II} = Q_{SMB}^{II} - V_{SMB}^{NR}/t_{sft}$$

The derivative of $m^{III}$ with respect to the feed flow is $$\frac{\partial m^{III}}{\partial Q^F} = \frac{1}{Q_{pore}}$$

or in dimensionless flows this becomes $$\frac{\partial m^{III}}{\partial \alpha} = m^{II}$$

This will therefore always lead to a linear relationship between $\alpha$ and $m^{III}$ as seen in FIG. 8-FIG. 10.

Ion Exchange Chromatography (IEX)

For ion exchange chromatography the initial slope $A_i$ is given by $$A_i = K_{eq,i} \cdot \left(\frac{\Lambda}{c_s \cdot z_s}\right)^{v_i} \cdot \gamma_i$$

The main controlling parameter is here the salt concentration, $c_s$. The activity coefficient is therefore neglected, and the derivative with respect to $c_s$ is $$\frac{\partial A_i}{\partial c_s} = -\frac{v_i}{c_s} \cdot K_{eq,i} \cdot \left(\frac{\Lambda}{c_s \cdot z_s}\right)^{v_i} \cdot \gamma_i = -\frac{v_i}{c_s} \cdot A_i$$

The salt concentration in section III is obtained by mixing the feed flow with the flow outlet of section II $$c_s^{III} = \frac{Q_{Net}^{II} \cdot c_s^{II} + Q^F \cdot c_s^F}{Q_{Net}^{II} + Q^F}$$

Division of all the flows by the pore flow gives $$c_s^{III} = \frac{Q_{Net}^{II}/Q_{pore} \cdot c_s^{II} + Q^F/Q_{pore} \cdot c_s^F}{Q_{Net}^{II}/Q_{pore} + Q^F/Q_{pore}}$$

$$= \frac{m^{II} \cdot c_s^{II} + m^{II} \cdot \alpha \cdot c_s^F}{m^{II} + m^{II} \cdot \alpha}$$

$$= \frac{c_s^{II} + \alpha \cdot c_s^F}{1 + \alpha}$$

When the feed flow is changed, the change in salt concentrations in section III will be $$\frac{\partial c_s^{III}}{\partial Q^F} = \frac{Q_{Net}^{II} \cdot (c_s^F - c_s^{II})}{(Q_{Net}^{II} + Q^F)^2}$$

or with the dimensionless feed flow $$\frac{\partial c_s^{III}}{\partial \alpha} = \frac{c_s^F - c_s^{II}}{(1+\alpha)^2}$$

A change in the initial slope, of component i in section III, as a function of the change in the feed flow will hence give $$\frac{\partial A_i^{III}}{\partial Q^F} = \frac{\partial A_{ii}^{III}}{\partial c_s^{III}} \frac{\partial c_s^{III}}{\partial Q^F} = -\frac{v_i}{c_s^{III}} \cdot A_i^{III} \cdot \frac{Q_{Net}^{II} \cdot (c_s^F - c_s^{II})}{(Q_{Net}^{II} + Q^F)^2}$$

or in dimensionless feed flow $$\frac{\partial A_i^{III}}{\partial \alpha} = \frac{\partial A_{ii}^{III}}{\partial c_s^{III}} \frac{\partial c_s^{III}}{\partial \alpha} = -\frac{v_i \cdot A_i^{III}}{c_s^{III}} \cdot \frac{c_s^F - c_s^{II}}{(1+\alpha)^2}$$

It is desirable if the change in inlet salt concentration will lead to the same change in the equilibrium as the feed flow change, namely $$\frac{\partial m^{III}}{\partial Q^F} = \frac{\partial A_i^{III}}{\partial Q^F}$$

or with the dimensionless feed flow $$\frac{\partial m^{III}}{\partial \alpha} = \frac{\partial A_i^{III}}{\partial \alpha}$$

In absolute properties this becomes $$\frac{1}{Q_{pore}} = -\frac{v_i}{c_s^{III}} \cdot A_i^{III} \cdot \frac{Q_{Net}^{II} \cdot (c_s^F - c_s^{II})}{(Q_{Net}^{II} + Q^F)^2}$$

and with the dimensionless flow rate $$m^{II} = -\frac{v_i \cdot A_i^{III}}{c_s^{III}} \cdot \frac{c_s^F - c_s^{II}}{(1+\alpha)^2}$$

Insertion of $c_s^{III}$ gives the relation $$m^{II} = \frac{v_i \cdot A_i^{III}}{1+\alpha} \cdot \frac{c_s^{II} - c_s^F}{c_s^{II} + \alpha \cdot c_s^F}$$

and isolating $c_s^F$ gives $$c_s^F = \frac{v_i \cdot A_i^{III} \cdot \frac{Q_{Net}^{II}}{Q_{Net}^{II} + Q^F} - \frac{Q_{Net}^{II}}{Q_{pore}}}{v_i \cdot A_i^{III} \cdot \frac{Q_{Net}^{II}}{Q_{Net}^{II} + Q^F} + \frac{Q^F}{Q_{pore}}} \cdot c_s^{II}$$

$$c_s^F = \frac{v_i \cdot A_i^{III} - (1+\alpha) \cdot m^{II}}{v_i \cdot A_i^{III} + (1+\alpha) \cdot \alpha \cdot m^{II}} \cdot c_s^{II}$$

Since $A^{III}$ is a function of the ethanol concentration which depends on $c_s^F$, a few iterations are required to obtain the correct salt concentration in the feed stream.

In one aspect the operating points $Q^F$ and $Q^{II}$ and the initial slope, $A_i^{III}$, are inserted into the expression, whereby the slope of the operating line around the operating point, is identical to the initial slope of the dependency of change in the feed flow of the isotherm.

With a salt concentration in section II and a feed salt concentration as given above the initial slope can be calculated for all feed flows, FIG. 10.

Reverse Phase Chromatography (RPC) & Hydrophobic Interaction Chromatography (HIC)

In RP and HIC the initial slope of the isotherm is given by $$A_i = K_{eq,i} \cdot \left(\frac{\Lambda}{c}\right)^{v_i} \cdot \gamma_i$$

$$\ln(\gamma_i) = K_m \cdot c_m$$

where $c_m$ is the concentration of the modifier e.g. ethanol.

A change in $c_m$ only changes the total concentration, c, marginally, and thus c is considered to be constant The derivative of the initial slope with $c_m$ is $$\frac{\partial A_i}{\partial c_m} = K_{eq,i} \cdot \left(\frac{\Lambda}{c}\right)^{v_i} \cdot K_m \cdot \gamma_i$$

where $K_m$ can be found as the slope in a semi-logarithmic plot of $\tilde{V}_R - \tilde{V}_{NR}$ as a function of $c_m$ (see FIG. 7).

The concentration of the modifier in section III is given as $$c_m^{III} = \frac{Q_{Net}^{II} \cdot c_m^{II} + Q^F \cdot c_m^F}{Q_{Net}^{II} + Q^F}$$

or using the dimensionless feed flow $$c_m^{III} = \frac{c_m^{II} + \alpha \cdot c_m^F}{1+\alpha}$$

The derivative of this is $$\frac{\partial c_m^{III}}{\partial Q^F} = \frac{Q_{Net}^{II} \cdot (c_m^F - c_m^{II})}{(Q_{Net}^{II} + Q^F)^2}$$

or in dimensionless variables $$\frac{\partial c_m^{III}}{\partial \alpha} = \frac{c_m^F - c_m^{II}}{(1+\alpha)^2}$$

and the change in the initial slope of the isotherm as a function of the modifier concentration in section III is $$\frac{\partial A_i^{III}}{\partial Q^F} = \frac{\partial A_i^{III}}{\partial c_m^{III}} \frac{\partial c_m^{III}}{\partial Q^F}$$

$$= K_{eq,i} \cdot \left(\frac{\Lambda}{c^{III}}\right)^{v_i} \cdot \gamma_i \cdot K_m \cdot \frac{Q_{Net}^{II} \cdot (c_m^F - c_m^{II})}{(Q_{Net}^{II} + Q^F)^2}$$

$$= A_i^{III} \cdot K_m \cdot \frac{Q_{Net}^{II} \cdot (c_m^F - c_m^{II})}{(Q_{Net}^{II} + Q^F)^2}$$

corresponding to $$\frac{\partial A_i^{III}}{\partial \alpha} = \frac{\partial A_i^{III}}{\partial c_m^{III}} \frac{\partial c_m^{III}}{\partial \alpha}$$

$$= K_{eq,i} \cdot \left(\frac{\Lambda}{c^{III}}\right)^{v_i} \cdot \gamma_i \cdot K_m \cdot \frac{c_m^F - c_m^{II}}{(1+\alpha)^2}$$

$$= K_m \cdot A_i^{III} \cdot \frac{c_m^F - c_m^{II}}{(1+\alpha)^2}$$

For this case the optimal solution will be $$\frac{\partial m^{III}}{\partial Q^F} = \frac{\partial A_i^{III}}{\partial Q^F}$$

or $$\frac{\partial m^{III}}{\partial \alpha} = \frac{\partial A_i^{III}}{\partial \alpha}$$

leading to $$\frac{1}{Q_{pore}} = K_m \cdot A_i^{III} \cdot \frac{Q_{Net}^{II} \cdot (c_m^F - c_m^{II})}{(Q_{Net}^{II} + Q^F)^2}$$

or $$m^{II} = K_m \cdot A_i^{III} \cdot \frac{c_m^F - c_m^{II}}{(1+\alpha)^2}$$

which by isolating the feed concentration gives $$c_m^F = \frac{(Q_{Net}^{II} + Q^F)^2}{Q_{Net}^{II} \cdot Q_{pore} \cdot A_i^{III} \cdot K_m} + c_m^{II}$$

or $$c_m^F = \frac{m^{II} \cdot (1+\alpha)^2}{K_m \cdot A_i^{III}} + c_m^{II}$$

Determination of Equilibrium Parameters:

The retention volume for a component with a linear isotherm is given by $$V_R = V_{col}(\epsilon + (1-\epsilon) \cdot \epsilon_p K_D \cdot (1+A_i)) + V_{dead}$$

where $A_i$ is the initial slope of the isotherm $$A_i = \lim_{c_i \to 0}\left(\frac{\partial q_i}{\partial c_i}\right)$$

and $V_{dead}$ is the dead volume.

For a non-retained (NR) component the retention volume will be $$V_{NR} = V_{col}(\epsilon + (1-\epsilon) \cdot \epsilon_p K_D) + V_{dead}$$

leading to $$\tilde{V}_R - \tilde{V}_{NR}(V_R - V_{NR})/V_{col} = (1-\epsilon) \cdot \epsilon_p K_D \cdot A_i$$

The initial slope, A, will normally depend on the type of chromatography, composition of the mobile phase, and the packing material (Mollerup 2008).

Ion Exchange Chromatography (IEX):

Inserting the expression of $A_i$ for IEX gives $$\tilde{V}_R - \tilde{V}_{NR} = (1-\varepsilon) \cdot \varepsilon_p K_D \cdot K_{eq,i} \cdot \left(\frac{\Lambda}{c_s \cdot z_s}\right)^{v_i} \cdot \gamma_i$$

This is rewritten as $$\ln(\tilde{V}_R - \tilde{V}_{NR}) = \ln\left[(1-\varepsilon) \cdot \varepsilon_p K_D \cdot K_{eq,i} \cdot \left(\frac{\Lambda}{z_s}\right)^{v_i} \cdot \gamma_i\right] - v_i \ln(c_s)$$

Since the main factor controlling IEX is the salt concentration, the salt dependency can be found in a double logarithmic plot by plotting $c_s$ on the x-axis and $\tilde{V}_R - \tilde{V}_{NR}$ on the y-axis (FIG. 6). The data plotted in this manner can be fitted to the line $$\ln(\tilde{V}_R - \tilde{V}_{NR}) = \alpha_i \cdot \ln(c_s) + \beta_i$$

from which it can be seen that $v_i = \div \alpha_i$.

Reverse Phase Chromatography (RPC or RP) & Hydrophobic Interaction Chromatography (HIC):

In RP and HIC the expression becomes $$\tilde{V}_R - \tilde{V}_{NR} = (1-\varepsilon) \cdot \varepsilon_p K_D \cdot K_{eq,i} \cdot \left(\frac{\Lambda}{c}\right)^{v_i} \cdot \gamma_i$$

This is rewritten as $$\ln(\tilde{V}_R - \tilde{V}_{NR}) = \ln\left[(1-\varepsilon) \cdot \varepsilon_p K_D \cdot K_{eq,i} \cdot \left(\frac{\Lambda}{c}\right)^{v_i}\right] + K_m \cdot c_m$$

where $\ln(\gamma_i) = K_m \cdot c_m$ has been inserted. The dependency on salt or organic modifier can therefore be found in a semi-logarithmic plot by plotting $\ln(\tilde{V}_R - \tilde{V}_{NR})$ as a function of $c_m$ (FIG. 7). The data plotted in this manner can be fitted to the line $$\ln(\tilde{V}_R - \tilde{V}_{NR}) = \alpha_i \cdot c_m + \beta_i$$

from which it can be seen that $K_m = \alpha_i$.

Intervals for the Feed Concentration

Depending on the type of chromatography IEX or RP/HIC used in the Counter Current System, the equilibrium is described differently, and the modifier feed concentration according to the method of the invention will therefore depend on the type of chromatography Ion Exchange Chromatography (IEX):

For IEX it has elsewhere herein been shown that the feed salt concentration giving the same slope for component i and the operating line is $$c_s^F = \frac{v_i \cdot A_i^{III} - (1+\alpha) \cdot m^{II}}{v_i \cdot A_i^{III} + (1+\alpha) \cdot \alpha \cdot m^{II}} \cdot c_s^{II}$$

Insertion of $m^{III} = (1+\alpha) \cdot m^{II}$ and division by $c_s^{II} \cdot A_i^{III}$ gives $$\frac{c_s^F}{c_s^{II}} = \frac{v_i - \frac{m^{III}}{A_i^{III}}}{v_i + \alpha \cdot \frac{m^{III}}{A_i^{III}}}$$

The optimal operating point is a low flow in section II and a high flow in section III, corresponding to a low desorbent consumption and a high feed flow, see FIG. 12.

To avoid elution of the stronger bound component A, in the raffinate stream. The maximum $m^{III}$ will correspond to $m^{III} = A_A^{III}$, and insertion gives $$\frac{c_s^F}{c_s^{II}} = \frac{v_i - \frac{A_A^{III}}{A_i^{III}}}{v_i + \alpha \cdot \frac{A_A^{III}}{A_i^{III}}}$$

For the weaker bound component, B, this ratio gives $$\frac{c_s^F}{c_s^{II}} = \frac{v_B - \frac{A_A^{III}}{A_B^{III}}}{v_B + \alpha \cdot \frac{A_A^{III}}{A_B^{III}}} = \frac{v_B - \alpha_{AB}^{III}}{v_B + \alpha \cdot \alpha_{AB}^{III}}$$

where the selectivity is given as $$\alpha_{AB} = \frac{A_A}{A_B}$$

and insertion of the parameters $\alpha_i$ and $\beta_i$ fitted to the experimental pulse experiments (see FIG. 6 and tables 1 and 2) gives $$\alpha_{AB} = \exp(\beta_A - \beta_B) \cdot c_s^{(\alpha_A - \alpha_B)}$$

Correspondingly for the stronger bound component where the minimum flow in section II is approximately at $\alpha=0$, corresponding to $m^{II}=A_B^{II}=A_B^{III}$, the expression becomes $$\frac{c_s^F}{c_s^{II}} = \frac{v_A - \frac{A_B^{III}}{A_A^{III}}}{v_A + \alpha \cdot \frac{A_B^{III}}{A_A^{III}}} = \frac{v_A - 1/\alpha_{AB}^{III}}{v_A + \alpha/\alpha_{AB}^{III}}$$

A reasonable interval for the salt concentration in the feed stream relative to the salt concentration in section II is $$\frac{v_B - \alpha_{AB}^{III}}{v_B + \alpha \cdot \alpha_{AB}^{III}} \leq \frac{c_s^F}{c_s^{II}} \leq \frac{v_A - 1/\alpha_{AB}^{III}}{v_A + \alpha/\alpha_{AB}^{III}}$$

A reasonable value of the dimensionless feed flow $\alpha$ will be in the range 0 to ½. This corresponds to a feed flow which is less than half the flow in section II. Hence the interval becomes $$\frac{v_B - \alpha_{AB}^{III}}{v_B + 1/2 \cdot \alpha_{AB}^{III}} \leq \frac{c_s^F}{c_s^{II}} \leq \frac{v_A - 1/\alpha_{AB}^{III}}{v_A}$$

bearing in mind that $v_i = \div \alpha_i$ and the selectivity is calculated from the fitted parameters $\alpha_i$ and $\beta_i$ determined from experimental pulse experiments.

Thus in one aspect of the invention where the Counter Current System is an Ion Exchange Chromatography system, the salt concentration in the feed stream relative to the salt concentration in the section prior to the feed stream is within the range:

$$\frac{v_B - \alpha_{AB}^{III}}{v_B + \alpha \cdot \alpha_{AB}^{III}} \leq \frac{c_s^F}{c_s^{II}} \leq \frac{v_A - 1/\alpha_{AB}^{III}}{v_A + \alpha/\alpha_{AB}^{III}}.$$

Reverse Phase Chromatography (RPC or RP) & Hydrophobic Interaction Chromatography (HIC):

In RP and HIC the feed concentration leading to the same slope of the operating line and change in initial slope is given by $$c_m^F = \frac{m^{II} \cdot (1+\alpha)^2}{K_m \cdot A_i^{III}} + c_m^{II} = \frac{1+\alpha}{K_m} \cdot \frac{m^{III}}{A_i^{III}} + c_m^{II}$$

Again as stated under IEX above and seen in FIG. 12 the optimal operating point will be at $m^{III}=A_A^{III}$ and insertion gives $$c_m^F = \frac{1+\alpha}{K_m} \cdot \frac{A_A^{III}}{A_i^{III}} + c_m^{II}$$

For the weaker bound component and insertion of the selectivity gives $$c_m^F = \frac{1+\alpha}{K_{m,B}} \cdot \alpha_{AB}^{III} + c_m^{II}$$

Where $\alpha_{AB}^{III}$ is the selectivity between component A and B in section III.

In RP and HIC the selectivity can be found from the isocratic pulse experiments fitted to $$\ln(\tilde{V}_R - \tilde{V}_{NR}) = \alpha_i \cdot c_m + \beta_i$$

and the selectivity between the two components becomes $$\alpha_{AB} = \frac{A_A}{A_B} = \frac{\exp(\alpha_A \cdot c_m + \beta_A)}{\exp(\alpha_B \cdot c_m + \beta_B)} = \exp((\alpha_A - \alpha_B) \cdot c_m + (\beta_A - \beta_B))$$

where it should be kept in mind that $\alpha_i = K_{m,i}$

For the stronger bound component, the feed stream modifier concentration becomes $$c_m^F = \frac{1+\alpha}{K_{m,A}} \frac{1}{\alpha_{AB}^{III}} + c_m^{II}$$

corresponding to the range $$\frac{1+\alpha}{K_{m,B}} \cdot \alpha_{AB}^{III} + c_m^{II} \leq c_m^F \leq \frac{1+\alpha}{K_{m,A} \cdot \alpha_{AB}^{II}} + c_m^{II}$$

or $$\frac{1+\alpha}{K_{m,B}} \cdot \alpha_{AB}^{III} \leq c_m^F - c_m^{II} \leq \frac{1+\alpha}{K_{m,A} \cdot \alpha_{AB}^{III}}$$

Again a reasonable value of the dimensionless feed flow $\alpha$ will be in the range 0 to ½. Hence the interval becomes $$\frac{1+1/2}{K_{m,B}} \cdot \alpha_{AB}^{III} \leq c_m^F - c_m^{II} \leq \frac{1}{K_{m,A} \cdot \alpha_{AB}^{II}}$$

bearing in mind that $\alpha_i = K_{m,i}$ and the selectivity is calculated from the fitted parameters $\alpha_i$ and $\beta_i$ determined from experimental pulse experiments.

Thus in one aspect of the invention, wherein the Counter Current System is a Reverse Phase Chromatography system or a Hydrophobic Interaction Chromatography system, the difference in modifier concentration in the feed stream and the desorbent stream is within the range:

$$\frac{1+1/2}{K_{m,B}} \cdot \alpha_{AB}^{III} \leq c_m^F - c_m^{II} \leq \frac{1}{K_{m,A} \cdot \alpha_{AB}^{III}}.$$

DEFINITIONS

The term "chromatography" as used herein refers to any technique used for the chemical separation of mixtures and components, that relies upon selective attraction among the components of a mixture for a solid phase. Examples include adsorption chromatography, partition chromatography, ion exchange chromatography, size exclusion chromatography and affinity chromatography.

The term "counter current purification system" as used herein refers to any purification system, wherein the solid phase moves against the current of the fluid stream either physically or is simulated to make this movement counter current relative to the fluid stream by the change in positioning of different separation beds of the system.

With the term "fluid connection" when used for solid phases of the counter current purification system, is herein meant the connection between solid phases used in the invention, wherein an outlet stream or fraction of an outlet stream is used as inlet stream to another solid phase during a cycle. A counter current purification system that comprises a plurality of sections in fluid connection according to the invention thus comprises at least two columns packed with solid phase, such as at least three columns packed with solid phase, which are in fluid connection.

Non-limiting examples of counter current purification systems according to the invention include any Simulated Moving Bed (SMB) chromatography system as well as Multicolumn Counter Current Solvent Gradient Purification (MCSGP). This may be stand alone systems as well as tandem and multivalent setups and may also be combined with other types of purifications systems.

Suitable SMB systems are e.g. disclosed in U.S. Pat. No. 2,985,589, U.S. Pat. No. 6,719,001, U.S. Pat. No. 4,574,840, U.S. Pat. No. 4,614,205, U.S. Pat. No. 3,040,777, U.S. Pat. No. 4,434,051 and U.S. Pat. No. 5,635,072. U.S. Pat. No. 6,544,413, and U.S. Pat. No. 6,979,402.

Other suitable systems have been disclosed in U.S. Pat. Nos. 6,462,221, 6,461,858, 6,458,995, and 6,455,736, and as disclosed in Gottschlich, et al., J. Chromatogr. A, 765 (1997) 201 and disclosed in WO 2004/024284. Another system is reported by Mun, et al., Biotechnol. Prog., 18 (2000) 1332.

Other suitable SMB systems are disclosed in WO 2001/087924, WO 2004/024284, and in WO 2008/019228.

WO 2008/048395 discloses the use of a small-scale simulated moving bed chromatography.

Suitable MCSGP systems are disclosed in e.g. WO 06/116886 and in European applications with publication numbers EP1877769 and EP1716900.

The term "counter current mode" when written in connection with contact of the fluid mixture with the solid phase, is herein used to mean that the net direction of the solid phase is opposite the net movement of the liquid phase. For example in FIG. 3, the net liquid flow is moving from the left to the right, whereas the columns at certain shifting times are moving from the right to the left creating at net flow of the solid phase opposite the liquid flow.

The terms "adsorbent" or "solid phase", as used herein, refers to the solid phase used in chromatography for which the mobile phase components exhibit a selective affinity. Because such affinity can take a variety of forms other than adsorption (including size exclusion or complexation), the term refers to solid phases that adsorb the components of a fluid mixture and to solid phases that do not technically adsorb components from the mobile phase, but which nevertheless behave as an adsorbent by slowing the migration velocity of one component relative to another in a chromatographic system. Non-limiting examples of adsorbents, i.e. chromatographic stationary phase materials, are e.g.: Substituted silica, such as C-4 silica, C-6 silica, C-12 silica, C-18 silica and phenyl-based silica, as well as polymeric materials such as polystyrene, e.g. Source or Poros materials; acrylate and methacrylate materials, e.g. from Tosoh, Rohm & Haas, and BioRad; agarose based materials, e.g. Sepharose; and hydroxyapatite based materials. Additional examples of chromatographic stationary phases are membranes, monolithic materials and filters.

With the term "the section prior to the feed stream" is herein meant the section from which the outlet stream is mixed with the feed stream. In FIG. 18, it is thus desorbent II which is the "section prior to the feed stream".

The term "purified" when referring to a component or fraction indicates that its relative concentration (weight of component or fraction divided by the weight of all components or fractions in the fluid mixture) is increased by at least 20%. In one series of aspects, the relative concentration is increased by at least 40%, 50%, 60%, 75%, 100%, 150%, or 200%, 300%, 400%, or 500%. A component or fraction can also be said to be purified when the relative concentration of components from which it is purified (weight of component or fraction from which it is purified divided by the weight of all components or fractions in the fluid mixture) is decreased by at least 20%, 40%, 50%, 60%, 75%, 85%, 95%, 98% or 100%. In still another series of aspects, the component or fraction is purified to a relative concentration of at least 50%, 65%, 75%, 85%, 90%, 97%, 98%, or 99%. When a component or fraction in some aspects is said to be "separated" from other components or fractions, it will be understood that the component or fraction is "purified".

The term "fluid mixture" as used herein refers to a fluid mixture that comprises at least two components, such as the polypeptide of interest and the one further component or fractions containing these compounds, which can be separated using a prescribed chromatographic process, because each component or fraction displays a different affinity for the adsorbent employed.

The term "polypeptide of interest", as used herein, refers to any peptide, polypeptide or protein that one needs to have in purified form. The term includes synthetic, semi-recombinant or recombinant peptides, polypeptides and proteins. In some aspects, the "polypeptide of interest" is a glucagon-like peptide such as e.g. GLP-1, GLP-1 analogue, GLP-1 derivative, exendin-4 or exendin-3. In one aspect of the invention the polypeptide of interest is a GLP-1 analogue or derivative. In one aspect of the invention the polypeptide of interest is a GLP-1 derivative. In one aspect of the invention the polypeptide of interest is produced by recombinant technology.

The terms "one further component" and "impurity", as used herein refers to a component present in the fluid mixture containing the polypeptide of interest which is not the polypeptide of interest and which has to be separated from the polypeptide of interest. This "one further component" may include host cell proteins, polypeptides or peptides, other unwanted forms of the recombinant polypeptide, such as glycosylated, deamidated, or oxidized forms, and other components present in the fluid mixture.

In some aspects the polypeptide of interest is a recombinant protein. In some aspects, the "one further component" is a peptide, polypeptide or protein similar to the polypeptide of interest (also herein described as a "related impurity") which has structural resemblance to the polypeptide of interest, such as a glycosylated form, a deamidated form, a truncated form, an extended form, a deamidated form, an incorrectly folded form, or an oxidized form of said polypeptide of interest, a form with undesired glycosylation, a form resulting from racemization, a form lacking amino acids in the intra-peptide chain, a form having extra amino acids in the intra-peptide chain and a form wherein an acylation has taken place on another residue than desired.

The relation between the "polypeptide of interest" and the "one further component" in the fluid mixture to be purified according to the method of the invention may be e.g. at least 4:1, i.e. when there is 1 equivalent of "one further component" in the fluid mixture there are at least 4 equivalents of the "polypeptide of interest". In one aspect of the invention the relation between the "polypeptide of interest" and the "one further component" in the fluid mixture is at least 6:1, in another aspect the relation is at least 8:1, in another aspect the relation is at least 9:1, in another aspect the relation is at least 14:1, in another aspect the relation is at least 19:1, in another aspect the relation is at least 20:1, in another aspect the relation is at least 50:1, and in yet another aspect the relation is at least 90:1.

The terms "desorbent stream", "desorbent", "eluent" or "eluent stream", as used interchangeably herein, refer to the mobile phase which is added to a counter current system between the raffinate and extract ports, see e.g. the illustration in FIG. 4. The term "desorbent stream" or "desorbent" is used because, when combined with the total mobile phase, the desorbent contributes to the desorption waves of the various components in their respective sections, whether by increasing the mobile phase velocity in a size exclusion system, or by physically displacing or removing the solution from the solid phase. Thus, the term "desorbent stream" is not meant to imply that the desorbent composition has any particular desorbent capacity, or that it desorbs through any particular physical mechanism.

In one aspect of the invention a counter current system is used with more desorbent streams such as e.g. two desorbent streams, "desorbent I" and "desorbent II". This is e.g. illustrated in FIG. 18.

The term "extract" as used herein refers to the stream leaving the plant upstream the feed point containing the stronger bound component(s). See e.g. FIGS. 3 and 5.

The term "raffinate stream" as used herein refers to the stream leaving the plant downstream the feed point containing the weaker bound component(s). See e.g. FIGS. 3 and 5.

The term "feed stream" as used herein refers to the stream entering the plant containing the components to be separated. See e.g. FIGS. 3 and 5.

The terms "section" and "zone" as used herein refer to a portion of the counter current purification system comprising at least one chromatography column or vessel. It is to be understood that in order to work as a counter current system, the system has to comprise a plurality of sections in fluid connection. At defined time intervals, the column in one position is switched in the opposite direction from the flow, producing a counter current movement of the solid phase relative to the fluid streams.

The term "modifier" as used herein refers to any component of the feed stream, which concentration may be adjusted by the use of the purification system. The preferred modifier depends on the chromatography system applied. Accordingly, if ion-exchange chromatography or hydrophobic interaction chromatography, (HIC) systems are used, the modifier may be a salt, such as the sodium chloride or ammonium sulphate concentration in the feed stream. If a reverse-phase chromatography system is used the modifier may be the organic solvent, such as ethanol, methanol, propanol or acetonitrile. In some aspects of the invention, the pH of the feed stream is the modifier.

In some aspects of the present invention the modifier is a salt component selected from any organic or inorganic salt and mixtures thereof, such as NaCl (sodium chloride), KCl (potassium chloride, $NH_4Cl$ (ammonium chloride), $CaCl_2$ (calcium chloride), sodium acetate, potassium acetate, ammonium acetate, sodium citrate, potassium citrate, ammonium citrate, sodium sulphate, potassium sulphate, ammonium sulphate, calcium acetate or mixtures thereof, Each of these salt components constitutes an alternative aspect of the present invention. Suitable salts are also disclosed in e.g. WO 2000/055184 or WO 00/55203, which is hereby incorporated by reference.

When the modifier is a salt component, concentration of the salt is the concentration of salt in the solvent. In ion exchange, the salt concentration is the concentration of counter ions to the ion exchange chromatography system. The salt concentration is in this case both counter ions added as the salt but also counter ions added during titration. This includes the counter ions added to the solvent e.g. when pH is adjusted in the solvent. In IEX being an anion exchange chromatography system, the salt concentration is the concentration of the anion. This includes e.g. both chloride added from NaCl and chloride added during pH-adjustment of the solvent using HCl. Similarly in IEX being a cation exchange chromatography system, the salt concentration is the concentration of the cation.

In one aspect, the solvent used in the methods of the present invention is an aqueous solvent comprising water and an organic component. Typical organic components include acetonitrile or alcohols.

In one aspect, the modifier is an organic component which is an alcohol, and in one aspect, the solvent is a mixture of water and an alcohol. Particular mentioning is made of mono-alcohols, i.e. alcohols comprising only one alcohol group. Examples of mono-alcohols which can be used in the methods of the present invention include methanol, ethanol, 1-propanol and 2-propanol, and mixtures of two or more thereof. It is regarded as an additional advantage to use alcohols rather than acetonitrile due to the well-established environmental and occupational health problems connected to the use of acetonitrile. The proteins are eluted with an increasing hydrophobicity of the solvent, i.e. by increasing the concentration of the organic compound. The concentration of the solvent used to load the protein on to the column depends on the nature of the protein and the hydrophobicity of the organic compound. This solvent is often referred to as the equilibration solvent as the column has typically been washed or equilibrated with one or more column volumes of this solvent prior to the loading of the protein to the column. A typical concentration of the organic compound in the equilibrating solvents is from 0-80%, such as 10-70%, 10-60%, or 20-50% of the solvent. The concentration is upward limited by the denaturing effect of the organic component. If the concentration is too high, there is a risk that the protein may irreversible denature. During elution of the protein in fixed bed chromatography, the concentration of the organic component in the solvent is raised, typically to concentrations from 5-96%, such as 10-95%, 20-90%, 30-90%, or 30-80%. Suitable organic modifiers are disclosed in WO/2007/071768, which is hereby incorporated by reference.

With the term "isotherm" is herein meant adsorption isotherm and refers to the concentrations of the adsorbed component at a given concentration of the same component in the liquid phase in a given solvent system. Usually the isotherm is depicted as a graph, see FIG. 2. Two common adsorption isotherms met in chromatography are the Langmuir adsorption isotherm and the Freundlich adsorption isotherm. At low concentrations of a component, a linear isotherm can be assumed. For a linear isotherm the concentration between the adsorbed component and the concentration in the mobile phase is constant.

The term "initial slope" when used in connection with the isotherm is herein used to describe the slope of the isotherm as the concentration of the component approaches 0 (zero), see FIG. 2.

The term "operating line" as used herein refers to the line of operation connecting the total mass or volumetric flow in one section of the plant with the total mass or volume flow in another section to which it is connected with a fluid. One example of an operating line can be seen in FIG. 8, where the line $m^{III}$ which is the dimensionless volumetric flow in zone III is a function of the feed flow, $Q^F$, and the dimensionless flow in zone II, $m^{II}$.

The terms "about" or "approximately" as used herein means in reasonable vicinity of the stated numerical value, such as plus or minus 10%, or for pH values plus or minus 0.2.

In one aspect of the invention the initial slope of the isotherm is about parallel with the slope of the operating line when a plot is made of $m^{III}$ & A as a function of $Q^F$, wherein "about" when used in connection with parallel means that the slope of the isotherm may vary slightly from the slope of the operating line such as up to 10% from the slope of the operating line. In one aspect the slope of the isotherm is within 10% of the slope of the operating line, in another aspect within 8% from the slope of the operating line, in another aspect within 6% from the slope of the operating line, in another aspect within 5% from the slope of the operating line, in another aspect within 3% from the slope of the operating line and in yet another aspect within 2% from the slope of the operating line.

The term "glucagon-like peptide" as used herein means the glucagon family of peptides, exendins and analogues and derivatives thereof. The glucagon family of peptides are encoded by the pre-proglucagon gene and encompasses three small peptides with a high degree of homology, i.e. glucagon (1-29), GLP-1 (1-37) and GLP-2 (1-33). Exendins are peptides expressed in lizards and like GLP-1, are insulinotropic. Examples of exendins are exendin-3 and exendin-4.

The term "analogue" as used herein refers to a modified glucagon-like peptide wherein one or more amino acid residues of the glucagon-like peptide have been substituted by other amino acid residues and/or wherein one or more amino acid residues have been deleted from the glucagon-like peptide and/or wherein one or more amino acid residues have been added to the glucagon-like peptide. Such addition or deletion of amino acid residues can e.g. take place at the N-terminal of the glucagon-like peptide and/or at the C-terminal of the peptide. A simple system is used to describe analogues: for example $Arg^{34}$-GLP-1(7-37) designates a GLP-1(7-37) analogue wherein the naturally occurring lysine at position 34 has been substituted with arginine. All amino acids for which the optical isomer is not stated is to be understood to mean the L-isomer. Likewise, standard single letter abbreviation for amino acids is used according to IUPAC-IUB nomenclature.

In one aspect an analogue according to the invention comprises up to 17 modifications (substitutions, deletions, additions) relative to the glucagon-like peptide. In one aspect an analogue comprises less than 16 modifications (substitutions, deletions, additions) relative to the glucagon-like peptide. In one aspect an analogue comprises less than 15 modifications (substitutions, deletions, additions) relative to the glucagon-like peptide. In another aspect an analogue comprises less than 14 modifications (substitutions, deletions, additions) relative to the glucagon-like peptide. In another aspect an analogue comprises less than 13 modifications (substitutions, deletions, additions) relative to the glucagon-like peptide. In another aspect an analogue comprises less than 12 modifications (substitutions, deletions, additions) relative to the glucagon-like peptide. In another aspect an analogue comprises less than 11 modifications (substitutions, deletions, additions) relative to the glucagon-like peptide. In another aspect an analogue comprises less than 10 modifications (substitutions, deletions, additions) relative to the glucagon-like peptide. In another aspect an analogue comprises less than 9 modifications (substitutions, deletions, additions) relative to the glucagon-like peptide. In another aspect an analogue comprises less than 8 modifications (substitutions, deletions, additions) relative to the glucagon-like peptide. In one aspect an analogue comprises less than 7 modifications (substitutions, deletions, additions) relative to the glucagon-like peptide. In one aspect an analogue comprises less than 6 modifications (substitutions, deletions, additions) relative to the glucagon-like peptide. In another aspect an analogue comprises less than 5 modifications (substitutions, deletions, additions) relative to the glucagon-like peptide. In another aspect an analogue comprises less than 4 modifications (substitutions, deletions, additions) relative to the glucagon-like peptide. In another aspect an analogue comprises less than 3 modifications (substitutions, deletions, additions) relative to the glucagon-like peptide. In another aspect an analogue comprises less than 2 modifications (substitutions, deletions, additions) relative to the glucagon-like peptide.

The term "lipophilically modified peptide" as used herein is a peptide comprising one or more lipophilic groups, such as lipophilic sidechains, covalently attached to one or more amino acids of the peptide. In one aspect according to the invention a lipophilic group is a lipophilic sidechain. The peptide that is lipophilically modified may be prepared by any suitable methodology, for example by attaching the lipophilic group(s) by conjugation chemistry such as by alkylation, acylation, ester formation, amide formation or maleimide coupling. In one aspect according to the present invention, the lipophilically modified peptides according to the invention have substantially the same activity relative to the same peptide, which is not lipophilically modified.

In one aspect, the lipophilically modified glucagon-like peptide to be included in the pharmaceutical composition of the present invention, is a GLP-1 agonist composed of at least five constituent amino acids connected by peptide bonds and an acyl group attached thereof.

The term "GLP-1 agonist" as used herein refers to any lipophilically modified glucagon-like peptide which fully or partially activates the human GLP-1 receptor. In a preferred aspect, the "GLP-1 agonist" is any lipophilically modified glucagon-like peptide that binds to a GLP-1 receptor, preferably with an affinity constant (KD) or a potency ($EC_{50}$) of below 1 μM, e.g., below 100 nM as measured by methods known in the art (see e.g., WO 98/08871) and exhibits insulinotropic activity, where insulinotropic activity may be measured in vivo or in vitro assays known to those of ordinary skill in the art. For example, the GLP-1 agonist may be administered to an animal and the insulin concentration measured over time.

In one aspect, the lipophilically modified glucagon-like peptide of the present invention is acylated, i.e., it has an acyl group attached, as the lipophilical modification.

An acyl group (IUPAC name: alkanoyl) is a functional group derived by the removal of one or more hydroxyl groups from an oxoacid. In organic chemistry, the acyl group is usually derived from a carboxylic acid of the form RCOOH. It therefore has the formula RC(=O)—, with a double bond between the carbon and oxygen atoms (i.e., a carbonyl group), and a single bond between R and the carbon. Acyl groups can also be derived from other types of acids such as sulfonic acids, phosphonic acids, and others.

In the acylated modified glucagon-like peptide compounds of the invention, the acyl group contains a functional group which can be attached to one of the following functional groups of an amino acid of the parent glucagon-like peptide:

(a) the amino group attached to the alpha-carbon of the N-terminal amino acid,
(b) the carboxy group attached to the alpha-carbon of the C-terminal amino acid,
(c) the epsilon-amino group of any Lys residue,
(d) the carboxy group of the R group of any Asp and Glu residue,
(e) the hydroxy group of the R group of any Tyr, Ser and Thr residue,
(f) the amino group of the R group of any Trp, Asn, Gln, Arg, and H is residue, or
(g) the thiol group of the R group of any Cys residue.

In one aspect, the acyl group is attached to the carboxy group of the R group, i.e., the side chain of any Asp and Glu residue. In another aspect, the acyl group is attached to the carboxy group attached to the alpha-carbon of the C-terminal amino acid. In yet another aspect, the acyl group is attached to the epsilon-amino group of any Lys residue.

In one aspect of the invention, the acyl group is attached to the parent glucagon-like peptide by means of a spacer. A spacer must contain at least two functional groups, one to attach to a functional group of the acyl group and the other to a functional group of the parent glucagon-like peptide.

In one aspect, the acyl group is a straight-chain or branched fatty acid. In one aspect, the acyl group has the formula $CH_3(CH_2)_nCO—$, wherein n is an integer from 4 to 38, such as an integer from 12 to 38. In one aspect the acyl group is selected from the group consisting of: $CH_3(CH_2)_{12}CO—$, $CH_3(CH_2)_{14}CO—$, $CH_3(CH_2)_{16}CO—$, $CH_3(CH_2)_{18}CO—$, $CH_3(CH_2)_{20}CO—$ and $CH_3(CH_2)_{22}CO—$. In another aspect, the acyl group is tetradecanoyl. In yet another aspect, the acyl group is hexadecanoyl.

In a further aspect of the present invention, the acyl group has a group which is negatively charged such as a carboxylic acid group. For example, the acyl group may be a straight-chain or branched alkane α,ω-dicarboxylic acid of the formula $HOOC(CH_2)_mCO—$, wherein m is an integer from 4 to 38, such as an integer from 12 to 38. In one aspect the acyl group is selected from the group consisting of: $HOOC(CH_2)_{14}CO—$, $HOOC(CH_2)_{16}CO—$, $HOOC(CH_2)_{18}CO—$, $HOOC(CH_2)_{20}CO—$ or $HOOC(CH_2)_{22}CO—$.

In one aspect, the spacer is an amino acid residue except Cys or Met, or a dipeptide such as Gly-Lys. For purposes of the present invention, the phrase "a dipeptide such as Gly-Lys" means any combination of two amino acids except Cys or Met, in one aspect a dipeptide wherein the C-terminal amino acid residue is Lys, H is or Trp, such as Lys, and the N-terminal amino acid residue is Ala, Arg, Asp, Asn, Gly, Glu, Gln, Ile, Leu, Val, Phe, Pro, Ser, Tyr, Thr, Lys, His and Trp. In one aspect, an amino group of the parent peptide forms an amide bond with a carboxylic group of the amino acid residue or dipeptide spacer, and an amino group of the amino acid residue or dipeptide spacer forms an amide bond with a carboxyl group of the acyl group.

Examples of spacers according to the invention include lysyl, glutamyl, asparagyl, glycyl, beta-alanyl and gamma-aminobutanoyl, each of which constitutes an individual aspect. In one aspect spacers are glutamyl and beta-alanyl.

When the spacer is Lys, Glu or Asp, the carboxyl group thereof may form an amide bond with an amino group of the amino acid residue, and the amino group thereof may form an amide bond with a carboxyl group of the acyl group. When Lys is used as the spacer, a further spacer may in some instances be inserted between the ε-amino group of Lys and the acyl group. In one aspect, such a further spacer is succinic acid which forms an amide bond with the ε-amino group of Lys and with an amino group present in the acyl group. In another aspect such a further spacer is Glu or Asp which forms an amide bond with the ε-amino group of Lys and another amide bond with a carboxyl group present in the acyl group, that is, the acyl group is a $N^ε$-acylated lysine residue.

In another aspect, the spacer is an unbranched alkane α,ω-dicarboxylic acid group having from 1 to 7 methylene groups, which spacer forms a bridge between an amino group of the parent peptide and an amino group of the substituent. In one aspect the spacer is succinic acid.

In a further aspect, the acyl group with the attached spacer is a group of the formula $CH_3(CH_2)_pNH—CO(CH_2)_qCO—$, wherein p is an integer from 8 to 33, alternatively from 12 to 28 and q is an integer from 1 to 6, alternatively 2.

In a further aspect, the acyl group with the attached spacer is a group of the formula $CH_3(CH_2)_nCO—NHCH(COOH)(CH_2)_2CO—$, wherein r is an integer from 4 to 24, such as from 10 to 24.

In a further aspect, the acyl group with the attached spacer is a group of the formula $CH_3(CH_2)_nCO—NHCH((CH_2)_2COOH)CO—$, wherein s is an integer from 4 to 24, such as from 10 to 24.

In a further aspect, the acyl group is a group of the formula $COOH(CH_2)_tCO—$ wherein t is an integer from 6 to 24.

In a further aspect, the acyl group with the attached spacer is a group of the formula $—NHCH(COOH)(CH_2)_4NH—CO(CH_2)_uCH_3$, wherein u is an integer from 8 to 18.

In a further aspect, the acyl group with the attached spacer is a group of the formula $CH_3(CH_2)_vCO—NH—(CH_2)_z—CO$, wherein v is an integer from 4 to 24 and z is an integer from 1 to 6.

In a further aspect, the acyl group with the attached spacer is a group of the formula $—NHCH(COOH)(CH_2)_4NH—COCH((CH_2)_2COOH)NH—CO(CH_2)_wCH_3$, wherein w is an integer from 10 to 16.

In a further aspect, the acyl group with the attached spacer is a group of the formula $—NHCH(COOH)(CH_2)_4NH—CO(CH_2)_2CH(COOH)NHCO(CH_2)_xCH_3$, wherein x is zero or an integer from 1 to 22, such as 10 to 16.

The invention also provides, an lipophilically modified glucagon-like peptide wherein the glucagon-like peptide is a GLP-1(7-37) analogue, which comprises the amino acid sequence of the formula (I) (SEQ ID NO: 1)

$X_7$-$X_8$-Glu-Gly-Thr-Phe-Thr-Ser-Asp-$X_{16}$-Ser-$X_{18}$-$X_{19}$-

$X_{20}$-Glu-$X_{22}$-$X_{23}$-Ala-$X_{25}$-$X_{26}$-$X_{27}$-Phe-Ile-$X_{30}$-Trp-

Leu-$X_{33}$-$X_{34}$-$X_{35}$-$X_{36}$-$X_{37}$-$X_{38}$-$X_{39}$-$X_{40}$-$X_{41}$-$X_{42}$-$X_{43}$-

$X_{44}$-$X_{45}$-$X_{46}$ wherein:

$X_7$ (position no. 1 in SEQ ID NO: 1) is L-histidine, D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine or 4-pyridylalanine;

$X_8$ (position no. 2 in SEQ ID NO: 1) is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

$X_{16}$ (position no. 10 in SEQ ID NO: 1) is Val or Leu;
$X_{18}$ (position no. 12 in SEQ ID NO: 1) is Ser, Lys or Arg;
$X_{19}$ (position no. 13 in SEQ ID NO: 1) is Tyr or Gln;
$X_{20}$ (position no. 14 in SEQ ID NO: 1) is Leu, Met or Lys;
$X_{22}$ (position no. 16 in SEQ ID NO: 1) is Gly, Glu or Aib;
$X_{23}$ (position no. 17 in SEQ ID NO: 1) is Gln, Glu, Lys or Arg;
$X_{25}$ (position no. 19 in SEQ ID NO: 1) is Ala or Val;
$X_{26}$ (position no. 20 in SEQ ID NO: 1) is Lys, Glu or Arg;
$X_{27}$ (position no. 21 in SEQ ID NO: 1) is Glu or Leu;
$X_{30}$ (position no. 24 in SEQ ID NO: 1) is Ala, Glu, Lys or Arg;
$X_{33}$ (position no. 27 in SEQ ID NO: 1) is Val or Lys;
$X_{34}$ (position no. 28 in SEQ ID NO: 1) is Lys, Glu, Asn or Arg;
$X_{35}$ (position no. 29 in SEQ ID NO: 1) is Gly or Aib;
$X_{36}$ (position no. 30 in SEQ ID NO: 1) is Arg, Gly or Lys;
$X_{37}$ (position no. 31 in SEQ ID NO: 1) is Gly, Ala, Glu, Pro, Lys, amide or is absent;
$X_{38}$ (position no. 32 in SEQ ID NO: 1) is Lys, Ser, amide or is absent.
$X_{39}$ (position no. 33 in SEQ ID NO: 1) is Ser, Lys, amide or is absent;
$X_{40}$ (position no. 34 in SEQ ID NO: 1) is Gly, amide or is absent;
$X_{41}$ (position no. 35 in SEQ ID NO: 1) is Ala, amide or is absent;
$X_{42}$ (position no. 36 in SEQ ID NO: 1) is Pro, amide or is absent;
$X_{43}$ (position no. 37 in SEQ ID NO: 1) is Pro, amide or is absent;
$X_{44}$ (position no. 38 in SEQ ID NO: 1) is Pro, amide or is absent;
$X_{45}$ (position no. 39 in SEQ ID NO: 1) is Ser, amide or is absent;
$X_{46}$ (position no. 40 in SEQ ID NO: 1) is amide or is absent; provided that if $X_{38}$, $X_{39}$, $X_{40}$, $X_{41}$, $X_{42}$, $X_{43}$, $X_{44}$, $X_{45}$ or $X_{46}$ (position no. 32 to 40 in SEQ ID NO: 1, respectively) is absent then each amino acid residue downstream is also absent.

In one aspect of the invention, the lipophilically modified glucagon-like peptide is an GLP-1 analogue selected from the group consisting of $Arg^{34}GLP-1(7-37)$, $Lys^{38}Arg^{26,34}GLP-1(7-38)$, $Lys^{38}Arg^{26,34}GLP-1(7-38)$-OH, $Lys^{36}Arg^{26,34}GLP-1(7-36)$, $Aib^{8,22,35}$ GLP-1(7-37), $Aib^{8,35}$ GLP-1(7-37), $Aib^{8,22}$ GLP-1(7-37), $Aib^{8,22,35}$ $Arg^{26,34}Lys^{38}GLP-1(7-38)$, $Aib^{8,35}$ $Arg^{26,34}Lys^{38}GLP-1(7-38)$, $Aib^{8,22}$ $Arg^{26,34}Lys^{38}GLP-1(7-38)$, $Aib^{8,22,35}$ $Arg^{26,34}Lys^{38}GLP-1(7-38)$, $Aib^{8,35}$ $Arg^{26,34}Lys^{38}GLP-1(7-38)$, $Aib^{8,22,35}$ $Arg^{26}Lys^{38}GLP-1(7-38)$, $Aib^{8,35}$ $Arg^{26}Lys^{38}GLP-1(7-38)$, $Aib^{8,22}$ $Arg^{26}Lys^{38}GLP-1(7-38)$, $Aib^{8,22,35}$ $Arg^{34}Lys^{38}GLP-1(7-38)$, $Aib^{8,35}$ $Arg^{34}Lys^{38}GLP-1(7-38)$, $Aib^{8,22}$ $Arg^{34}Lys^{38}GLP-1(7-38)$, $Aib^{8,22,35}$ $Ala^{37}Lys^{38}GLP-1(7-38)$, $Aib^{8,35}Ala^{37}Lys^{38}GLP-1(7-38)$, $Aib^{8,22}Ala^{37}Lys^{38}GLP-1(7-38)$, $Aib^{8,22,35}$ $Lys^{37}GLP-1(7-37)$, $Aib^{8,35}$ $Lys^{37}GLP-1(7-37)$, $Aib^{8}Arg^{34}GLP-1(7-37)$ and $Aib^{8,22}Lys^{37}GLP-1(7-38)$, when said GLP-1 analogue is acylated.

In one aspect of the invention, the lipophilically modified glucagon-like peptide is an acylated GLP-1 analogue, which is selected from the group consisting of:
[desaminoHis7,Glu22,Arg26,Arg34,Lys37]GLP-1(7-37) amide,
[desaminoHis$^7$,Arg$^{34}$]GLP-1-(7-37), [Aib$^8$,Glu$^{22}$,Arg$^{26}$, Arg$^{34}$,Lys$^{37}$]GLP-1-(7-37)amide,
[DesaminoHis$^7$, Glu$^{22}$ Arg$^{26}$, Arg$^{34}$, Phe(m-CF3)$^{28}$]GLP-1-(7-37)amide,
[DesaminoHis$^7$,Glu$^{22}$,Arg$^{26}$,Arg$^{34}$]GLP-1-(7-37)-Lys,
[DesaminoHis$^7$,Glu$^{22}$,Arg$^{26}$,Arg$^{34}$]GLP-1-(7-37)-Lys,
[desaminoHis$^7$,Arg$^{26}$,Arg$^{34}$,]GLP-1-(7-37)-Lys,
[DesaminoHis$^7$,Glu$^{22}$,Arg$^{26}$,Arg$^{34}$,Lys$^{37}$]GLP-1-(7-37) amide,
[DesaminoHis$^7$,Arg$^{26}$,Arg$^{34}$,Lys$^{37}$]GLP-1-(7-37)amide,
[DesaminoHis$^7$,Glu$^{22}$,Arg$^{26}$,Arg$^{34}$,Lys$^{37}$]GLP-1-(7-37),
[DesaminoHis$^7$,Arg$^{26}$,Arg$^{34}$,Lys$^{37}$]GLP-1-(7-37),
[DesaminoHis$^7$,Glu$^{22}$,Arg$^{26}$,Glu$^{30}$,Arg$^{34}$,Lys$^{37}$]GLP-1-(7-37),
[Aib$^8$,Lys$^{20}$,Arg$^{26}$,Glu$^{30}$,Thr(O-benzyl)$^{33}$,]GLP-1-(7-37) amide,
[Aib$^8$,Glu$^{22}$,Arg$^{26}$,Lys$^{30}$]GLP-1-(7-37), [Aib$^8$, Glu$^{22}$, Arg$^{26}$,Lys$^{31}$]GLP-1-(7-37),
[Aib$^8$,Lys$^{20}$,Arg$^{26}$,2-Naphtylalanine$^{28}$, Glu$^{30}$,]GLP-1 (7-37) amide,
[Aib$^8$, Glu$^{22}$, Arg$^{26}$, Arg$^{34}$,]GLP-1-(7-37)-Lys,
[Aib$^8$,Lys$^{20}$,Arg$^{26}$, 2-Naphtylalanine12, Glu$^{30}$,]GLP-1-(7-37)amide,
[Aib$^8$,Glu$^{22}$,Arg$^{26}$,Lys$^{31}$,Arg$^{34}$]GLP-1-(7-37),
[Aib$^8$,Arg$^{34}$]GLP-1-(7-37),
[Aib$^8$,Arg$^{34}$]GLP-1-(7-37)-amide,
[Aib$^8$,Lys$^{18}$,Arg$^{26}$,Arg$^{34}$]GLP-1-(7-37),
[Aib$^8$,Glu$^{22}$,Arg$^{26}$,Arg$^{34}$,Lys$^{37}$]GLP-1-(7-37)amide,
[Aib$^8$, Lys$^{26}$]GLP-1 (7-37)amide,
[Aib$^8$,Arg$^{34}$]GLP-1-(7-34),
[Aib$^8$,Arg$^{34}$]GLP-1-(7-35),
[Aib$^8$,Lys$^{33}$,Arg$^{34}$]GLP-1-(7-34),
[Aib$^8$,Arg$^{34}$]GLP-1-(7-36)amide,
[Aib$^8$,Lys$^{26}$,Arg$^{34}$]GLP-1-(7-36)amide,
[Aib$^8$,Glu$^{22}$,Arg$^{26}$,Arg$^{34}$]GLP-1-(7-37)Lys,
[Aib$^8$,Lys$^{20}$,Glu$^{22}$,Arg$^{26}$,Glu$^{30}$,Pro$^{37}$]GLP-1-(7-37)amide,
[Aib$^8$,Glu$^{22}$,Arg$^{26}$,Arg$^{34}$,Lys$^{37}$]GLP-1-(7-37)amide,
[DesaminoHis$^7$,Glu$^{22}$,Arg$^{26}$,Arg$^{34}$,Lys$^{37}$]GLP-1-(7-37) amide,
[DesaminoHis$^7$,Arg$^{26}$,Arg$^{34}$,Lys$^{37}$]GLP-1-(7-37)amide,
Aib$^8$,Glu$^{22}$,Arg$^{26}$,Glu$^{30}$,Pro$^{37}$]GLP-1-(7-37)Lys,
[Aib$^8$,Glu$^{22}$,Arg$^{26}$,Glu$^{30}$,Pro$^{37}$]GLP-1-((7-37)Lys,
[Aib$^8$,Arg$^{26}$,Arg$^{34}$]GLP-1-(7-37),
$Arg^{34}GLP-1(7-37)$, and
$Gly^8$-GLP-1(7-36), when said GLP-1 analogue is acylated.

In yet another aspect the lipophilically modified glucagon-like peptide is an acylated GLP-1 agonist, which is selected from the group consisting of $Gly^8$-GLP-1(7-36)-amide, $Gly^8$-GLP-1(7-37), $Val^8$-GLP-1(7-36)-amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37) and analogues thereof.

In yet another aspect the lipophilically modified glucagon-like peptide is an acylated GLP-1 agonist is selected from the group consisting of $Arg^{26}$-GLP-1(7-37); $Arg^{34}$-GLP-1(7-37); $Lys^{36}$-GLP-1(7-37); $Arg^{26,34}Lys^{36}$-GLP-1(7-37); $Arg^{26,34}$-GLP-1(7-37); $Arg^{26,34}Lys^{40}$-GLP-1(7-37); $Arg^{26}Lys^{36}$-GLP-1(7-37); $Arg^{34}Lys^{36}$-GLP-1(7-37); $Val^8Arg^{22}$-GLP-1(7-37); $Met^8Arg^{22}$-GLP-1(7-37);

Gly⁸His²²-GLP-1(7-37); Val⁸His²²-GLP-1(7-37); Met⁸His²²-GLP-1(7-37); His³⁷-GLP-1(7-37); Gly⁸-GLP-1(7-37); Val⁸-GLP-1(7-37); Met⁸-GLP-1(7-37); Gly⁸Asp²²-GLP-1(7-37); Val⁸Asp²²-GLP-1(7-37); Met⁸Asp²²-GLP-1(7-37); Gly⁸Glu²²-GLP-1(7-37); Val⁸Glu²²-GLP-1(7-37); Met⁸Glu²²-GLP-1(7-37); Gly⁸Lys²²-GLP-1(7-37); Val⁸Lys²²-GLP-1(7-37); Met⁸Lys²²-GLP-1(7-37); Gly⁸Arg²²-GLP-1(7-37); Val⁸Lys²²His³⁷-GLP-1(7-37); Gly⁸Glu²²His³⁷-GLP-1(7-37); Val⁸Glu²²His³⁷-GLP-1(7-37); Met⁸Glu²²His³⁷-GLP-1(7-37); Gly⁸Lys²²His³⁷-GLP-1(7-37); Met⁸Lys²²His³⁷-GLP-1(7-37); Gly⁸Arg²²His³⁷-GLP-1(7-37); Val⁸Arg²²His³⁷-GLP-1(7-37); Met⁸Arg²²His³⁷-GLP-1(7-37); Gly⁸His²²His³⁷-GLP-1(7-37); Val⁸His²²His³⁷-GLP-1(7-37); Met⁸His²²His³⁷-GLP-1(7-37); Gly⁸His³⁷-GLP-1(7-37); Val⁸His³⁷-GLP-1(7-37); Met⁸His³⁷-GLP-1(7-37); Gly⁸Asp²²His³⁷-GLP-1(7-37); Val⁸Asp²²His³⁷-GLP-1(7-37); Met⁸Asp²²His³⁷-GLP-1(7-37); Arg²⁶-GLP-1(7-36)-amide; Arg³⁴-GLP-1(7-36)-amide; Lys³⁶-GLP-1(7-36)-amide; Arg²⁶,³⁴Lys³⁶-GLP-1(7-36)-amide; Arg²⁶,³⁴-GLP-1(7-36)-amide; Arg²⁶,³⁴Lys⁴⁰-GLP-1(7-36)-amide; Arg²⁶Lys³⁶-GLP-1(7-36)-amide; Arg³⁴Lys³⁶-GLP-1(7-36)-amide; Gly⁸-GLP-1(7-36)-amide; Val⁸-GLP-1(7-36)-amide; Met⁸-GLP-1(7-36)-amide; Gly⁸Asp²²-GLP-1(7-36)-amide; Gly⁸Glu²²His³⁷-GLP-1(7-36)-amide; Val⁸Asp²²-GLP-1(7-36)-amide; Met⁸Asp²²-GLP-1(7-36)-amide; Gly⁸Glu²²-GLP-1(7-36)-amide; Val⁸Glu²²-GLP-1(7-36)-amide; Met⁸Glu²²-GLP-1(7-36)-amide; Gly⁸Lys²²-GLP-1(7-36)-amide; Val⁸Lys²²-GLP-1(7-36)-amide; Met⁸Lys²²-GLP-1(7-36)-amide; Gly⁸His²²His³⁷-GLP-1(7-36)-amide; Gly⁸Arg²²-GLP-1(7-36)-amide; Val⁸Arg²²-GLP-1(7-36)-amide; Met⁸Arg²²-GLP-1(7-36)-amide; Gly⁸His²²-GLP-1(7-36)-amide; Val⁸His²²-GLP-1(7-36)-amide; Met⁸His²²-GLP-1(7-36)-amide; His³⁷-GLP-1(7-36)-amide; Val⁸Arg²²His³⁷-GLP-1(7-36)-amide; Met⁸Arg³⁷-GLP-1(7-36)-amide; Gly⁸His³⁷-GLP-1(7-36)-amide; Val⁸His³⁷-GLP-1(7-36)-amide; Met⁸His³⁷-GLP-1(7-36)-amide; Gly⁸Asp²²His³⁷-GLP-1(7-36)-amide; Val⁸Asp²²His³⁷-GLP-1(7-36)-amide; Met⁸Asp²²His³⁷-GLP-1(7-36)-amide; Val⁸Glu²²His³⁷-GLP-1(7-36)-amide; Met⁸Glu²²His³⁷-GLP-1(7-36)-amide; Gly⁸Lys²²His³⁷-GLP-1(7-36)-amide; Val⁸Lys²²His³⁷-GLP-1(7-36)-amide; Met⁸Lys²²His³⁷-GLP-1(7-36)-amide; Gly⁸Arg²²His³⁷-GLP-1(7-36)-amide; Val⁸His²²His³⁷-GLP-1(7-36)-amide; Met⁸His²²His³⁷-GLP-1(7-36)-amide and analogues thereof.

In yet another aspect the acylated GLP-1 agonist is selected from the group consisting of Val⁸Trp¹⁹Glu²²-GLP-1(7-37), Val⁸Glu²²Val²⁵-GLP-1(7-37), Val⁸Tyr¹⁶Glu²²-GLP-1(7-37), Val⁸Trp¹⁶Glu²²-GLP-1(7-37), Val⁸Leu¹⁶Glu²²-GLP-1(7-37), Val⁸Tyr¹⁸Glu²²-GLP-1(7-37), Val⁸Glu²²His³⁷-GLP-1(7-37), Val⁸Glu²²Ile³³-GLP-1(7-37), Val⁸Trp¹⁶Glu²²Val²⁵Ile³³-GLP-1(7-37), Val⁸Trp¹⁶Glu²²Ile³³-GLP-1(7-37), Val⁸Glu²²Val²⁵Ile³³-GLP-1(7-37), Val⁸Trp¹⁶Glu²²Val²⁵-GLP-1(7-37) and analogues thereof.

In yet another aspect the lipophilically modified glucagon-like peptide as used herein means acylated GLP-1(7-37) (SEQ ID NO. 1) and insulinotropic analogues thereof. Non-limiting examples of GLP-1 analogues and acylated GLP-1 analogues are GLP-1(7-36) amide, Arg³⁴-GLP-1(7-37), Gly⁸-GLP-1(7-37), Val⁸-GLP-1(7-36)-amide, Val⁸Asp²²-GLP-1(7-37), desamino-His⁷, Arg²⁶, Lys³⁴(Nᵋ-(γ-Glu(Nᵅ-hexadecanoyl)))-GLP-1(7-37), desamino-His⁷, Arg²⁶, Lys³⁴(Nᵋ-octanoyl)-GLP-1(7-37), Arg²⁶,³⁴, Lys³⁸(Nᵋ-(ω-carboxypentadecanoyl))-GLP-1(7-38), Arg²⁶,³⁴ Lys³⁶(Nᵋ-(γ-Glu(Nᵅ-hexadecanoyl)))-GLP-1(7-36) and Arg³⁴, Lys²⁶(Nᵋ-(γ-Glu(Nᵅ-hexadecanoyl)))-GLP-1(7-37).

In one aspect the lipophilically modified glucagon-like peptide of the present invention is dipeptidyl aminopeptidase IV protected. The term "dipeptidyl aminopeptidase IV protected" as used herein means a compound, e.g. an acylated GLP-1 analogue, which is more resistant to dipeptidyl aminopeptidase IV (DPP-IV) than the native compound, e.g. GLP-1(7-37). Resistance of a lipophilically modified glucagon-like peptide towards degradation by dipeptidyl aminopeptidase IV is determined by the degradation assay described below.

Aliquots of the lipophilically modified glucagon-like peptide (5 nmol) are incubated at 37° C. with 1 µl of purified dipeptidyl aminopeptidase IV corresponding to an enzymatic activity of 5 mU for 10-180 minutes in 100 µl of 0.1M triethylamine-HCl buffer, pH 7.4. Enzymatic reactions are terminated by the addition of 5 µl of 10% trifluoroacetic acid, and the peptide degradation products are separated and quantified using HPLC analysis. In one method for performing this analysis the mixtures are applied onto a Vydac C18 widepore (30 nm pores, 5 µm particles) 250×4.6 mm column and eluted at a flow rate of 1 ml/min with linear stepwise gradients of acetonitrile in 0.1% trifluoroacetic acid (0% acetonitrile for 3 min., 0-24% acetonitrile for 17 min., 24-48% acetonitrile for 1 min.) according to Siegel et al. [Regul. Pept. (1999) 79:93-102] and Mentlein et al. [Eur. J. Biochem. (1993) 214:829-35]. Peptides and their degradation products may be monitored by their absorbance at 220 nm (peptide bonds) or 280 nm (aromatic amino acids), and are quantified by integration of their peak areas related to those of standards. The rate of hydrolysis of a lipophilically modified glucagon-like peptide by dipeptidyl aminopeptidase IV is estimated at incubation times which result in less than 10% of the lipophilically modified glucagon-like peptide being hydrolysed.

In yet another aspect, the lipophilically modified glucagon-like peptide to be included in the pharmaceutical compositions of the present invention is lipophilically modified GLP-2 or an analogue thereof. Where the lipophilically modified glucagon-like peptide to be included in the pharmaceutical compositions of the present invention is lipophilically modified GLP-2 or an analogue thereof, the lipophilically modified GLP-2 or an analogue thereof is present in a concentration from about 1 mg/ml to about 100 mg/ml, more preferably in a concentration from about 1 mg/ml to about 10 mg/ml.

In yet another aspect the lipophilically modified glucagon-like peptide is lipophilically modified exendin-4 or lipophilically modified exendin-3 or analogues thereof. Examples of exendins as well as analogues thereof to be included within the present invention are those disclosed in WO 97/46584, U.S. Pat. No. 5,424,286 and WO 01/04156. U.S. Pat. No. 5,424,286 describe a method for stimulating insulin release with an exendin peptide. The exendin peptides disclosed include HGEGTFTSDLSKQMEEEAVR-LFIEWLKNGGX (SEQ ID NO. 2), wherein X—P or Y, and wherein exendin-3 is HSDGTFITSDLSKQMEEEAVR-LFIEWLKNGGPSSGAPPPS (SEQ ID NO. 3) and exendin-4 (1-39) is HGEGTFITSDLSKQMEEEAVR-LFIEWLKNGGPSSGAPPPS (SEQ ID NO. 4). WO 97/46584 describes truncated versions of exendin peptide(s). The disclosed peptides increase secretion and biosynthesis of insulin, but reduce those of glucagon. WO 01/04156 describes exendin-4 analogues and derivatives as well as the preparation of these molecules.

In one aspect, the exendin-4 analogue is HGEGTFTSDL-SKQMEEEAVRLFIEWLKNGGPSSGAPPSKKKKKK-amide (ZP-10) (SEQ ID NO. 5).

The term "exendin-4 peptide" as used herein means exendin-4(1-39) (SEQ ID NO. 4), an exendin-4(1-39) analogue, an exendin-4(1-39) derivative or a derivative of an exendin-4(1-39) analogue, insulinotropic fragments thereof, insulinotropic analogues thereof and insulinotropic derivatives thereof. Insulinotropic fragments of exendin-4 are insulinotropic peptides for which the entire sequence can be found in the sequence of exendin-4 (SEQ ID NO. 4) and where at least one terminal amino acid has been deleted. Examples of insulinotropic fragments of exendin-4(1-39) are exendin-4(1-38) and exendin-4(1-31).

The insulinotropic property of a compound may be determined by in vivo or in vitro assays well known in the art. For instance, the compound may be administered to an animal and monitoring the insulin concentration over time. Insulinotropic analogues of exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. An example of an insulinotropic analogue of exendin-4(1-39) is Ser$^2$Asp$^3$-exendin-4(1-39) wherein the amino acid residues in position 2 and 3 have been replaced with serine and aspartic acid, respectively (this particular analogue also being known in the art as exendin-3). Insulinotropic derivatives of exendin-4(1-39) and analogues thereof are what the person skilled in the art considers to be derivatives of these peptides, i.e., having at least one substituent which is not present in the parent peptide molecule with the proviso that said derivative either is insulinotropic or is a prodrug of an insulinotropic compound. Examples of substituents are amides, carbohydrates, alkyl groups, esters and lipophilic substituents. An example of an insulinotropic derivative of exendin-4(1-39) and analogues thereof is Tyr$^{31}$-exendin-4(1-31)-amide.

The term "stable exendin-4 compound" as used herein means a chemically modified exendin-4(1-39), i.e., an acylated exendin-3 or acylated exendin-4 analogue which exhibits an in vivo plasma elimination half-life of at least 10 hours in man, as determined by conventional methods.

In one aspect the lipophilically modified glucagon-like peptide of the present invention is insulinotropic. The term "insulinotropic" as used herein referring to a lipophilically modified glucagon-like peptide means the ability to stimulate secretion of insulin in response to an increased plasma glucose level. Insulinotropic peptides and compounds are agonists of the GLP-1 receptor. The insulinotropic property of a compound may be determined by in vitro or in vivo assays known in the art. The following in vitro assay may be used to determine the insulinotropic nature of a compound such as a peptide. Preferably insulinotropic compounds exhibit an EC$_{50}$ value in below assay of less than 5 nM, even more preferably EC$_{50}$ values less than 500 pM.

Baby hamster kidney (BHK) cells expressing the cloned human GLP-1 receptor (BHK 467-12A) are grown in DMEM media with the addition of 1001 U/ml penicillin, 100 µl/ml streptomycin, 10% foetal calf serum and 1 mg/ml Geneticin G-418 (Life Technologies). Plasma membranes are prepared by homogenization in buffer (10 mM Tris-HCl, 30 mM NaCl and 1 mM dithiothreitol, pH 7.4, containing, in addition, 5 mg/ml leupeptin (Sigma), 5 mg/l pepstatin (Sigma), 100 mg/l bacitracin (Sigma), and 16 mg/l aprotinin (Calbiochem-Novabiochem, La Jolla, Calif.)). The homogenate is centrifuged on top of a layer of 41% w/w sucrose. The white band between the two layers is diluted in buffer and centrifuged. Plasma membranes are stored at −80° C. until further use.

The functional receptor assay is carried out by measuring cAMP as a response to stimulation by the insulinotropic peptide or insulinotropic compound. Incubations are carried out in 96-well microtiter plates in a total volume of 140 ml and with the following final concentrations: 50 mM Tris-HCl, 1 mM EGTA, 1.5 mM MgSO$_4$, 1.7 mM ATP, 20 mM GTP, 2 mM 3-isobutyl-1-methylxanthine (IBMX), 0.01% w/v Tween-20, pH 7.4. Compounds are dissolved and diluted in buffer. GTP is freshly prepared for each experiment: 2.5 µg of membrane is added to each well and the mixture is incubated for 90 min. at room temperature in the dark with shaking. The reaction is stopped by the addition of 25 ml, 0.5M HCl. Formed cAMP is measured by a scintillation proximity assay (RPA 542, Amersham, UK). A dose-response curve is plotted for the compound and the EC$_{50}$ value is calculated using GraphPad Prism software.

The production of polypeptides and peptides, such as glucagon-like peptides to be lipophilically modified, is well known in the art. Polypeptides or peptides may for instance be produced by classical peptide synthesis, e.g. solid phase peptide synthesis using t-Boc or Fmoc chemistry or other well established techniques, see e.g. Greene and Wuts [Protective Groups in Organic Synthesis, John Wiley & Sons (1999)]. The polypeptides or peptides may also be produced by a method which comprises culturing a host cell containing a DNA sequence encoding the (poly)peptide and capable of expressing the (poly)peptide in a suitable nutrient medium under conditions permitting the expression of the peptide. For (poly)peptides comprising non-natural amino acid residues, the recombinant cell should be modified such that the non-natural amino acids are incorporated into the (poly)peptide, for instance by use of tRNA mutants.

The term "liraglutide" as used herein is used for the glucagon-like peptide (GLP-1) derivative, Arg$^{34}$,Lys$^{26}$(N$^{\epsilon}$-(γ-Glu(N$^{\alpha}$-hexadecanoyl)))-GLP-1(7-37).

As discussed above, the present invention relates to a method for the chromatographic separation of a polypeptide of interest from at least one further component in a fluid mixture, the method comprising
a) Providing a counter current purification system that comprises a plurality of sections in fluid connection, said sections comprising at least one solid phase and a first desorbent stream;
b) introducing said fluid mixture as the feed stream into said counter current purification system wherein the fluid mixture contacts the solid phase in a counter current mode;
c) controlling the isotherm by adjusting the concentration of at least one modifier in the feed stream so that the initial slope of the isotherm is about parallel with the slope of the operating line when a plot is made of m$^{III}$ & A as a function of Q$^F$ or α;
d) effecting separation of the polypeptide of interest from at least one further component; and
e) collecting the polypeptide of interest to provide a purified composition thereof.

In some aspects of the invention the concentration of at least one modifier in the feed stream is controlled to be different from the concentration of the same modifier in the desorbent stream.

In some aspects of the invention the polypeptide of interest is glucagon-like peptide and/or a GLP-1 agonist.

In some aspects of the invention the polypeptide of interest is GLP-1 (1-37) or an analogue or derivative thereof.

In some aspects of the invention the counter current purification system is an Ion Exchange Chromatography system.

In some aspects of the invention the Ion Exchange Chromatography system is an anion exchange system.

In some aspects of the invention the Ion Exchange Chromatography system is a cation exchange system.

In some aspects of the invention the isotherm is controlled so that the initial slope of the isotherm is about parallel with the slope of the operating line when a plot is made of $m^{III}$ & A as a function of $Q^F$ or $\alpha$. It is thus the belief of the inventor, that it is important for the efficiency of the method of the invention and thus the purity of the product obtained after purification according to the method of the invention, that the concentration of the modifier is controlled so as to obtain an isotherm which initial slope is within 10% of the slope of the operating line.

In some aspects of the invention the isotherm is controlled by the salt concentration in the feed stream, $c_s^F$.

In one aspect of the invention, the relative salt concentration in the feed stream relative to the salt concentration in the section prior to the feed stream (such as in zone II of FIG. 3) is in the range:

$$\frac{v_B - \alpha_{AB}^{III}}{v_B + 1/2 \cdot \alpha_{AB}^{III}} \leq \frac{c_s^F}{c_s^{II}} \leq \frac{v_A - 1/\alpha_{AB}^{III}}{v_A}$$

and the selectivity is given as $$\alpha_{AB} = \frac{A_A}{A_B} = \exp(\beta_A - \beta_B) \cdot c_s^{(\alpha_A - \alpha_B)},$$

where the parameters $\alpha_i$ and $\beta_i$ for components A and B are fitted to the retention volumes in a double logarithmic plot:

$$\ln(\tilde{V}_R - \tilde{V}_{NR}) = \alpha_i \cdot \ln(c_s) + \beta_i$$

In one aspect of the invention, the relative salt concentration in the feed stream relative to the salt concentration in the section prior to the feed stream is in the range:

$$0.39 \leq \frac{c_s^F}{c_s^{II}} \leq 0.80.$$

In one aspect of the invention, the chloride concentration in the feed stream, $c_s^F$, is in the range from about 17.5 mmol/kg to about 36 mmol/kg and the chloride concentration in the section prior to the feed stream such as section II is about 45 mmol/kg.

In one aspect of the invention, the chloride concentration in the feed stream, $c_s^F$, is in the range from about 21 mmol/kg to about 35 mmol/kg and the chloride concentration in the section prior to the feed stream such as section II is about 45 mmol/kg.

In one aspect of the invention, the chloride concentration in the feed stream, $c_s^F$, is in the range from about 24 mmol/kg to about 34 mmol/kg and the chloride concentration in the section prior to the feed stream such as section II is about 45 mmol/kg.

In one aspect of the invention, the chloride concentration in the feed stream, $c_s^F$, is in the range from about 28 mmol/kg to about 33 mmol/kg and the chloride concentration in the section prior to the feed stream such as section II is about 45 mmol/kg.

In one aspect of the invention, the chloride concentration in the feed stream, $c_s^F$, is in the range from about 87.1 mmol/kg to about 114.3 mmol/kg and the chloride concentration in the section prior to the feed stream such as section II is about 130 mmol/kg.

In one aspect of the invention, the chloride concentration in the feed stream, $c_s^F$, is in the range from about 99 mmol/kg to about 114 mmol/kg and the chloride concentration in the section prior to the feed stream such as section II is about 130 mmol/kg.

In some aspects of the invention the feed stream and the desorbent comprise a salt selected from any organic or inorganic salt and mixtures thereof, such as NaCl, KCl, $NH_4Cl$, $CaCl_2$, sodium acetate, potassium acetate, ammonium acetate, sodium citrate, potassium citrate, ammonium citrate, sodium sulphate, potassium sulphate, ammonium sulphate, calcium acetate or mixtures thereof. In one aspect of the invention the feed stream and the desorbent comprise NaCl.

In some aspects of the invention the counter current purification system is a Reverse Phase Chromatography (RPC) system.

In some aspects of the invention the counter current purification system is a Hydrophobic Interaction Chromatography (HIC) system.

In some aspects of the invention the feed stream and the desorbent comprises an inorganic salt, such as ammonium sulphate.

In some aspects of the invention the isotherm is controlled by the concentration of the organic modifier in the feed stream.

In one aspect of the invention, the difference between the organic modifier in the feed stream and the desorbent stream is in the range:

$$\frac{1 + 1/2}{K_{m,B}} \cdot \alpha_{AB}^{III} \leq c_m^F - c_m^{II} \leq \frac{1}{K_{m,A} \cdot \alpha_{AB}^{III}}$$

where the selectivity is given by:

$$\alpha_{AB} = \frac{A_A}{A_B} = \frac{\exp(\alpha_A \cdot c_m + \beta_A)}{\exp(\alpha_B \cdot c_m + \beta_B)} = \exp((\alpha_A - \alpha_B) \cdot c_m + (\beta_A - \beta_A))$$

and the parameters $\alpha_i$ and $\beta_i$ for component A and B are fitted to the retention volumes in a semi logarithmic plot (as e.g. seen in FIG. 21) of the function:

$$\ln(\tilde{V}_R - \tilde{V}_{NR}) = \alpha_i c_m + \beta_i$$

In one aspect of the invention, the difference between the organic modifier in the feed stream and the stream in the section prior to the feed stream (e.g. section II in FIG. 3), $c_m^F - c_m^{II}$, is $-3.5$ wt % $\leq c_m^F - c_m^{II} \leq -1.4$ wt %.

In one aspect of the invention the difference between the organic modifier in the feed stream and the stream in the section prior to the feed stream, $c_m^F - c_m^{II}$ is in the range from about 27.3 wt % to about 29.4 wt %, wherein the ethanol concentration in the section prior to the feed stream such as section II is about 30.8 wt %.

In one aspect of the invention the difference between the organic modifier in the feed stream and the stream in the section prior to the feed stream, $c_m^F - c_m^{II}$ is in the range from about 53.7 wt % to about 57.1 wt %, wherein the ethanol concentration in the section prior to the feed stream such as section II is about 58.4 wt %.

In some aspects of the invention the feed stream and the desorbent comprises an organic solvent, such as an organic solvent selected from ethanol, methanol, propanol and acetonitrile. In one aspect of the invention the feed stream and the desorbent comprise ethanol.

In some aspects of the invention the counter current purification system is using adsorption chromatography, partition chromatography, size exclusion chromatography, or affinity chromatography.

In some aspects of the invention the counter current purification system is a Simulated moving bed (SMB) purification system.

In some aspects of the invention the counter current purification system is a Multicolumn Counter Current Solvent Gradient Purification (MCSGP) system.

In some aspects of the invention the separation occurs under linear adsorption isotherms for at least one component.

In some aspects of the invention the feed stream composition remains constant throughout the procedure.

In some aspects of the invention the feed stream composition is changed during the procedure.

In some aspects of the invention the isotherm is controlled by adjustment of the concentration of at least one modifier in the feed stream.

In some aspects of the invention the isotherm is controlled by adjustment of the concentration of at least one modifier in the feed stream which leads to an operating line that lies between the initial slope of the isotherms for said polypeptide of interest and said at least one further component.

In some aspects of the invention the isotherm is controlled by adjusting the concentration of at least one modifier in the feed stream, which modifier is the pH of the feed stream.

In some aspects of the invention at least one further component is another form of the said polypeptide, such as a glycosylated form, a deamidated form, a truncated form, an extended form, a deamidated form, an incorrectly folded form or an oxidized form of said polypeptide of interest, a form with undesired glycosylation, a form resulting from racemization, a form lacking amino acids in the intra-peptide chain, a form having extra amino acids in the intra-peptide chain and a form wherein an acylation has taken place on another residue than desired.

Symbols

| | | |
|---|---|---|
| A | [—] | Initial slope of the isotherm |
| c | [M] or [g/l] | Concentration in liquid phase (without index total molar concentration) |
| $K_{eq}$ | | Equilibrium constant |
| $K_D$ | [—] | Steric exclusion factor |
| m | [—] | Ratio between fluid flow and solid flow |
| q | [M] or [g/l] | Dimensionless concentration of bound protein |
| Q | [m³/s] | Volumetric flow |
| V | [m³] | Volume |
| $\tilde{V}$ | [—] | Dimensionless volume $\tilde{V} = V/V_{col}$ |
| z | [—] | Charge number |

Greek Letters:

| | | |
|---|---|---|
| $\alpha_{AB}$ | [—] | Selectivity |
| $\alpha$ | [—] | Dimensionless feed flow, $\alpha = Q^F/Q^{II}$ |
| $\alpha_i$ | [—] | parameter in line fit |
| $\beta_i$ | [—] | parameter in line fit |

-continued

| | | |
|---|---|---|
| $\epsilon$ | [—] | Interstitial porosity |
| $\epsilon_p$ | [—] | Particle porosity |
| $\alpha_t$ | [—] | Column total porosity, $\epsilon_t = \epsilon + (1 - \epsilon) \cdot \epsilon_p$ |
| $\gamma$ | [—] | Activity coefficient |
| $\Lambda$ | [—] | Dimensionless ligand density |

Symbols in Subscript:

| | |
|---|---|
| Dead | Dead volume |
| i | Component number |
| | Inlet |
| init | Initial |
| m | Modifier |
| NR | Non Retained |
| p, pore | Pore phase |
| R | Retention |

Symbols in Superscript:

| | |
|---|---|
| max | Maximum |
| F | Feed |
| I, II, III | Refers to a section in the plant, i.e. section I, section II, section III |

The Following is a List of Aspects Further Describing the Invention:

1. A method for the chromatographic separation of a polypeptide of interest from at least one further component in a fluid mixture, the method comprising
a) Providing a counter current purification system that comprises a plurality of sections in fluid connection, said sections comprising at least one solid phase and a first desorbent stream;
b) introducing said fluid mixture as the feed stream into said counter current purification system wherein the fluid mixture contacts the solid phase in a counter current mode;
c) controlling the isotherm by adjusting the concentration of at least one modifier in the feed stream so that the initial slope of the isotherm is about parallel with the slope of the operating line when a plot is made of $m^{III}$ & A as a function of $Q^F$ or $\alpha$;
d) effecting separation of the polypeptide of interest from at least one further component; and
e) collecting the polypeptide of interest to provide a purified composition thereof.

2. The method according to aspect 1, wherein said concentration of at least one modifier in the feed stream is controlled to be different from the concentration of the same modifier in the section prior to the feed stream such as the desorbent stream.

3. The method according to any one of aspects 1 or 2, wherein the polypeptide of interest is glucagon-like peptide or a GLP-1 agonist.

4. The method according to aspect 3, wherein the polypeptide of interest is GLP-1 (1-37) or an analogue or derivative thereof.

5. The method according to aspect 4, wherein the GLP-1 (1-37) or an analogue or derivative thereof is recombinantly derived.

6. The method according to any one of aspects 1-5, wherein the counter current purification system is an Ion Exchange Chromatography system.

7. The method according to aspect 6, wherein the Ion Exchange Chromatography system is an anion exchange system.

8. The method according to aspect 6, wherein the Ion Exchange Chromatography system is a cation exchange system.

9. The method according to any one of aspects 1-8, wherein the isotherm is controlled by control of the salt concentration in the feed stream, $c_s$.

10. The method according to any one of aspects 1-9, wherein the salt concentration in the feed stream relative to the salt concentration in the stream in the section prior to the feed stream is in the range:

$$\frac{v_B - \alpha_{AB}^{III}}{v_B + 1/2 \cdot \alpha_{AB}^{III}} \leq \frac{c_s^F}{c_s^{II}} \leq \frac{v_A - 1/\alpha_{AB}^{III}}{v_A}$$

where the selectivity is given as $$\alpha_{AB} = \frac{A_A}{A_B} = \exp(\beta_A - \beta_B) \cdot c_s^{(\alpha_A - \alpha_B)},$$

and where the parameters $\alpha_i$ and $\beta_i$ for components A and B are fitted to the retention volumes in a double logarithmic plot of:

$$\ln(\tilde{V}_R - \tilde{V}_{NR}) = \alpha_i \cdot \ln(c_s) + \beta_i$$

11. The method according to any one of aspects 1-10, wherein the salt concentration in the feed stream relative to the salt concentration in the stream in the section prior to the feed stream is in the range:

$$0.39 \leq \frac{c_s^F}{c_s^{II}} \leq 0.80.$$

12. The method according to any one of aspects 1-10, wherein the salt concentration in the feed stream, $c_s^F$, is in the range from about 17.5 mmol/kg to about 36 mmol/kg and the chloride concentration in the stream in the section prior to the feed stream is about 45 mmol/kg.

13. The method according to any one of aspects 1-10, wherein the salt concentration in the feed stream, $c_s^F$, is in the range from about 28 mmol/kg to about 33 mmol/kg and the chloride concentration in the stream in the section prior to the feed stream is about 45 mmol/kg.

14. The method according to any one of aspects 1-10, wherein the salt concentration in the feed stream, $c_s^F$, is in the range from about 87 mmol/kg to about 114 mmol/kg and the chloride concentration in the stream in the section prior to the feed stream is about 130 mmol/kg.

15. The method according to any one of aspects 1-10, wherein the salt concentration in the feed stream, $c_s^F$, is in the range from about 99 mmol/kg to about 114 mmol/kg and the chloride concentration in the stream in the section prior to the feed stream is about 130 mmol/kg.

16. The method according to any one of aspects 1-15, wherein the desorbent comprises a salt which is selected from any organic or inorganic salt and mixtures thereof, such as NaCl, KCl, NH$_4$Cl, CaCl$_2$, sodium acetate, potassium acetate, ammonium acetate, sodium citrate, potassium citrate, ammonium citrate, sodium sulphate, potassium sulphate, ammonium sulphate, calcium acetate or mixtures thereof.

17. The method according to any one of aspects 1-5, wherein the counter current purification system is a Reverse Phase Chromatography (RPC) system.

18. The method according to any one of aspects 1-5, wherein the counter current purification system is a Hydrophobic Interaction Chromatography (HIC) system.

19. The method according to aspects 16, wherein the desorbent comprises an inorganic salt, such as ammonium sulphate.

20. The method according to aspect 17, wherein the isotherm is controlled by control of the concentration of the organic modifier in the feed stream.

21. The method according to aspect 17, wherein the desorbent comprises an organic solvent, such as an organic solvent selected from ethanol, methanol, propanol, and acetonitrile.

22. The method according to any one of aspects 1-5 or 17-21, wherein the difference between the modifier in the feed stream and the stream in the section prior to the feed stream is in the range:

$$\frac{1+1/2}{K_{m,B}} \cdot \alpha_{AB}^{III} \leq c_m^F - c_m^{II} \leq \frac{1}{K_{m,A} \cdot \alpha_{AB}^{III}}$$

where the selectivity is given by:

$$\alpha_{AB} = \frac{A_A}{A_B} = \frac{\exp(\alpha_A \cdot c_m + \beta_A)}{\exp(\alpha_B \cdot c_m + \beta_B)} = \exp((\alpha_A - \alpha_B) \cdot c_m + (\beta_A - \beta_B))$$

and the parameters $\alpha_i$ and $\beta_i$ for component A and B are fitted to the retention volumes in a semi logarithmic plot to the function:

$$\ln(\tilde{V}_R - \tilde{V}_{NR}) = \alpha_i \cdot c_m + \beta_i$$

22. The method according to any one of aspects 1-5 or 17-22, wherein the difference between the modifier in the feed stream and the stream in the section prior to the feed stream, $c_m^F - c_m^{II}$, is $-3.5$ wt % $\leq c_m^F - c_m^{II} \leq -1.4$ wt %.

23. The method according to any one of aspects 1-5 or 17-22, wherein the modifier in the feed stream is present in the range from about 27.3 wt % to about 29.4 wt %, and the ethanol in the stream in the section prior to the feed stream is present in about 30.8 wt %.

24. The method according to any one of aspects 1-5 or 17-22, wherein the modifier in the feed stream is present in the range from about 53.7 wt % to about 57.1 wt % and the ethanol in the stream in the section prior to the feed stream is present in about 58.4 wt %.

23. The method according to any one of aspects 1-5, wherein the counter current purification system is using adsorption chromatography, partition chromatography, size exclusion chromatography, or affinity chromatography.

24. The method according to any one of aspects 1-23, wherein the counter current purification system is a Simulated moving bed (SMB) purification system.

25. The method according to any one of aspects 1-23, wherein the counter current purification system is a Multi-column Counter Current Solvent Gradient Purification (MC-SGP) system.

26. The method according to any one of aspects 1-25, wherein the separation occurs under linear adsorption isotherms.

27. The method according to any one of aspects 1-26, wherein the feed stream composition remains constant throughout the procedure.
28. The method according to any one of aspects 1-26, wherein the feed stream composition is changed during the procedure.
29. The method according to any one of aspects 1-28, wherein the control of the isotherm by adjustment of the concentration of at least one modifier in the feed stream leads to a process with a gradient.
30. The method according to any one of aspects 1-29, wherein the control of the isotherm by adjustment of the concentration of at least one modifier in the feed stream leads to an operating point that lies between the isotherms for said polypeptide of interest and said at least one further component.
31. The method according to any one of aspects 1-30, wherein the isotherm is controlled by adjusting the concentration of at least one modifier in the feed stream, which modifier is the pH of the feed stream.
32. The method according to any one of aspects 1-30, wherein said at least one further component is another form of the said polypeptide, such as glycosylated, deamidated, or oxidized form of said polypeptide.
33. The method according to any one of aspects 1-32, wherein the relation between the polypeptide of interest and the said at least one further component is at least 4:1.
34. The method according to any one of aspects 1-32, wherein the relation between the polypeptide of interest and the said at least one further component is at least 10:1.
35. The method according to any one of aspects 1-32, wherein the relation between the polypeptide of interest and the said at least one further component is at least 20:1.
36. The method according to any one of aspects 1-32, wherein the relation between the polypeptide of interest and the said at least one further component is at least 50:1.
37. The method according to any one of aspects 1-32, wherein the relation between the polypeptide of interest and the said at least one further component is at least 80:1.

REFERENCES

Abel S., Marco Mazzotti, M. Morbidelli, "Solvent gradient operation of simulated moving beds, I Linear isotherms", J. Chrom. A, 944 (2002) 23-39

Abel S., M. U. Bäbler, C. Arpagaus, M Mazzotti, J. Stadler, "Two-fraction and three fraction continuous simulated moving bed separation of nucleosides", J. Chrom. A, 1043 (2004) 201-210

Antos C., A. Seidel-Morgenstern, "Application of gradient in the simulated moving bed process", 56 (2001) 6667-6682

Brooks C. A., S. M. Cramer, "Steric Mass-Action Ion Exchange: Displacement Profiles and Induced Salt Gradients", AIChE J. 38 (1992) 1969-1978

Guiochon G. et. al., "Fundementals of Preparative and Nonlinear Chromatography, Second Edition", Elsevier (2006)

Jeansonne Mark S., Joe P. Foley, "Review of the Exponentially Modified Gaussian (EMG) Function since 1983", Journal of Chromatographic Science, 29 (1991), pp. 258-266

Jensen T. B. et. al., "Novel Simulated Moving-Bed Method for Reduced Solvent Consumption", J. Chrom. A. 873 (2000) pp. 149-162

Kessler L. C., L. Bueorguieva, U. Rinas, A. Seidel-Morgernstern, "Step gradients in 3-zone simulated moving bed chromatography, Application to purification of antibodies and bone morphogenetic protein-2", J. Chrom. A, 1176 (2007), 69

Ma Z., N.-H.-L. Wang, "Standing Wave Analysis of SMB Chromatography: Linear Systems", AIChE Journal 43 (1997) pp. 2488-2508.

Mollerup, J. M., "Applied thermodynamics: A new frontier for biotechnology", Fluid Phase Equilibria 241 (2006) 205-215

Mollerup J. M. et. al., "Quality by design—Thermodynamic modelling of chromatographic separation of proteins", J. Chrom. A. 1177 (2008) pp. 200-208

Pedersen Linda, et. al., "Whey proteins as a model system for chromatographic separation of proteins", J. Chrom. B. 790 (2003) pp. 161-173

Ruthven D. M., C. B. Ching, "Counter-current and Simulated Counter-Current Adsorption", Chem. Eng. Sci. 44 (1989), pp. 1011-1038

Schulte M., L. Britsch, J. Strube, "Continuous Preparative Liquid Chromatography in the Downstream Processing of Biotechnological", Acta Biotechnology 20 (2000) pp. 3-15

Storti G., M. Masi, S. Carra, M. Morbidelli, "Optimal Design of Multicomponent Counter Current Adsorption Separation Processes Involving Nonlinear Equilibria", Chem. Eng. Sci, 44, (1989) pp. 1329-1345

Storti G., M. Mazzotti, M. Morbidelli, S. Carrà, "Robust Design of Binary Counter Current Adsorption Separation Processes", AIChE Journal, 39 (1993) 471-492

Wang Linda N-H. et. al., EP 1 349 866 B1 "Insulin Purification Using Simulated Moving Bed Technology"

Wekenborg K. et. al., "Nicht-isokratische TMS-Trennung von Proteinen mittels Ionenaustauschchromatographie", Chemie Ingenieur Technik 76 (2006) pp. 815-819

Hansen T., S. Kidal, "Simulation of an Industrial Ion Exchange Step (Part 1): Determination of the most Relevant Parameters", Poster at PREP Conference (2007)

EXAMPLES

Example 1 is related to purification of the GLP-1 analogue, Liraglutide, using ion exchange chromatography. Example 2 is purification of the insulin analogue, desB30 human insulin, using reversed phase HPLC chromatography. Examples 3 and 4 are further examples related to the selection of modifier concentrations in respectively ion exchange and RP HPLC chromatography.

Example 1

Experimental Work to Determine Equilibrium Parameters for SMB Experiments I-III

The separation with a salt gradient was demonstrated by ion exchange chromatography. As model system was selected the separation of the GLP-1 analogue Liraglutide (strongly bound component) and a number of impurities, where the critical impurity was very similar to GLP-1 and eluting just before the product.

Determination of A

The initial slope of the isotherm was determined from isocratic pulse experiments. A description of pulse experiments can be found in Pedersen (2003).

Chromatographic Column

The chromatographic media used was Source 30Q from GE Healthcare. The column had a length of 3.5 cm and an inner diameter of 2.5 cm.

Solvents

Two solvents with different solvent strengths were mixed. The buffers contained 63 wt % of ethanol. The solvents were buffered with 0.24 wt % Tris (CAS no. 77-86-1) and the pH was adjusted to pH=7.6 with 1 M HCl (CAS no. 7647-01-0).

The weaker desorbent contained 0.37 wt % NaCl (CAS no. 7647-14-5) whereas no salt was added to the stronger solvent, and the pH was adjusted to 7.6.

Liraglutide and its impurities were present in liquid form from a previous process step. The fluid mixture was mixed 1:1 with water to lower the ethanol concentration. Afterwards, the solution was captured on a RP column and eluted with the solvent without salt described above.

Determination of $V_{NR}$

The injected sample conductivity was slightly lower than the conductivity of the eluent. At the outlet of the Äkta-system a decrease in conductivity could be measured. The retention volume for this decrease corresponded to the retention volume of a non-retained component. The retention volume from the non-retained component, $V_{NR}$, was measured to 16.5 ml.

Alternatively the retention volume can be measured by saturating the column with nitrate and injecting a small amounts of water (Pedersen 2003).

Isocratic Experiments

The gradient mixer in the Äkta-system was used to obtain the desired salt concentration for the isocratic experiments.

The isocratic experiments were made starting with the highest salt concentration, leading to the lowest retention volume. The salt concentration was gradually reduced in each experiment.

In the isocratic experiments the column was equilibrated with app. 2 column volumes. Hereafter the UV-detector was reset and a fluid mixture containing the product and the impurity was injected. The column elution continued until the peak was eluted from the column and a steady baseline UV-signal was reached.

A detailed description of pulse experiments can be found in Pedersen (2003).

Parameters to determine the maximum binding capacity has previously been published for this GLP-1 analogue, Hansen & Kidal (2007). Handling the non-linear part of the isotherm can be found in Mollerup (2008).

Evaluation of the Experiment

The retention volumes from the peaks were all taken from the peak maximum. Another approach would be to fit the peak to either a Gaussian function or to an emg-function (Jeansonne 1991), depending on the skewness of the peaks.

The retention volume was determined from the $1^{st}$ normal moment of the peak.

These pulse experiments were done with a mixture of the product peak and the impurity eluting closest to the product peak before the main peak.

The data were plotted in a double logarithmic plot as described above, FIG. 6.

Results from Pulse Experiments

In table 1 below is given the retention volumes measured (measured as the peak maximum) for the weaker bound impurity (peak B) and the product Liraglutide peak (peak A).

TABLE 1

| Experiment no | % weak desorbent [%] | $C_{Cl}$ [mmol/kg] | $V_{peak,A}$ [ml] | $V_{peak,B}$ [ml] |
|---|---|---|---|---|
| 1 | 65 | 51.24 | 39.4 | 32.5 |
| 2 | 40 | 37.10 | 83.4 | 59.5 |
| 3 | 50 | 42.76 | 58.5 | 43.9 |
| 4 | 45 | 39.93 | 69 | 50.6 |
| 5 | 60 | 48.41 | 43.8 | 35.3 |
| 6 | 55 | 45.58 | 50.3 | 39.1 |

Source 30Q was used as anion exchange chromatography system and the anion used throughout the experiments was chloride (with both chloride from the salt and the titration included). The data were plotted in a double logarithmic plot, see FIG. 6.

A line fit of the two data series gave $$\ln\left(\frac{V_{peak,i} - V_{NR}}{V_{col}}\right) = \alpha_i \cdot \ln(c_{Cl^-}) + \beta_i$$

The parameters found for the two peaks are listed in table 2.

TABLE 2

| Component | Stronger bound impurity (A) | Weaker bound impurity (B) |
|---|---|---|
| α | −3.34 | −3.07 |
| β | 13.43 | 12.00 |

In order to be able to separate the two components, the relative flow between the liquid and solid phase, m, was set between the initial slope of the isotherms of the two components.

The retention volume of a non-retained component, $V_{NR}$, was measured to 16.5 ml, app. 3 ml of this volume was the dead volume from the Äkta. The remaining 13.5 ml was from the porosity of the column. Setting the interstitial porosity to 0.38 the particle porosity was determined:

$$\varepsilon_p = \frac{\frac{V_{NR} - V_{dead}}{V_{col}} - \varepsilon}{1 - \varepsilon} = \frac{\frac{16.5 - 3}{16.7} - 0.38}{1 - 0.38} = 0.69$$

Liraglutide is a small molecule and was considered to be able to enter into all the pores, $K_D$ was hence set to 1.

Calculation of Operating Point

The calculation for the salt concentrations corresponds to the SMB experiment II described below.

Determination of Salt Concentration

Eight columns were packed for the SMB-plant slightly shorter than the column used for the pulse experiments, namely 3.4 cm, corresponding to a column volume of 16.7 ml.

The salt concentration in the desorbent I stream was approximately 44 mmol/kg and the salt concentration in the desorbent II stream was approximately 52 mmol/kg. Since the retention volume is a strong function of the salt concentration, two pulse experiments were made to determine the exact salt concentration.

Before the two solvents were used in the SMB-plant, the retention volume was measured from pulse experiments. The resulting chromatograms are plotted in FIG. 15. The peaks were fitted to the EMG-function, and the first normal moment of the two peaks was calculated to be 48.8 ml and 36.7 ml, respectively. For the desorbent II stream this was determined to give $$\ln\left(\frac{48.8\text{ ml} - 16.5\text{ ml}}{16.7\text{ ml}}\right) = -3.34 \cdot \ln(c_s^{II}) + 13.43 = 0.660$$

and corresponded to a salt concentration of 45.8 mmol/kg.

The retention volume of 36.7 ml determined using desorbent I stream was correspondingly calculated to be 52.7 mmol/kg.

Retention Volumes in the SMB-Plant

From the parameters of the stronger adsorbed component it was seen that with a 45.8 mmol/kg chloride concentration in the desorbent II stream the retention volume in the SMB-plant was $$\ln\left(\frac{V_R^A - (13.5\text{ ml} + 0.3\text{ ml})}{16.7\text{ ml}}\right) = -3.34 \cdot \ln(45.8\text{ mM}) + 13.43 = 0.657$$

To find the A corresponding to a retention volume of $V_R = 46$ ml insertion was made in $$V_R = 46\text{ ml} = V_{col} \cdot (\epsilon + (1-\epsilon) \cdot \epsilon_p \cdot K_D \cdot (1+A)) = 16.7\text{ ml} \cdot (0.38 + (1-0.38) \cdot 0.69 \cdot 1 \cdot (1+A))$$

leading to an A of the stronger bound component in section II of 4.50.

Correspondingly, the retention volume of the weaker bound component was $$\ln\left(\frac{V_R^B - (13.5\text{ ml} + 0.3\text{ ml})}{16.7}\right) = -3.07 \cdot \ln(45.8\text{ mM}) + 12.00 = 0.266$$

which gave a retention volume in section II of 35.5 ml, which corresponded to an A of 3.04.

With the retention volumes in section II of 35.5 ml and 46 ml the operating point at a low feed flow would be a flow corresponding to a retention volume between these two points. As operating point was selected 19 ml/min with a shifting time of 2 min, which corresponds to a volumetric flow of 38 ml.

Calculation of Optimal Salt Concentration in the Feed Stream

To obtain the same slope of the binding and the initial slope of the isotherm, first the pore phase flow was calculated. This was $$Q_{pore} = \frac{V_{col} \cdot (1-\epsilon)}{t_{sft}} = \frac{16.7\text{ ml} \cdot (1-0.38) \cdot 0.69}{2\text{ min}} = 3.58\text{ ml/min}$$

To obtain the same slope of e.g. the weaker bound component, the salt concentration in the feed stream was calculated:

$$c_s^F = \frac{v_i \cdot A_i^{III} \cdot \frac{Q_{Net}^{II}}{Q_{Net}^{II} + Q^F} - \frac{Q_{Net}^{II}}{Q_{pore}}}{v_i \cdot A_i^{III} \cdot \frac{Q_{Net}^{II}}{Q_{Net}^{II} + Q^F} + \frac{Q^F}{Q_{pore}}} \cdot c_s^{II}$$

$$= \frac{3.07 \cdot 3.04 \cdot \frac{12.1}{12.1+0} - \frac{12.1}{3.58}}{3.07 \cdot 3.04 \cdot \frac{12.1}{12.1+0} + \frac{2}{3.58}} \cdot 45.8\text{ mmol/kg}$$

$$= 27.6\text{ mmol/kg}$$

since $$Q_{Net}^{II} = Q_{SMB}^{II} - V_{NR}/t_{sft}$$
$$= 19\text{ ml/min} - (13.5 + 0.3)\text{ml/min}$$
$$= 12.1\text{ ml/min}$$

at a feed flow $Q_F = 0$.

For a higher feed flow, an iterative procedure (e.g. successive substitution) was required for calculation since $A_i^{II}$ depends on the salt concentration from the mixing of the feed and section II flow.

Knowing the salt concentration in the feed stream and in section II the salt concentration in section III was calculated from the mixing of the two streams.

From the salt concentration the resulting A for the two components was calculated and plotted as a function of the feed flow, FIG. 16. Furthermore the dimensionless flow in section III was calculated.

The actual salt concentration in the experiment was lower, namely 14.6 mmol/kg, leading to a lower slope of the operating line compared to the change in the binding capacity, FIG. 17.

SMB Experiment I

Equipment

The experiments were run on a lab-scale SMB-plant. The experiments in the SMB-plant were performed on a KNAUER SMB system CSEP C9116 equipped with 8 columns each with a volume of 17.2 ml. The setup of the SMB-plant was with an equilibration and regeneration section, to make the process continuous (Abel 2004).

Each of the three sections performing the separation consisted of two columns as shown in FIG. 5.

Solvents

The desorbent stream was identical to the desorbent stream described above except that the chloride concentration was 44 mmol/kg. This stream was also used for the equilibration of the columns.

The feed stream contained 5.5 g/l Liraglutide and the concentration of the weaker bound component was approximately 1% of the concentration of Liraglutide. The salt concentration in the feed stream was 14 mmol/kg, as described above.

The regeneration stream contained 11.7 wt % NaCl and 0.3 wt % HAc.

Operating Conditions

The experiment was made with a 3 min shifting time. The flows in the regeneration and equilibration zones were set to 10 ml/min. The desorbent flow was set to 20 ml/min, the zone II flow was 15 ml/min, and the feed flow was 1.5 ml/min.

Results

Analysis of samples taken from the raffinate port showed that the content of the weaker bound component was in the range 0.7 to 8% of the total polypeptide concentration.

SMB Experiment II

Equipment

A second experiment was made without a connection between section I and section II to allow different salt concentrations in these two sections, FIG. 18.

The experiment was run on a lab-scale SMB-plant. The experiment in the SMB-plant was performed on a KNAUER SMB system CSEP C9116 equipped with 8 columns each with a volume of 16.7 ml. The setup of the SMB-plant was with an equilibration and regeneration section, to make the process continuous (Abel 2004).

Each of the three sections performing the separation consisted of two columns as shown in FIG. 18. Both the extract and the raffinate streams were equipped with UV-detectors to monitor the process.

Solvents

The composition of the equilibration solvent was identical to the solvent in section II.

The solvent for regeneration of the columns was a 11.7 wt % NaCl, 0.3 wt % HAc solution.

The desorbent I and II streams were as described above.

The composition of desorbent I & II were as described above and the salt concentration as calculated in details above in "Determination of Salt Concentration".

The feed stream contained 4.3 g/L Liraglutide and the impurity to be removed was approximately 1% of the Liraglutide concentration. The salt concentration was 14.6 mmol/kg.

Operating Conditions

The experiment was made with a 2 min shifting time. The flow in regeneration, equilibration, and section I were all set to 20 ml/min. The flow in section II was set to 19 ml/min. The feed flow was set to ½ ml/min and increased in steps of ½ ml/min approximately every hour of up to 2½ ml/min, FIG. 17.

Results

The UV-signal from the extract stream was plotted in FIG. 19. From the figure it is seen how the UV-signal increased to a higher level everytime the feed flow was increased. The UV-signal for the raffinate port is given in FIG. 20. In the figure it is seen that the UV-signal increased to a plateau around 20-25 mAU whereafter it started to increase again after approximately 1.8 min.

The concentration of the weakly bound key component in the raffinate stream was in the range 0.8 to 1.3% of the total polypeptide concentration, indicating that the component was not efficiently washed out of the plant.

SMB Experiment III

The experiment was made on a KNAUER SMB system CSEP C9116 with a lay-out similar to FIG. 5. The plant was equipped with 8 columns with an average length of 2.6 cm and internal diameter of 2.5 cm.

The non-retained volume of the columns were measured by $KNO_3$ as described by Pedersen (2003), and determined to 10.8 ml.

Solvents

The solvent used for the regeneration stream was identical to the solvent used for the regeneration stream described above, and the desorbent stream was identical to the stream used for pulse experiments except that the chloride concentration was 45 mmol/kg. The same stream was used for desorbent and regeneration.

The feed stream was collected from the main peak as described above in "Experimental Work to Determine Equilibrium Parameters for SMB Experiments I-III" and the chloride concentration in the feed stream was adjusted to 30 mmol/kg by adding NaCl. The concentration of Liraglutide was 4.7 g/l and the weakly bound impurity had a concentration of about 2% of the Liraglutide concentration.

Operating Conditions

The shifting time was set to 3 min. The flow in the regeneration and equilibration section was set to 4 ml/min. The flow in zone I was 16 ml/min, the flow in zone II was 9.5 ml/min and the feed flow was tested at 0.5 and 2 ml/min.

Salt Concentration

The salt concentration for a feed stream flow of 0 is an explicit function, since $A_i^{III} = A_i^{II}$.

Thus the dimensionless flow in section II was $$Q_{Net}^{II} = Q_{SMB}^{II} - V_{SMB}^{NR}/t_{sft} = 9.5 \text{ ml/min} - (10.8+0.3) \text{ ml/3 min} = 5.8 \text{ ml/min}$$

Using $\epsilon = 0.38$, and $\epsilon_p = 0.75$, $Q_{pore}$ became $$Q_{pore} = V_{col} \cdot (1-\epsilon) \cdot \epsilon_p / t_{sft} = 12.8 \text{ ml} \cdot (1-0.38) 0.75/3 \text{ min} = 1.983 \text{ ml/min}$$

and hence $m^{II}$ was $$m^{II} = \frac{5.8 \text{ ml/min}}{1.983 \text{ ml/min}} = 2.92$$

The initial slope of the weakly bound component was $$A_B = \frac{V_R(45 \text{ mmol/kg}) - V_{NR}}{V_{col} \cdot (1-\varepsilon) \cdot \varepsilon_p}$$

$$= \frac{\exp(\alpha \cdot \ln(C_{Cl^-}) + \beta)}{(1-\varepsilon) \cdot \varepsilon_p}$$

$$= \frac{\exp(-3.07 \cdot \ln(45 \text{ mmol/kg}) + 12.00)}{(1-0.38) \cdot 0.75}$$

$$= 2.95$$

The required chloride concentration in the feed concentration to wash out the weakly bound impurity for a linear isotherm was $$c_s^F = \frac{v_i \cdot A_i^{III} - (1+\alpha) \cdot m^{II}}{v_i \cdot A_i^{III} + (1+\alpha) \cdot \alpha \cdot m^{II}} \cdot c_s^{II}$$

$$= \frac{3.07 \cdot 2.95 - (1+0) \cdot 2.92}{3.07 \cdot 2.95 + (1+0) \cdot 0 \cdot 2.92} \cdot 45 \text{ mmol/kg}$$

$$= 30.5 \text{ mmol/kg}$$

and correspondingly the chloride concentration calculated from the stronger bound component was 36.0 mmol/kg.

With a feed stream flow higher than 0 ml/min., $A^{III}$ was a function of the feed stream chloride concentration and an iterative procedure was required. With a feed flow of 2 ml/min the resulting feed stream chloride concentration was between 27.7 and 33.1 mmol/kg. Based on this the chloride concentration in the feed stream was set to 30 mmol/kg.

The selectivity in section II was calculated:

$$\alpha_{AB}^{II} = \frac{A_A}{A_B} = \frac{\exp(-3.34 \cdot \ln(45 \text{ mmol/kg}) + 13.43)}{\exp(-3.07 \cdot \ln(45 \text{ mmol/kg}) + 12.00)} = 1.50$$

With a 2 ml/min feed flow the chloride concentration in section III was $$c_{Cl^-}^{III} = \frac{45 \text{ mmol/kg} + 2\frac{\text{ml}}{\text{min}} \bigg/ 5.8\frac{\text{ml}}{\text{min}} \cdot 30 \text{ mmol/kg}}{1 + 2\frac{\text{ml}}{\text{min}} \bigg/ 5.8\frac{\text{ml}}{\text{min}}}$$

$$= 41.1 \text{ mmol/kg}$$

and at this chloride concentration the selectivity in section III was $$\alpha_{AB}^{III} = \frac{A_A}{A_B} = \frac{\exp(-3.34 \cdot \ln(41.1 \text{ mmol/kg}) + 13.43)}{\exp(-3.07 \cdot \ln(41.1 \text{ mmol/kg}) + 12.00)} = 1.53$$

It is seen that within the given operating range the selectivity only changed about 2%.

A reasonable interval for the chloride concentration was derived earlier to $$\frac{v_B - \alpha_{AB}^{III}}{v_B + 1/2 \cdot \alpha_{AB}^{III}} \leq \frac{c_s^F}{c_s^{II}} \leq \frac{v_A - 1/\alpha_{AB}^{III}}{v_A}$$

Insertion of the parameters from the fit to the isocratic pulse experiments in table 2 above gave $$\frac{3.07 - 1.53}{3.07 + 1/2 \cdot 1.53} \leq \frac{c_s^F}{c_s^{II}} \leq \frac{3.34 - 1/1.53}{3.34}$$

$$\frac{3.07 - 1.53}{3.07 + 1/2 \cdot 1.53} \leq \frac{c_s^F}{c_s^{II}} \leq \frac{3.34 - 1/1.53}{3.34}$$

i.e.

$$0.39 \leq \frac{c_s^F}{c_s^{II}} \leq 0.80$$

And with 45 mmol/kg chloride in section II, the feed stream interval was 17.5 mmol/kg $\leq c_s^F \leq$ 36 mmol/kg Results In FIG. 22 is shown the UV-signal for the raffinate port from experiment III. A large difference is seen between the raffinate UV-signal from experiments II and III. In experiment III a clear drop in UV-signal is seen from 1.5-2 min, which is not seen in experiment II.

Samples from both experiments were analysed to determine the content of the weakly bound impurity. In experiment II the concentration of the weakly bound impurity in the feed stream was approximately 1% in both the feed stream and the raffinate stream.

In experiment III the concentration of the weakly bound impurity in the feed stream was approximately 2% of the total polypeptide concentration whereas in the raffinate stream it was in the range from about 25 to about 50% (at $Q^F=2$ and ½ ml/min), showing an efficient elution of the weakly bound impurity in zone III at both operating points.

A more efficient elution of the weakly bound impurity is hence seen by increasing the salt concentration in the feed stream.

Example 2

SMB Experiment IV

Equipment

The equilibrium determinations were performed on an Äkta system equipped with a 17.2 ml column.

The experiments were run on a lab-scale SMB-plant. The experiments in the SMB-plant were performed on a KNAUER SMB system CSEP C9116 equipped with 8 columns with an average volume of 15.7 ml. The setup of the SMB-plant was with an equilibration and regeneration section, to make the process continuous (Abel 2004).

Each of the three sections performing the separation consisted of two columns as shown in FIG. 5. Both the extract and the raffinate stream were equipped with UV-detectors to monitor the process.

Chromatographic Column

The columns were packed with reversed phase silica particles with a diameter of 15 µm and a pore diameter of 200 Å and ODDMS manufactured by FeF Chemicals A/S. All columns had a diameter of 2.5 cm.

Solvents

The dead volumes were determined using a 1 wt % $KNO_3$ in water as described by Pedersen (2003)

The composition of the equilibration solvent was identical to the desorbent and consisted of 30.75 wt % ethanol, 1.5 wt % KCl, and 0.18 wt % TRIS, the remaining being water. The pH was adjusted to 8, using 1M HCl.

The composition for the solvents to determine the equilibrium parameters had the same salt concentrations as the solvent above but contained 25 and 31 wt % ethanol, respectively.

The solvent for regeneration was a 70 wt % ethanol solution containing NaCl and 2.1 wt % citric acid.

The feed stream contained 29 wt % ethanol, 0.18 wt % TRIS and approximately 10 g/l insulin precursor desB30 human insulin. Additionally the feed stream contained 0.15 g/l (or 1.5% of the desB30 human insulin concentration) of the weaker bound key component. The key component is the component eluting closest to the product component. Additional weakly bound components were present in the feed stream, too.

Results from Pulse Experiments

In table 3 below is given the measured retention volumes (measured as the peak maximum) for the weaker bound impurity (peak B) and the product, which is desB30 human insulin (peak A). All measurements were made on a column with L=3.5 cm and $d_{col}$=2.5 cm. $V_{NA}$ for the column was determined to 11.9 ml.

TABLE 3

| Experiment no | % weak desorbent [%] | $C_{EtOH}$ [wt %] | $V_{peak,A}$ [ml] | $V_{peak,B}$ [ml] |
|---|---|---|---|---|
| 7 | 100 | 31 | 47 | 38.4 |
| 8 | 90 | 30.4 | 58.7 | 47.9 |
| 9 | 80 | 29.8 | 75.3 | 60.4 |
| 10 | 70 | 29.2 | 100.8 | 80.7 |

TABLE 3-continued

| Experiment no | % weak desorbent [%] | $C_{EtOH}$ [wt %] | $V_{peak,A}$ [ml] | $V_{peak,B}$ [ml] |
|---|---|---|---|---|
| 11 | 65 | 28.9 | 117.3 | 93.6 |
| 12 | 60 | 28.6 | 138.7 | 111.5 |

A line fit of the two data series gave $$\ln\left(\frac{V_{peak,i} - V_{NR}}{V_{col}}\right) = \alpha_i \cdot c_{EtOH} + \beta_i$$

The parameters found for the two peaks are listed in table 4.

TABLE 4

| Component | Strong (A) | Weak (B) |
|---|---|---|
| α [wt %$^{-1}$] | −0.551 | −0.570 |
| β | 17.72 | 18.00 |

The measured data points together with the line fit is given in FIG. 23.

The slope α is identical to the parameter $K_m$ as described in the description in the part: "Reversed Phase Chromatography (RPC or RP) & Hydrophobic Interaction Chromatography (HIC)"

The selectivity calculated from the values in table 4 at 30 wt % ethanol became:

$$\alpha_{AB} = \exp((\alpha_A - \alpha_B) \cdot c_m + (\beta_A - \beta_B))$$
$$= \exp((-0.551 + 0.570) \cdot 30 + (17.72 - 18.00))$$
$$= 1.33$$

$$\frac{1\frac{1}{2}}{K_{m,B}} \cdot \alpha_{AB}^{III} \leq c_m^F - c_m^{II} \leq \frac{1}{K_{m,A} \cdot \alpha_{AB}^{III}}$$

and insertion of the parameters in the expression gave $$\frac{1\frac{1}{2}}{-0.570} \cdot 1.33 \leq c_m^F - c_m^{II} \leq \frac{1}{-0.551 \cdot 1.33}$$
$$-3.5 \text{ wt \%} \leq c_m^F - c_m^{II} \leq -1.4 \text{ wt \%}$$

i.e. an ethanol concentration in the feed stream which is 1.4-3.5 wt % lower than the section II ethanol concentration.

Operating Conditions

The experiment was made with a 3 min shifting time. The flow in regeneration, equilibration was set to 10 ml/min. The flow in section I was 18 ml/min, the flow in section II was initially set to 13 ml/min with a feed flow of 2 ml/min.

After 1 hour of operation, the section II flow was reduced to 12 ml/min and the feed flow was increased to 3 ml/min.

Ethanol Concentration

The non-retained volume of the column was determined to 11.9 ml. Setting ε=0.38 the particle porosity became $\epsilon_p$=0.61 with a 3 min shifting time $Q_{pore}$=1.98 ml/min. The flow in section II was 13 ml/min and the net liquid and dimensionless flows became:

$$Q_{Net}^{II} = Q_{SMB}^{II} - V_{NR}/t_{sft}$$
$$= 13 \text{ ml/min} - (11.9 \text{ ml} + 0.3 \text{ ml})/3 \text{ min}$$
$$= 8.93 \text{ ml/min}$$

$$m^{II} = \frac{8.93 \text{ ml/min}}{1.98 \text{ ml/min}} = 4.51$$

$$\alpha = \frac{Q^F}{Q_{Net}^{II}} = \frac{2 \text{ ml/min}}{8.93 \text{ ml/min}} = 0.224$$

The initial slope of the two components at 30.75 wt % ethanol were calculated from the parameters given in table 4 above $$A_A = \frac{V_R - V_{NR}}{V_{col}} \cdot \frac{V_{col}}{V_{pore}}$$
$$= \exp(17.72 - 0.551 \cdot 30.75) \cdot \frac{1}{(1 - 0.38) \cdot 0.61}$$
$$= 5.77$$

$$A_B = \frac{V_R - V_{NR}}{V_{col}} \cdot \frac{V_{col}}{V_{pore}}$$
$$= \exp(18.00 - 0.570 \cdot 30.75) \cdot \frac{1}{(1 - 0.38) \cdot 0.61}$$
$$= 4.32$$

The feed ethanol concentration calculated for the stronger bound component at $Q^F$=0 ml/min gave $$c_{EtOH}^F = \frac{m^{II} \cdot (1 + \alpha)^2}{K_m \cdot A_i^{III}} + c_{EtOH}^{II}$$
$$= \frac{4.51 \cdot (1 + 0)^2}{-0.551 \text{ wt \%}^{-1} \cdot 5.77} + 30.75 \text{ wt \%}$$
$$= 29.33 \text{ wt \%}$$

and correspondingly the weaker bound component gave $C_{EtOH}^F$=28.91 wt %.

For $Q^F$=2 ml/min, $A^{III}$ is a function of the ethanol concentration in the feed stream and an iterative procedure was required. The ethanol concentration in the feed stream was calculated as 28.97 and 28.56 wt %, respectively, for the stronger and weaker bound components.

Based on this the ethanol concentration in the feed stream was set to 29 wt %. A plot showing the initial slope of the isotherm and $m^{III}$ as a function of the dimensionless feed flow, α, is given in FIG. 19. It is seen that the slope of the UV-signal is almost parallel to the initial slope of $A_B$(α=0) and to the initial slope of the stronger bound component, $A_A$ at α=0.224 as expected from the calculated feed ethanol concentration above.

Results

The measured UV-signal from the extract stream is given in FIG. 25. The data are plotted for each cycle, 8 columns with 3 min shifting time. Initially the UV-signal was increasing due to the start up of the SMB-plant.

In FIG. 26 is plotted the UV-signal from the raffinate stream for each shift. The first 0.7 min the UV-signal was 0. In this period the dead volume was eluted from the column. Hereafter the UV-signal started to increase. No clear peak was seen and the feed stream contained a number of weakly bound impurities.

Analysis of the raffinate stream showed that the stream contained 5-20% of the weakly bound key component thus indicating an efficient elution of this component.

Example 3

The following is an example of how other salt concentrations in a Counter Current Purification system comprising IEX solid phases may be determined.

For determination of $\ln(\tilde{V}_R - \tilde{V}_{NR})$ in:

$$\ln(\tilde{V}_R - \tilde{V}_{NR}) = \alpha_i \cdot c_m + \beta_i$$

the following parameters are used:

TABLE 5

| Component | Strongly Bound (A) | Weakly bound (B) |
|---|---|---|
| $\alpha_i$ | −6 | −5.8 |
| $\beta_i$ | 30 | 28.7 | and the salt concentration in the desorbent stream is set to 130 mmol/kg.

With a 10 ml column volume, $V_R$, and a non retained volume, $V_{NR}$, of 8 ml, the following porosities can be used $\epsilon$=0.38, and $\epsilon$=0.677. The initial slope of the strongly bound components will be $$\frac{\tilde{V}_R - \tilde{V}_{NR}}{(1-\varepsilon)\varepsilon_p} = \frac{\exp(-6 \cdot \ln(130) + 30)}{(1-0.38) \cdot 0.677} = 5.27$$

and correspondingly for the weakly bound component 3.80.

If the flow in section II is 9 ml/min and the columns are moved every $3^{rd}$ minute the dimensionless flow in section II will be $$m^{II} = \frac{3 \text{ min} \cdot 9 \text{ ml/min} - 8 \text{ ml}}{10 \text{ ml} \cdot (1-0.38) \cdot .677} = 4.52$$

with a feed flow of 0 the feed salt concentration will for the strongly bound component be (bearing in mind that $v_i = -\alpha_i$)

$$c_s^F = \frac{v_A \cdot A_A^{III} - (1+\alpha) \cdot m^{II}}{v_A \cdot A_A^{III} + (1+\alpha) \cdot \alpha \cdot m^{II}} \cdot c_s^{II}$$

$$= \frac{6 \cdot 5.27 - (1+0) \cdot 4.52}{6 \cdot 5.27 + (1+0) \cdot 0 \cdot 4.52} \cdot 130 \text{ mmol/kg}$$

$$= 111 \text{ mmol/kg}$$

and correspondingly for the weakly bound component $$c_s^F = \frac{v_B \cdot A_B^{III} - (1+\alpha) \cdot m^{II}}{v_B \cdot A_B^{III} + (1+\alpha) \cdot \alpha \cdot m^{II}} \cdot c_s^{II}$$

$$= \frac{5.8 \cdot 3.80 - (1+0) \cdot 4.52}{5.8 \cdot 3.80 + (1+0) \cdot 0 \cdot 4.52} \cdot 130 \text{ mmol/kg}$$

$$= 103 \text{ mmol/kg}$$

If the dimensionless feed flow $\alpha = \frac{1}{2}$, an iterative procedure is required since $A^{III}$ is a function of the salt concentration in section III, which depends on the feed salt concentration.

Using an iterative procedure the result for the strongly bound component gives $c_s^F = 104.1$ mmol/kg.

The result can easily be controlled by insertion in $$c_s^{III} = \frac{c_s^{II} + \alpha \cdot c_s^F}{1+\alpha}$$

$$= \frac{130 \text{ mmol/kg} + 1/2 \cdot 104.1 \text{ mmol/kg}}{1+1/2}$$

$$= 121.4 \text{ mmol/kg}$$

$$A_A^{III} = \frac{\tilde{V}_R - \tilde{V}_{NR}}{(1-\varepsilon)\varepsilon_p} = \frac{\exp(-6 \cdot \ln(121.4) + 30)}{(1-0.38) \cdot 0.677} = 7.95$$

$$c_s^F = \frac{v_A \cdot A_A^{III} - (1+\alpha) \cdot m^{II}}{v_A \cdot A_A^{III} + (1+\alpha) \cdot \alpha \cdot m^{II}} \cdot c_s^{II}$$

$$= \frac{6 \cdot 7.95 - (1+1/2) \cdot 4.52}{6 \cdot 7.95 + (1+1/2) \cdot 1/2 \cdot 4.52} \cdot 130 \text{ mmol/kg}$$

$$= 104.1 \text{ mmol/kg}$$

which is the same as inserted in the calculation of $c_s^{III}$ above.

Correspondingly the feed salt concentration from calculated from the weakly bound component gives 97.1 mmol/kg giving $c_s^{III}$=119.0 mmol/kg The selectivity in section II is $$\alpha_{AB} = \frac{A_A}{A_B}$$

$$= \exp(\beta_A - \beta_B) \cdot c_s^{(\alpha_A - \alpha_B)}$$

$$= \exp(30 - 28.7) \cdot 130^{(-6+5.8)}$$

$$= 1.39$$

and in section III at (119 mmol/kg) it becomes $$\alpha_{AB} = \frac{A_A}{A_B}$$

$$= \exp(\beta_A - \beta_B) \cdot c^{(\alpha_A - \alpha_B)}$$

$$= \exp(30 - 28.7) \cdot 119^{(-6+5.8)}$$

$$= 1.41$$

It is seen that the selectivity is almost constant $$\frac{v_B - \alpha_{AB}^{III}}{v_B + \alpha \cdot \alpha_{AB}^{III}} \leq \frac{c_s^F}{c_s^{II}} \leq \frac{v_A - 1/\alpha_{AB}^{III}}{v_A + \alpha/\alpha_{AB}^{III}}$$

Insertion of the parameters gives $$\frac{5.8 - 1.41}{5.8 + 1/12 \cdot 1.41} \leq \frac{c_s^F}{c_s^{II}} \leq \frac{6 - 1/1.41}{6 + 1/2/1.41}$$

or $$0.67 \leq \frac{c_s^F}{c_s^{II}} \leq 0.83$$

Example 4

The following is an example of how other modifier concentrations in a Counter Current Purification system comprising RP HPLC or HIC solid phases may be determined.

For determination of $\ln(\tilde{V}_R - \tilde{V}_{NR})$ in:

$$\ln(\tilde{V}_R - \tilde{V}_{NR}) = \alpha_i \cdot c_m + \beta_i$$

the following parameters are used:

TABLE 6

| Component | Strongly Bound (A) | Weakly bound (B) |
|---|---|---|
| $\alpha_i$ | −0.5 | −0.51 |
| $\beta_i$ | 30 | 30.1 | and wherein the modifier concentration in the desorbent stream is set to 58.4 wt %.

With a 10 ml column volume, $V_R$, and a non retained volume, $V_{NR}$, of 8 ml, the following porosities can be used $\varepsilon = 0.38$, and $\varepsilon = 0.677$. The initial slope of the strongly bound components will be $$\frac{\tilde{V}_R - \tilde{V}_{NR}}{(1-\varepsilon)\varepsilon_p} = \frac{\exp(-0.5 \cdot 58.4 + 30)}{(1-0.38) \cdot 0.677} = 5.24$$

and correspondingly for the weakly bound component 3.23.

If the flow in section II is 9 ml/min and the columns are moved every $3^{rd}$ minuet the dimensionless flow in section II will be $$m^{II} = \frac{3\text{min} \cdot 9 \text{ ml/min} - 8 \text{ ml}}{10 \text{ ml} \cdot (1 - 0.38) \cdot .677} = 4.52$$

With a feed flow of 0 the feed salt concentration will for the strongly bound component be (bearing in mind that $K_{m,i} = \alpha_i$)

$$c_m^F = \frac{m^{II} \cdot (1+\alpha)^2}{K_{m,A} \cdot A_A^{III}} + c_m^{II} = \frac{4.52 \cdot (1+0)^2}{-0.5 \cdot 5.24} + 58.4 \text{ wt \%} = 56.7 \text{ wt \%}$$

and correspondingly for the weakly bound component $$c_m^F = \frac{m^{II} \cdot (1+\alpha)^2}{K_{m,A} \cdot A_A^{III}} + c_m^{II} = \frac{4.52 \cdot (1+0)^2}{-0.51 \cdot 3.23} + 58.4 \text{ wt \%} = 55.7 \text{ wt \%}$$

If the dimensionless feed flow $\alpha=\frac{1}{2}$ an iterative procedure is required since $A^{III}$ is a function of the salt concentration in section III, which depend on the feed salt concentration.

Using an iterative procedure the result for the strongly bound component gives $c_s^F = 55.9$ wt %. The result can easily be controlled by insertion in $$c_s^{III} = \frac{c_s^{II} + \alpha \cdot c_s^F}{1+\alpha} = \frac{58.4 \text{ wt \%} + 1/2 \cdot 55.9 \text{ wt \%}}{1 + 1/2} = 57.6 \text{ wt \%}$$

$$A_A^{II} = \frac{\tilde{V}_R - \tilde{V}_{NR}}{(1-\varepsilon)\varepsilon_p} = \frac{\exp(-0.50 \cdot 57.6 + 30)}{(1-0.38) \cdot 0.677} = 8.00$$

$$c_m^F = \frac{m^{II} \cdot (1+\alpha)^2}{K_{m,A} \cdot A_A^{III}} + c_m^{II}$$
$$= \frac{4.52 \cdot (1+1/2)^2}{-0.5 \cdot 8.00} + 58.4 \text{ wt \%}$$
$$= 55.9 \text{ wt \%}$$

which is the same as inserted in the calculation the calculation of $c_m^{III}$ above.

Correspondingly the feed salt concentration from calculated from the weakly bound component gives 55.0 wt % giving $c_m^{III} = 57.3$ wt %

The selectivity in section II is $\alpha_{AB}=\exp((\alpha_A-\alpha_B)\cdot c_m+(\beta_A-\beta_B))\exp((-0.50+0.51)\cdot 58.4$
   wt %+(30−30.1))=1.62 and in section III at (55.0 wt %) it becomes $\alpha_{AB}=\exp((\alpha_A-\alpha_B)\cdot c_m+(\beta_A-\beta_B))\exp((-0.50+0.51)\cdot 55.0$
   wt %+(30−30.1))=1.60

It is seen that the selectivity is almost constant $$\frac{1+1/2}{K_{m,B}} \cdot \alpha_{AB}^{III} \leq c_m^F - c_m^{II} \leq \frac{1}{K_{m,A} \cdot \alpha_{AB}^{III}}$$

Insertion of the parameters gives $$\frac{1+1/2}{-0.51} \cdot 1.60 \leq 58.4 \text{ wt \%} - c_m^{II} \leq \frac{1}{-0.5 \cdot 1.60}$$

or 53.7 wt % ≤ $c_m^{II}$ ≤ 57.1 wt %.

The invention claimed is:

1. A method for the chromatographic separation of a polypeptide of interest from a weaker bound component in a fluid mixture, comprising:

providing an open loop simulated moving bed counter current purification system comprising a plurality of sections in fluid connection, wherein the sections comprise at least one solid phase and a first desorbent stream;

introducing the fluid mixture as a feed stream into the counter current purification system to allow the fluid mixture to contact the at least one solid phase in a counter current mode, and wherein the concentration of the weaker bound component in the fluid mixture is lower than the concentration of the polypeptide of interest;

controlling the isotherm resulting from the introducing step by adjusting the concentration of at least one modifier in the feed stream so that the initial slope of the isotherm varies up to 10% from the slope of the operating line when a plot is made of dimensionless flow ($m^{III}$) the initial isotherm (A) as a function of feed flow ($Q^F$) or the feed flow divided by net flow ($\alpha$), wherein the initial slope of the isotherm is the slope of the isotherm as the concentration of the weaker bound component approaches 0 (zero), and wherein the at least one modifier is selected from the group consisting of salt, aqueous solvent, aqueous solvent comprising water and organic component, organic solvent, and pH; and separating the polypeptide of interest from the weaker bound component; wherein the chromatographic separation does not include size exclusion chromatography.

2. The method according to claim 1, further comprising at least one modifier in a stream in a section prior to the feed stream, wherein the at least one modifier in the feed stream is the same as the at least one modifier in the stream prior to the feed stream, and wherein the concentrations thereof are different.

3. The method according to claim 1, wherein the polypeptide of interest is glucagon-like peptide-1 (GLP-1) or a GLP-1 agonist.

4. The method according to claim 2, wherein the at least one modifier is salt.

5. The method according to claim 4, wherein the salt concentration in the feed stream ($c_s^F$) relative to the salt concentration in the stream in the section prior to the feed stream ($c_s^{II}$) is in the range:

$$\frac{v_B - \alpha_{AB}^{III}}{v_B + 1/2 \cdot \alpha_{AB}^{III}} \leq \frac{c_s^F}{c_s^{II}} \leq \frac{v_A - 1/\alpha_{AB}^{III}}{v_A},$$

wherein $$\alpha_{AB} = \frac{A_A}{A_B} = \exp(\beta_A - \beta_B) \cdot c_s^{(\alpha_a - \alpha_B)},$$

and wherein $\alpha_i$ and $\beta_i$ for components A and B are fitted to the retention volumes in a double logarithmic plot of:

$$\ln(\tilde{V}_R - \tilde{V}_{NR}) = \alpha_i \cdot \ln(c_s) + \beta_i.$$

6. The method according to claim 5, further comprising a chloride concentration of 45 mmol/kg in the stream in the section prior to the feed stream, wherein $c_s^F$ is in the range from about 17.5 mmol/kg to about 36 mmol/kg.

7. The method according to claim 1, wherein the desorbent stream comprises a salt selected from the group consisting of NaCl, KCl, NH$_4$Cl, CaCl$_2$, sodium acetate, potassium acetate, ammonium acetate, sodium citrate, potassium citrate, ammonium citrate, sodium sulphate, potassium sulphate, ammonium sulphate, calcium acetate, and mixtures thereof.

8. The method according to claim 1, wherein the modifier in the feed stream is organic.

9. The method according to claim 2, wherein the difference between the modifier in the feed stream ($c_s^F$) and the modifier in the stream in the section prior to the feed stream ($c_s^{II}$) is in the range:

$$\frac{1 + 1/2}{K_{m,B}} \cdot \alpha_{AB}^{III} \leq c_m^F - c_m^{II} \leq \frac{1}{K_{m,A} \cdot \alpha_{AB}^{III}},$$

wherein $$\alpha_{AB} = \frac{A_A}{A_B} = \frac{\exp(\alpha_A \cdot c_m + \beta_A)}{\exp(\alpha_B \cdot c_m + \beta_B)} = \exp((\alpha_A - \alpha_B) \cdot c_m + (\beta_A - \beta_B)),$$

and
wherein $\alpha_i$ and $\beta_i$ for component A and B are fitted to the retention volumes in a semi logarithmic plot to the function:

$$\ln(\tilde{V}_R - \tilde{V}_{NR}) = \alpha_i \cdot c_m \cdot \beta_i.$$

10. The method according to claim 1, wherein the modifier in the feed stream is present in the range from about 27.3 wt % to about 29.4 wt %, and wherein the desorbent comprises ethanol at about 30.8 wt %.

11. The method according to claim 1, wherein the least one modifier is a salt.

12. The method according to claim 1, wherein the least one modifier is an aqueous solvent or an aqueous solvent comprising water or organic solvent.

13. The method according to claim 1, wherein the at least one modifier is pH.

14. The method according to claim 2, wherein the section prior to the feed stream comprises the desorbent stream.

\* \* \* \* \*

SEQUENCE LISTING

```
<160> NUMBER OF SEQ ID NOS: 5

<210> SEQ ID NO 1
<211> LENGTH: 39
<212> TYPE: PRT
<213> ORGANISM: ARTIFICIAL
<220> FEATURE:
<223> OTHER INFORMATION: Human GLP-1
<220> FEATURE:
```

-continued

```
<221> NAME/KEY: VARIANT
<222> LOCATION: (1)..(1)
<223> OTHER INFORMATION: May be replaced by L-His, D-His, desamino-His,
      2-amino-His, alpha-hydroxy-His, homohistidine, Nalpha-acetyl-His,
      alpha-fluoromethyl-His, alpha-methyl-His, 3-pyridylalanine,
      2-pyridylalanine or 4-pyridylalanine
<220> FEATURE:
<221> NAME/KEY: VARIANT
<222> LOCATION: (2)..(2)
<223> OTHER INFORMATION: May be replaced by Gly, Val, Leu, Ile, Lys,
      Aib, (1-aminocyclopropyl) carboxylic acid, (1-aminocyclobutyl)
      carboxylic acid, (1-aminocyclopentyl) carboxylic
      acid, (1-aminocyclohexyl)carboxylic
<220> FEATURE:
<221> NAME/KEY: VARIANT
<222> LOCATION: (10)..(10)
<223> OTHER INFORMATION: may be replaced by Leu
<220> FEATURE:
<221> NAME/KEY: VARIANT
<222> LOCATION: (12)..(12)
<223> OTHER INFORMATION: may be replaced by Lys or Arg
<220> FEATURE:
<221> NAME/KEY: VARIANT
<222> LOCATION: (13)..(13)
<223> OTHER INFORMATION: may be replaced by Gln
<220> FEATURE:
<221> NAME/KEY: VARIANT
<222> LOCATION: (14)..(14)
<223> OTHER INFORMATION: may be replaced by Met or Lys
<220> FEATURE:
<221> NAME/KEY: VARIANT
<222> LOCATION: (16)..(16)
<223> OTHER INFORMATION: may be replaced by Glu or Aib
<220> FEATURE:
<221> NAME/KEY: VARIANT
<222> LOCATION: (17)..(17)
<223> OTHER INFORMATION: may be replaced by Glu, Lys or Arg
<220> FEATURE:
<221> NAME/KEY: VARIANT
<222> LOCATION: (19)..(19)
<223> OTHER INFORMATION: may be replaced by Val
<220> FEATURE:
<221> NAME/KEY: VARIANT
<222> LOCATION: (20)..(20)
<223> OTHER INFORMATION: may be replaced by Glu or Arg
<220> FEATURE:
<221> NAME/KEY: VARIANT
<222> LOCATION: (21)..(21)
<223> OTHER INFORMATION: may be replaced by Leu
<220> FEATURE:
<221> NAME/KEY: VARIANT
<222> LOCATION: (24)..(24)
<223> OTHER INFORMATION: may be replaced by Glu, Lys or Arg
<220> FEATURE:
<221> NAME/KEY: VARIANT
<222> LOCATION: (27)..(27)
<223> OTHER INFORMATION: may be replaced by Lys
<220> FEATURE:
<221> NAME/KEY: VARIANT
<222> LOCATION: (28)..(28)
<223> OTHER INFORMATION: may be replaced by Glu, Asn or Arg
<220> FEATURE:
<221> NAME/KEY: VARIANT
<222> LOCATION: (29)..(29)
<223> OTHER INFORMATION: may be replaced by Aib
<220> FEATURE:
<221> NAME/KEY: VARIANT
<222> LOCATION: (30)..(30)
<223> OTHER INFORMATION: may be replaced by Gly or Lys
<220> FEATURE:
<221> NAME/KEY: VARIANT
<222> LOCATION: (31)..(31)
<223> OTHER INFORMATION: may alternatively be absent or replaced by Ala,
      Glu, Pro, Lys or amide
<220> FEATURE:
<221> NAME/KEY: VARIANT
<222> LOCATION: (32)..(32)
<223> OTHER INFORMATION: may alternatively be absent or replaced by Lys
      or amide
```

```
<220> FEATURE:
<221> NAME/KEY: VARIANT
<222> LOCATION: (33)..(33)
<223> OTHER INFORMATION: may alternatively be absent or replaced by Lys
      or amide
<220> FEATURE:
<221> NAME/KEY: VARIANT
<222> LOCATION: (34)..(34)
<223> OTHER INFORMATION: may alternatively be absent or replaced by
      amide
<220> FEATURE:
<221> NAME/KEY: VARIANT
<222> LOCATION: (35)..(35)
<223> OTHER INFORMATION: may alternatively be absent or replaced by
      amide
<220> FEATURE:
<221> NAME/KEY: VARIANT
<222> LOCATION: (36)..(36)
<223> OTHER INFORMATION: may alternatively be absent or replaced by
      amide
<220> FEATURE:
<221> NAME/KEY: VARIANT
<222> LOCATION: (37)..(37)
<223> OTHER INFORMATION: may alternatively be absent or replaced by
      amide
<220> FEATURE:
<221> NAME/KEY: VARIANT
<222> LOCATION: (38)..(38)
<223> OTHER INFORMATION: may alternatively be absent or replaced by
      amide
<220> FEATURE:
<221> NAME/KEY: VARIANT
<222> LOCATION: (39)..(39)
<223> OTHER INFORMATION: may alternatively be absent or replaced by
      Ser-amide or amide

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Ser
            20                  25                  30

Ser Gly Ala Pro Pro Ser
        35

<210> SEQ ID NO 2
<211> LENGTH: 31
<212> TYPE: PRT
<213> ORGANISM: ARTIFICIAL
<220> FEATURE:
<223> OTHER INFORMATION: Human GLP-1
<220> FEATURE:
<221> NAME/KEY: MISC_FEATURE
<222> LOCATION: (31)..(31)
<223> OTHER INFORMATION: is P or Y

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa
            20                  25                  30

<210> SEQ ID NO 3
<211> LENGTH: 40
<212> TYPE: PRT
<213> ORGANISM: Heloderma suspectum

<400> SEQUENCE: 3

His Ser Asp Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
```

-continued

```
                 20                  25                  30
Ser Ser Gly Ala Pro Pro Pro Ser
             35                  40

<210> SEQ ID NO 4
<211> LENGTH: 40
<212> TYPE: PRT
<213> ORGANISM: Heloderma suspectum

<400> SEQUENCE: 4

His Gly Glu Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
             20                  25                  30

Ser Ser Gly Ala Pro Pro Pro Ser
             35                  40

<210> SEQ ID NO 5
<211> LENGTH: 44
<212> TYPE: PRT
<213> ORGANISM: ARTIFICIAL
<220> FEATURE:
<223> OTHER INFORMATION: Human GLP-1
<220> FEATURE:
<221> NAME/KEY: MOD_RES
<222> LOCATION: (44)..(44)
<223> OTHER INFORMATION: AMIDATION: The Lys residue in the amidated form

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
             20                  25                  30

Ser Gly Ala Pro Pro Ser Lys Lys Lys Lys Lys Lys
             35                  40
```